(12) United States Patent
Abdou

(10) Patent No.: US 8,771,355 B2
(45) Date of Patent: Jul. 8, 2014

(54) INTER-VERTEBRAL DISC MOTION DEVICES AND METHODS OF USE

(76) Inventor: M. S. Abdou, San Diego, CA (US)

( * ) Notice: Subject to any disclaimer, the term of this patent is extended or adjusted under 35 U.S.C. 154(b) by 1319 days.

(21) Appl. No.: 11/754,979

(22) Filed: May 29, 2007

(65) Prior Publication Data

US 2007/0282448 A1    Dec. 6, 2007

Related U.S. Application Data

(60) Provisional application No. 60/809,066, filed on May 26, 2006, provisional application No. 60/840,594, filed on Aug. 28, 2006, provisional application No. 60/850,473, filed on Oct. 10, 2006, provisional application No. 60/878,612, filed on Jan. 4, 2007.

(51) Int. Cl.
*A61F 2/44* (2006.01)
*A61B 17/70* (2006.01)

(52) U.S. Cl.
USPC .................................... 623/17.11; 606/279

(58) Field of Classification Search
USPC ............ 623/17.11–17.16; 606/246–249, 256, 606/257, 279
See application file for complete search history.

(56) References Cited

U.S. PATENT DOCUMENTS

| | | | |
|---|---|---|---|
| 4,759,769 A | 7/1988 | Hedman et al. | |
| 4,997,432 A | 3/1991 | Keller | |
| 5,425,773 A | 6/1995 | Boyd et al. | |
| 5,514,180 A | 5/1996 | Heggeness et al. | |
| 5,556,431 A | 9/1996 | Buttner-Janz | |
| 5,562,738 A | 10/1996 | Boyd et al. | |
| 5,674,294 A | 10/1997 | Bainville et al. | |
| 5,674,296 A | 10/1997 | Bryan et al. | |
| 5,676,701 A | 10/1997 | Yuan et al. | |
| 5,976,186 A | 11/1999 | Bao et al. | |
| 6,001,130 A | 12/1999 | Bryan et al. | |
| 6,019,792 A | 2/2000 | Cauthen | |
| 6,022,376 A | 2/2000 | Assell et al. | |
| 6,093,205 A | 7/2000 | McLeod et al. | |
| 6,179,873 B1 | 1/2001 | Zientek | |
| 6,355,038 B1 | 3/2002 | Pisharodi | |
| 6,419,706 B1 | 7/2002 | Graf | |
| 6,440,168 B1 | 8/2002 | Cauthen | |
| 6,461,358 B1 | 10/2002 | Faccioli et al. | |
| 6,482,234 B1 | 11/2002 | Weber et al. | |
| 6,527,803 B1 | 3/2003 | Crozet et al. | |
| 6,592,624 B1 | 7/2003 | Fraser et al. | |
| 6,610,093 B1 | 8/2003 | Pisharodi | |
| 6,679,915 B1 | 1/2004 | Cauthen | |

(Continued)

FOREIGN PATENT DOCUMENTS

| WO | WO 2008/021319 | 2/2002 |
|---|---|---|
| WO | 2004016217 A2 | 2/2004 |

(Continued)

*Primary Examiner* — Pedro Philogene
*Assistant Examiner* — David Comstock
(74) *Attorney, Agent, or Firm* — Gazdzinski & Associates, PC

(57) ABSTRACT

A mobile device is adapted to at least partially replace the motion characteristics of a natural inter-vertebral disc positioned in a disc space. In an embodiment, a receptacle is coupled to the bearing surface. The receptacle is adapted to accept an implantable material without the removal of the bearing surface, wherein the implantable material contacts the abutment surface of each of the vertebral bodies adjacent to the disc space and leads to fusion and immobilization of two vertebral bodies adjacent the disc space.

51 Claims, 96 Drawing Sheets

(56) References Cited

U.S. PATENT DOCUMENTS

| | | |
|---|---|---|
| 6,706,068 B2 | 3/2004 | Ferree |
| 6,709,461 B2 | 3/2004 | O'Neil et al. |
| 6,723,127 B2 | 4/2004 | Ralph et al. |
| 6,749,635 B1 | 6/2004 | Bryan |
| 6,758,861 B2 | 7/2004 | Ralph et al. |
| 6,764,515 B2 | 7/2004 | Ralph et al. |
| 6,770,096 B2 | 8/2004 | Bolger et al. |
| 7,083,622 B2 | 8/2006 | Simonson |
| 7,083,649 B2 | 8/2006 | Zucherman et al. |
| 7,101,399 B2 | 9/2006 | Errico et al. |
| 7,128,761 B2 | 10/2006 | Kuras et al. |
| 7,204,853 B2 | 4/2007 | Gordon et al. |
| 7,273,496 B2 | 9/2007 | Mitchell |
| 7,316,714 B2 | 1/2008 | Gordon et al. |
| 7,331,995 B2 | 2/2008 | Eisermann et al. |
| 7,594,932 B2 | 9/2009 | Aferzon et al. |
| 7,695,517 B2 | 4/2010 | Benzel et al. |
| 7,727,280 B2 | 6/2010 | McLuen |
| 7,749,274 B2 | 7/2010 | Razian |
| 7,799,081 B2 | 9/2010 | McKinley |
| 2001/0039452 A1 | 11/2001 | Zucherman et al. |
| 2003/0065395 A1 | 4/2003 | Ralph et al. |
| 2003/0078662 A1 | 4/2003 | Ralph et al. |
| 2003/0176923 A1 | 9/2003 | Keller et al. |
| 2003/0208273 A1 | 11/2003 | Eisermann et al. |
| 2003/0217809 A1 | 11/2003 | Morishige |
| 2004/0049280 A1* | 3/2004 | Cauthen .................... 623/17.14 |
| 2004/0068318 A1 | 4/2004 | Coates et al. |
| 2004/0143264 A1* | 7/2004 | McAfee ........................ 606/61 |
| 2004/0220670 A1 | 11/2004 | Eisermann et al. |
| 2004/0225364 A1 | 11/2004 | Richelsoph et al. |
| 2004/0225365 A1 | 11/2004 | Eisermann et al. |
| 2004/0225366 A1 | 11/2004 | Eisermann et al. |
| 2004/0236425 A1 | 11/2004 | Huang |
| 2004/0243240 A1 | 12/2004 | Beaurain et al. |
| 2004/0267369 A1 | 12/2004 | Lyons et al. |
| 2005/0033431 A1 | 2/2005 | Gordon et al. |
| 2005/0043800 A1 | 2/2005 | Paul et al. |
| 2005/0043802 A1 | 2/2005 | Eisermann et al. |
| 2005/0071007 A1 | 3/2005 | Malek |
| 2005/0125066 A1 | 6/2005 | McAfee |
| 2005/0165487 A1 | 7/2005 | Muhanna et al. |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0192671 A1 | 9/2005 | Bao et al. |
| 2005/0197702 A1 | 9/2005 | Coppes et al. |
| 2005/0216083 A1 | 9/2005 | Michelson |
| 2005/0222682 A1 | 10/2005 | Link et al. |
| 2005/0234555 A1 | 10/2005 | Sutton et al. |
| 2005/0240273 A1 | 10/2005 | Khandkar et al. |
| 2005/0256576 A1 | 11/2005 | Moskowitz et al. |
| 2005/0283241 A1 | 12/2005 | Keller et al. |
| 2006/0015183 A1 | 1/2006 | Gilbert et al. |
| 2006/0069436 A1 | 3/2006 | Sutton et al. |
| 2006/0069438 A1 | 3/2006 | Zucherman |
| 2006/0084988 A1 | 4/2006 | Kim |
| 2006/0106395 A1 | 5/2006 | Link et al. |
| 2006/0116768 A1 | 6/2006 | Krueger et al. |
| 2006/0178746 A1 | 8/2006 | Bartish, Jr. et al. |
| 2006/0190082 A1 | 8/2006 | Keller et al. |
| 2006/0195192 A1 | 8/2006 | Gordon et al. |
| 2006/0276900 A1 | 12/2006 | Carpenter |
| 2007/0021836 A1 | 1/2007 | Doty |
| 2007/0161992 A1 | 7/2007 | Kwak et al. |
| 2007/0162133 A1 | 7/2007 | Doubler et al. |
| 2007/0191958 A1 | 8/2007 | Abdou |
| 2008/0015698 A1 | 1/2008 | Marino et al. |
| 2008/0027550 A1 | 1/2008 | Link et al. |
| 2008/0039843 A1 | 2/2008 | Abdou |
| 2008/0281358 A1 | 11/2008 | Abdou |
| 2010/0087858 A1 | 4/2010 | Abdou |

FOREIGN PATENT DOCUMENTS

| | | |
|---|---|---|
| WO | WO 2007/095333 | 8/2007 |
| WO | WO 2007/140382 | 12/2007 |
| WO | WO 2008/021319 | 2/2008 |
| WO | WO 2008/073447 | 6/2008 |

* cited by examiner

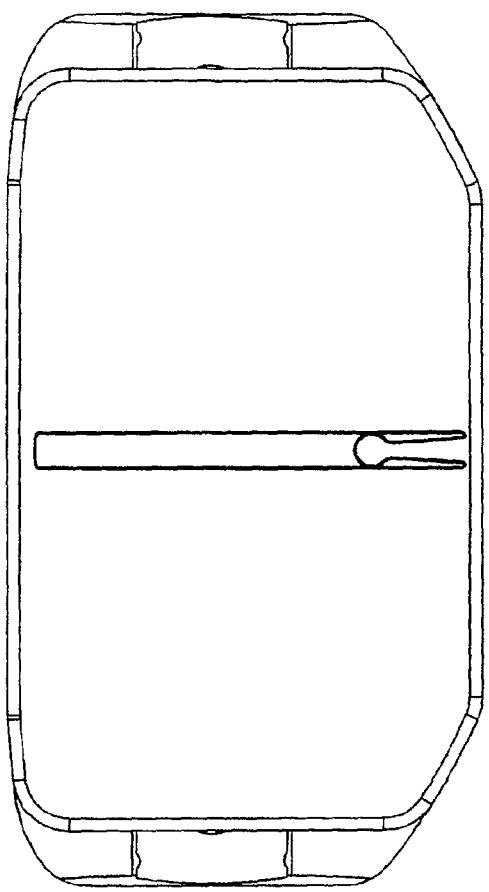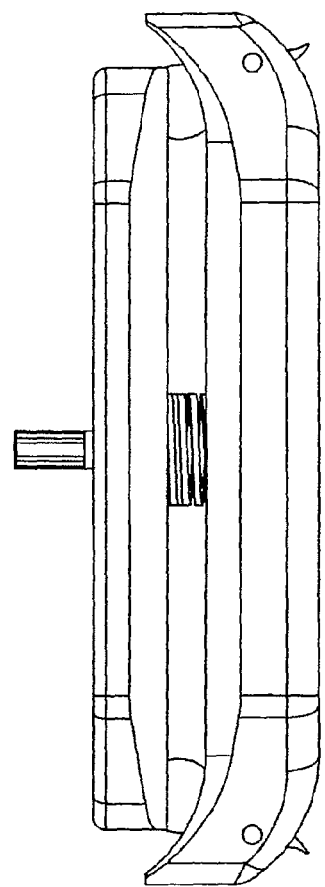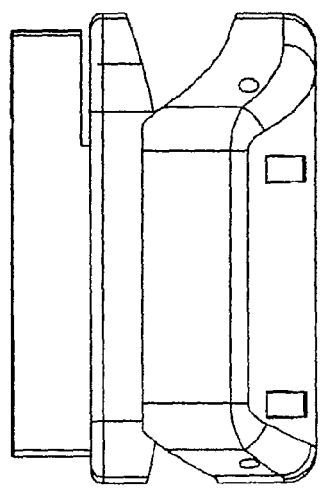
Fig. 2

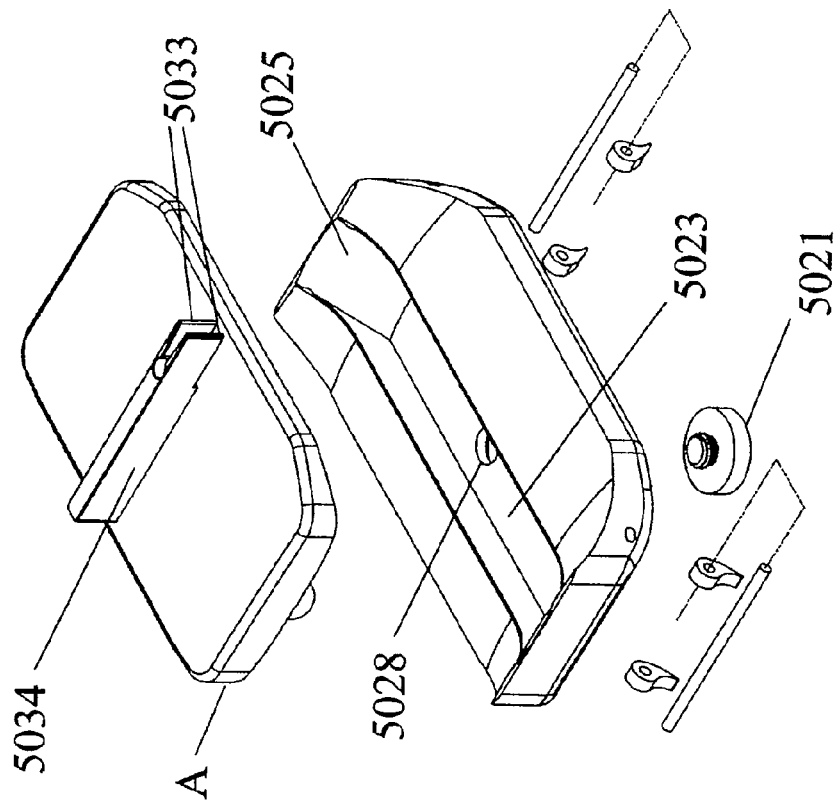
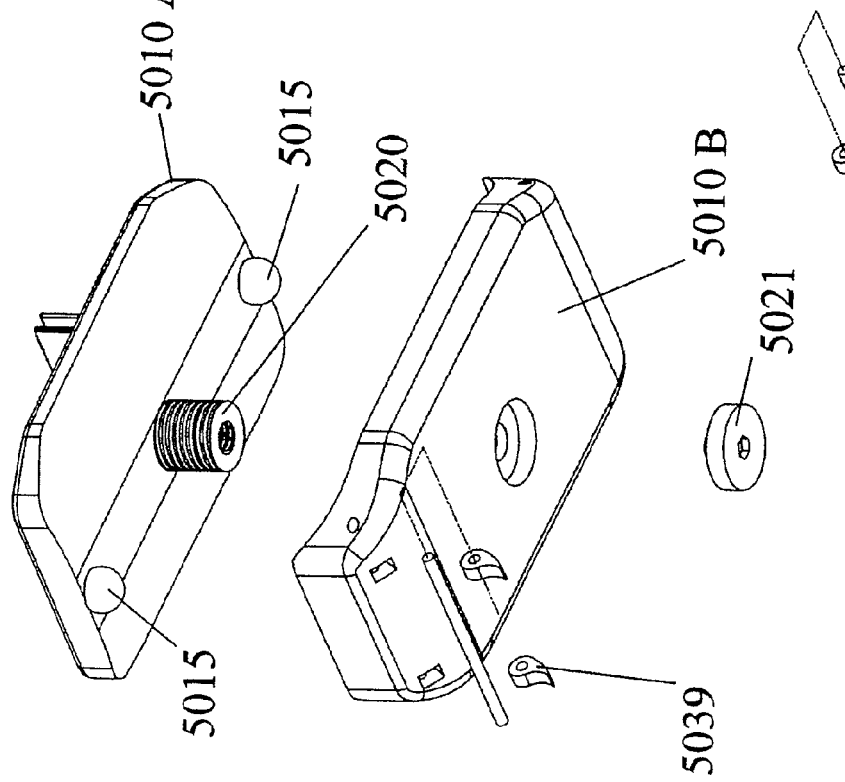
Fig. 3A
Fig. 3B

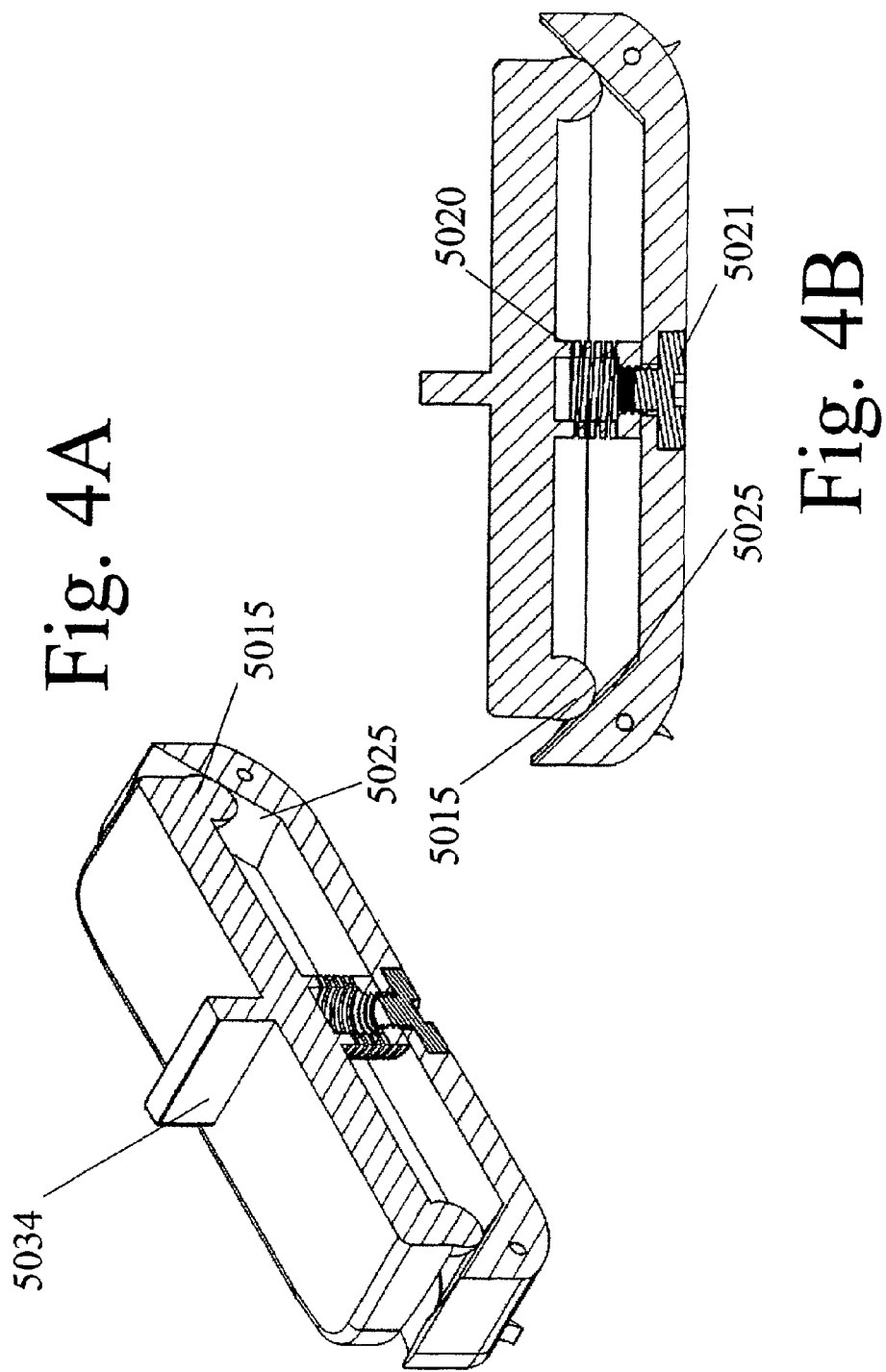

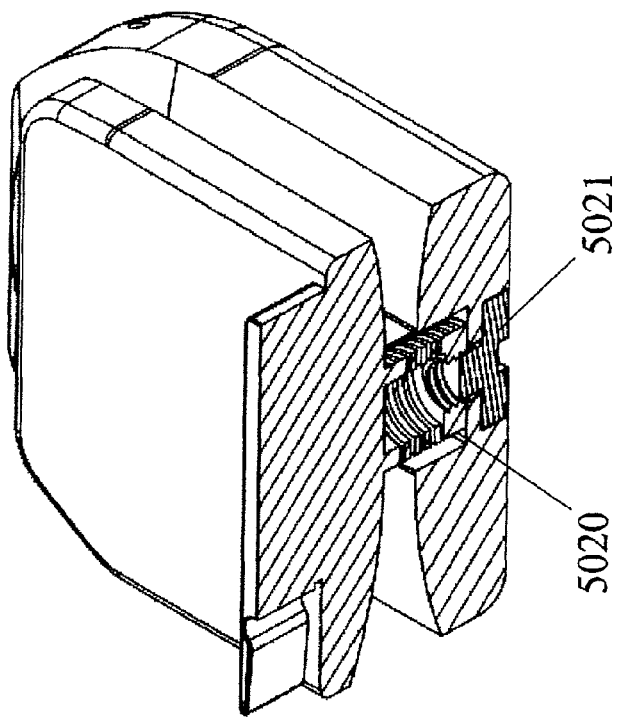
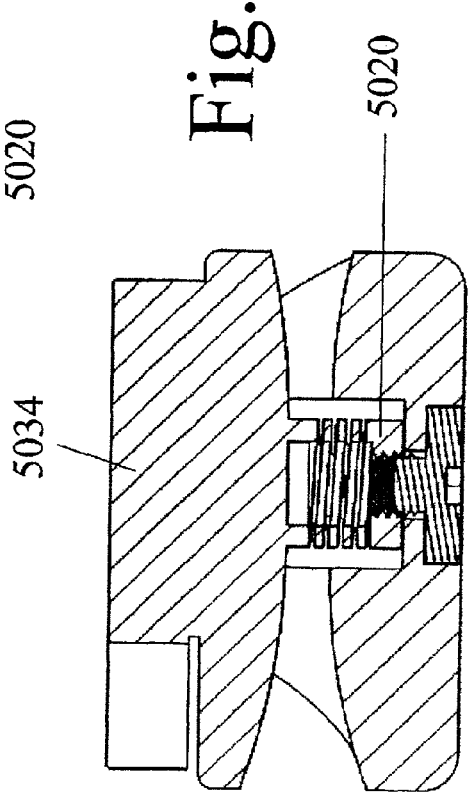

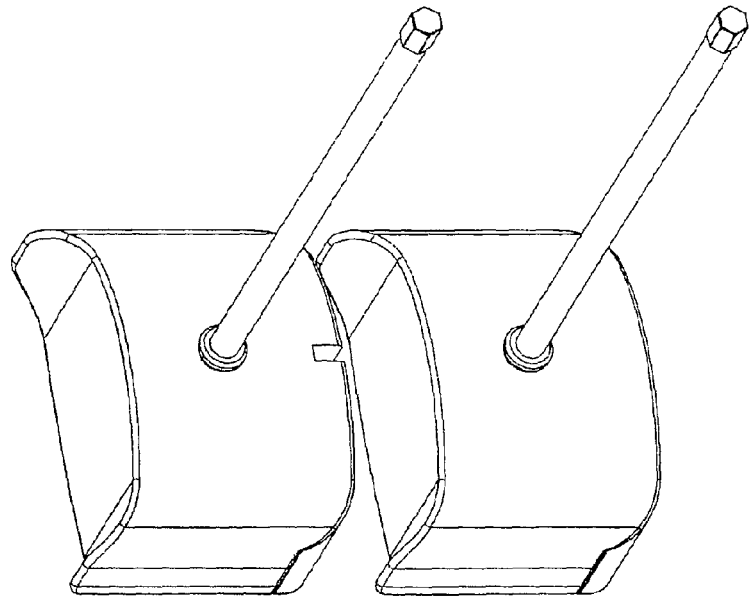
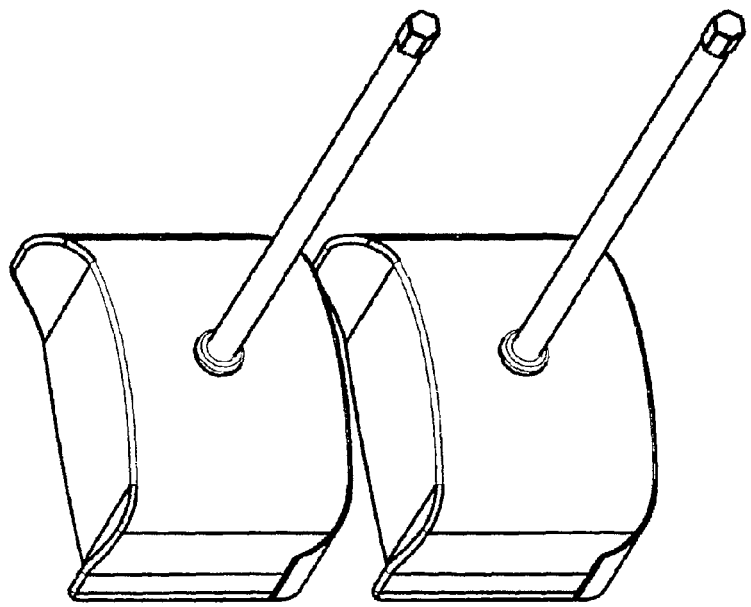

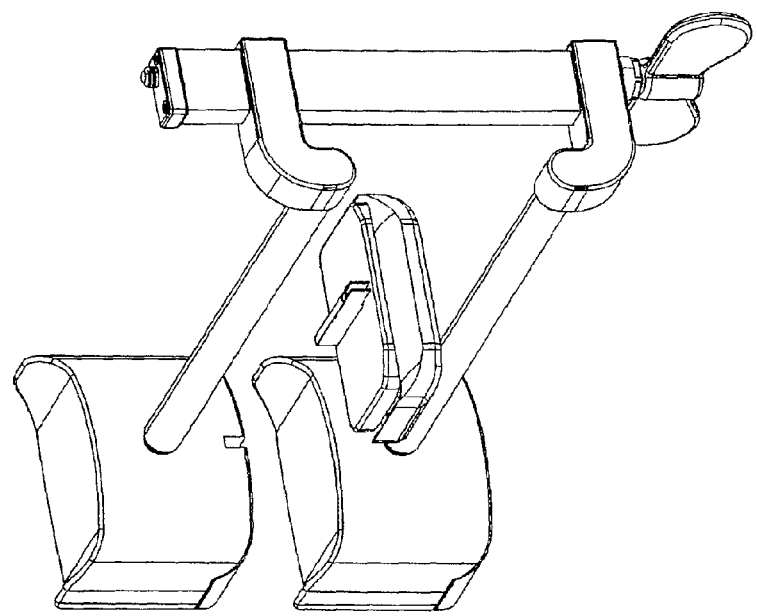
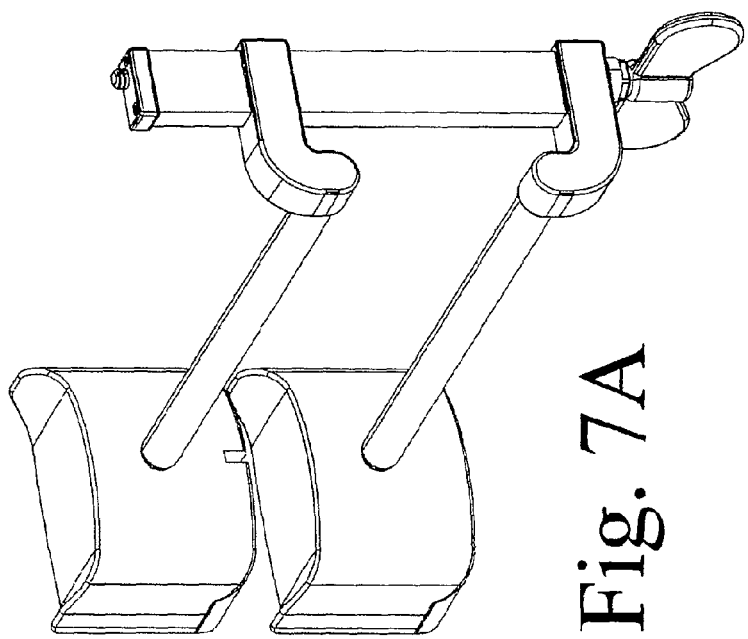

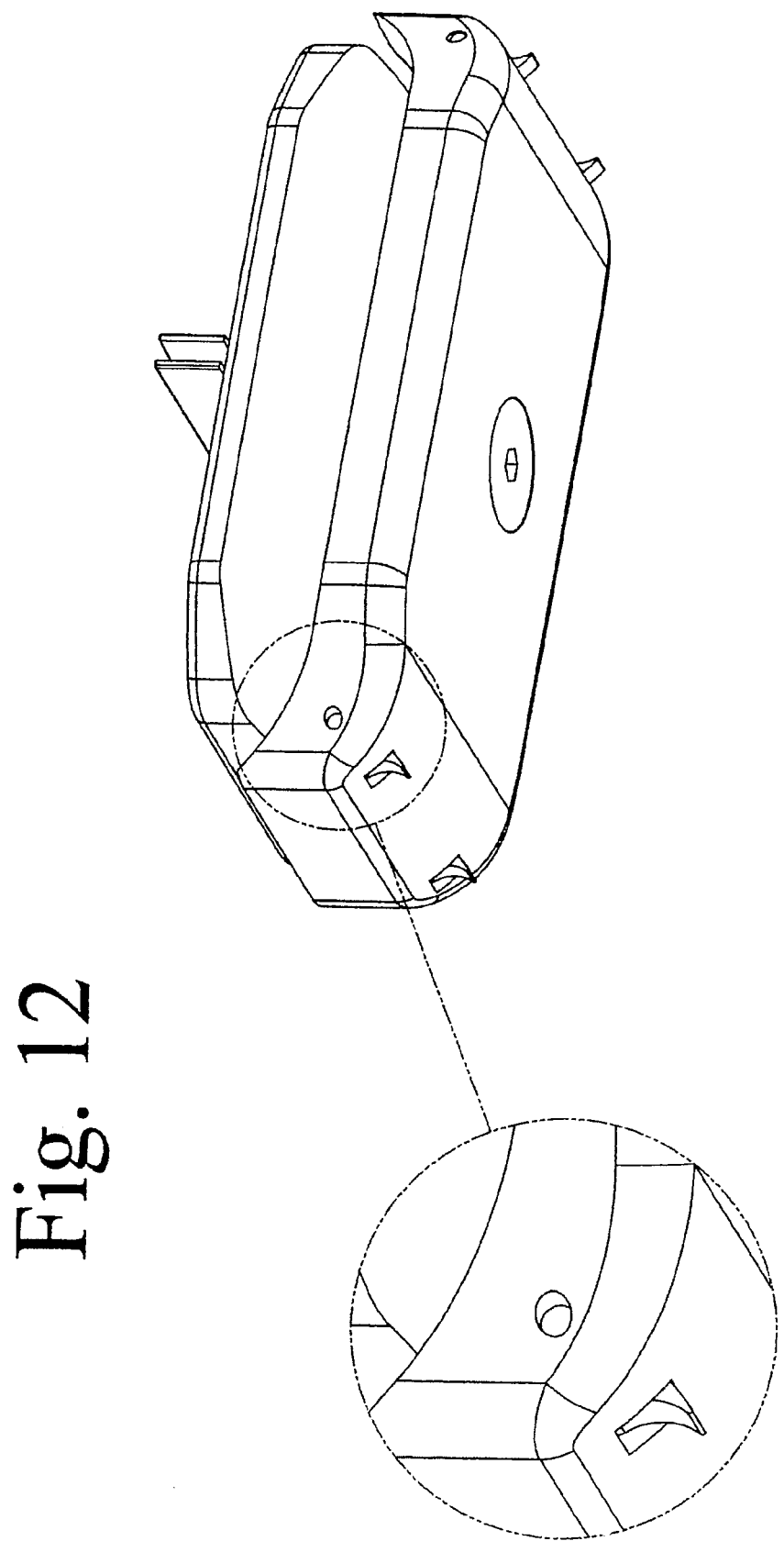

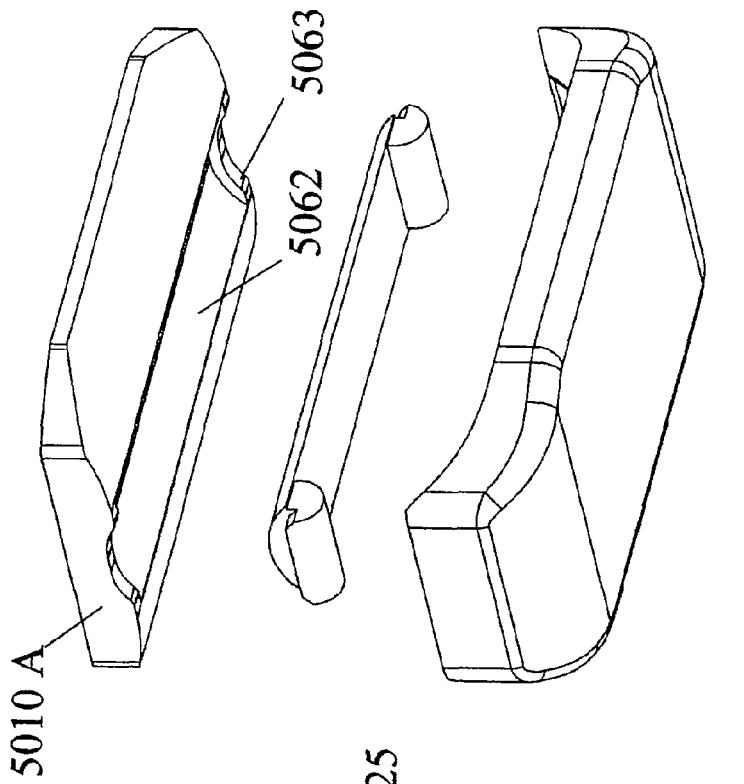
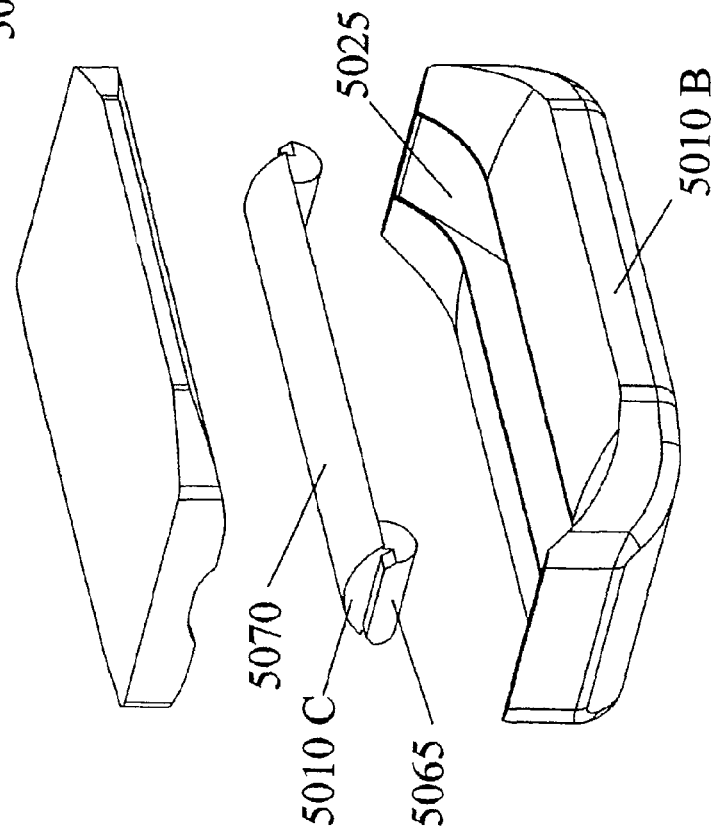
Fig. 19A
Fig. 19B

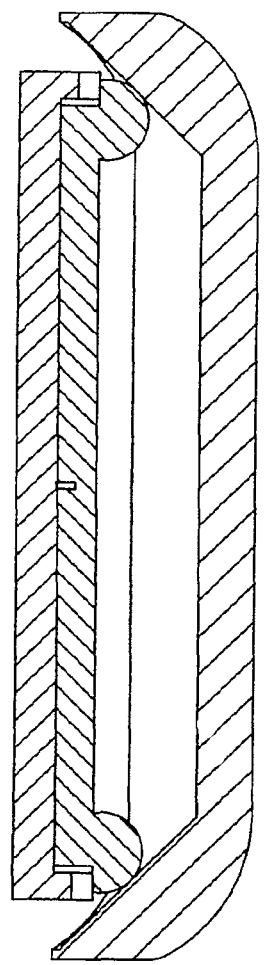
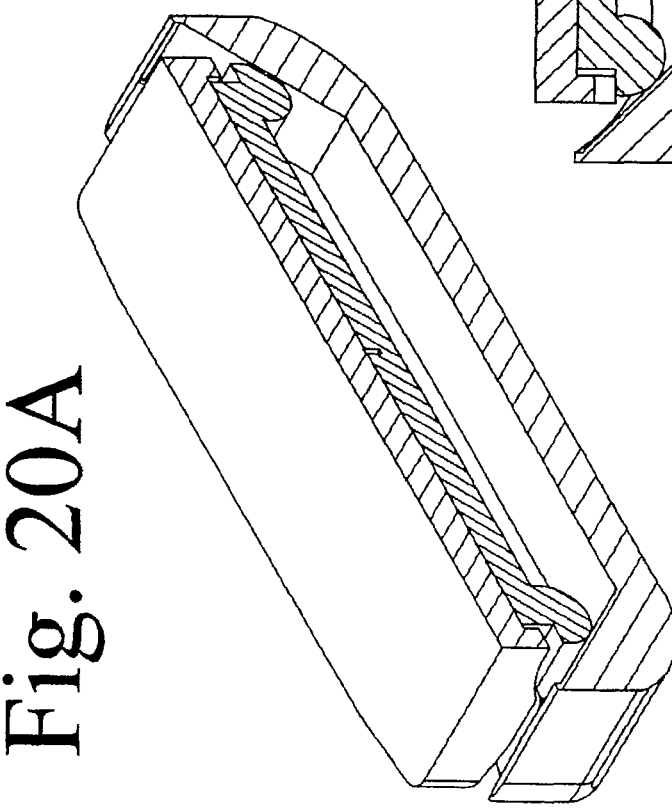
Fig. 20B
Fig. 20A

6200

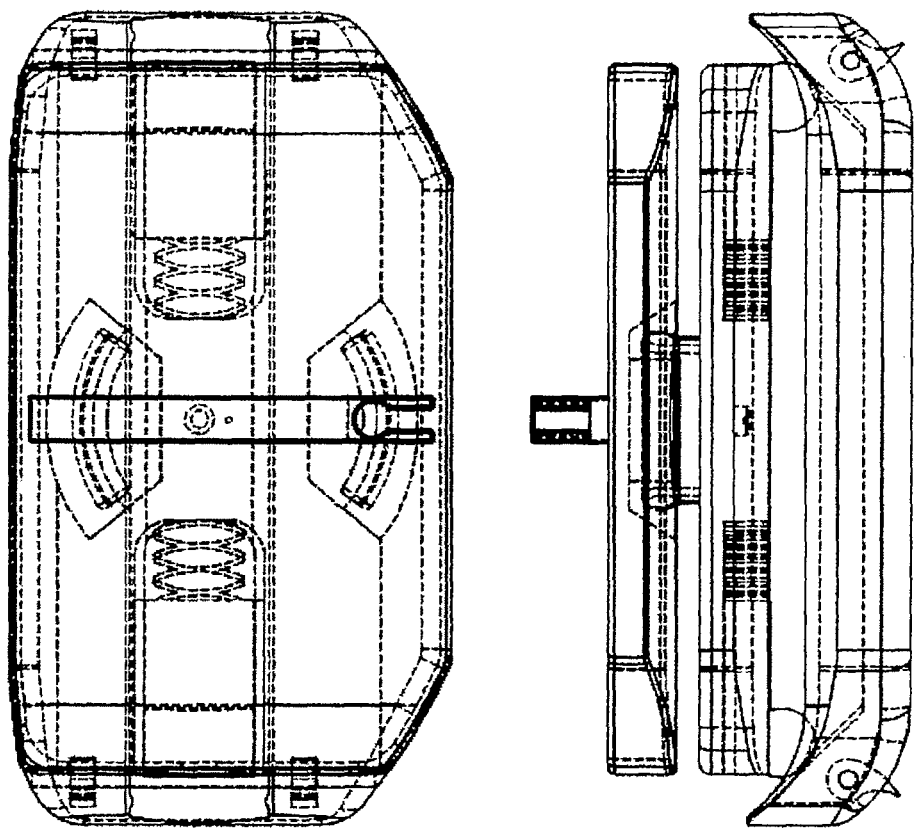
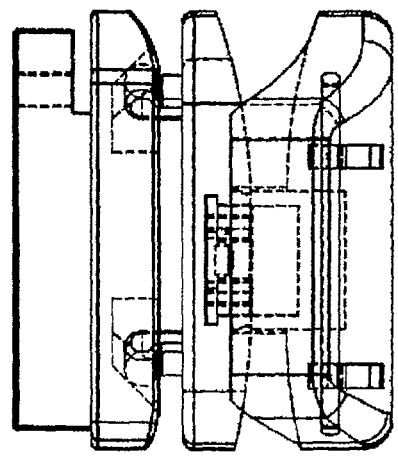
Fig. 24

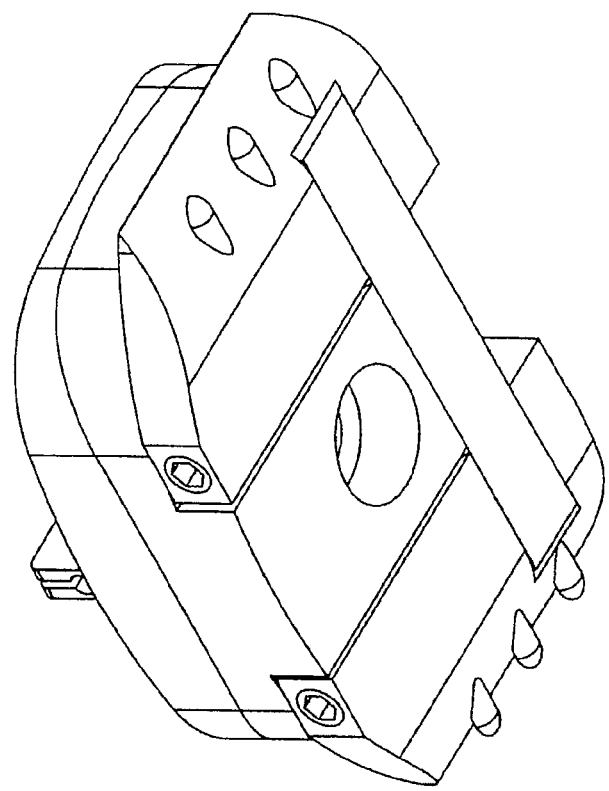
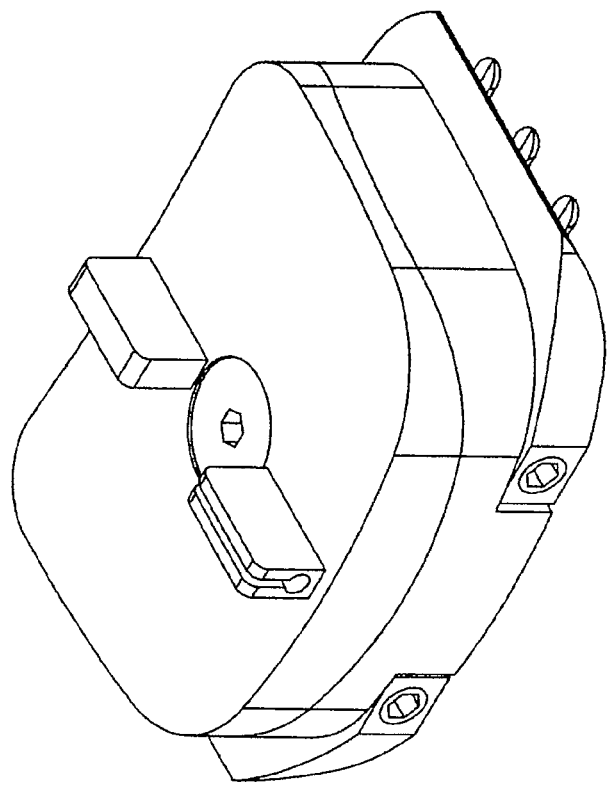
Fig. 28

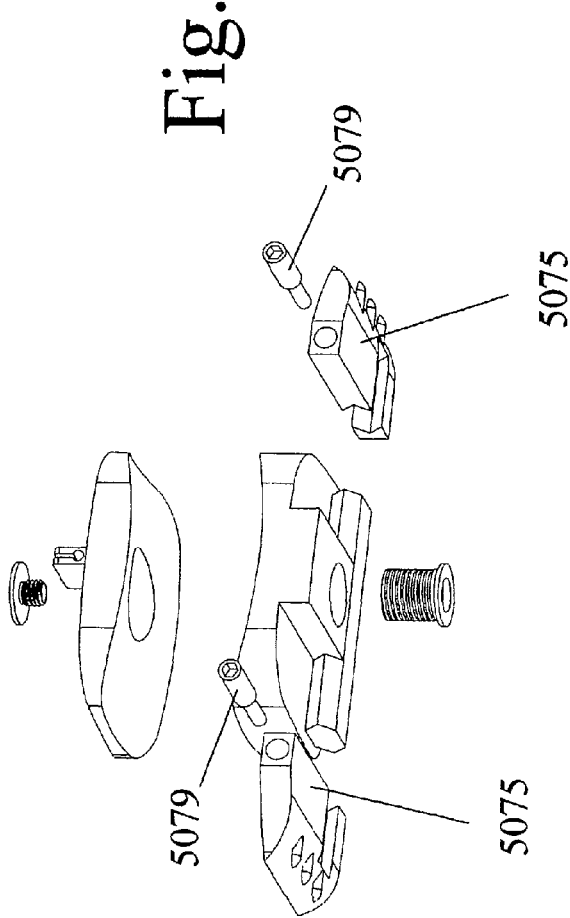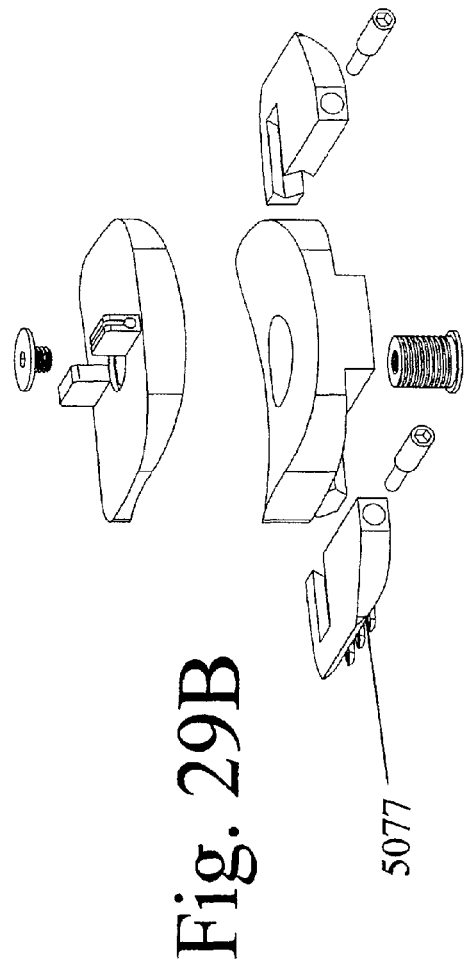

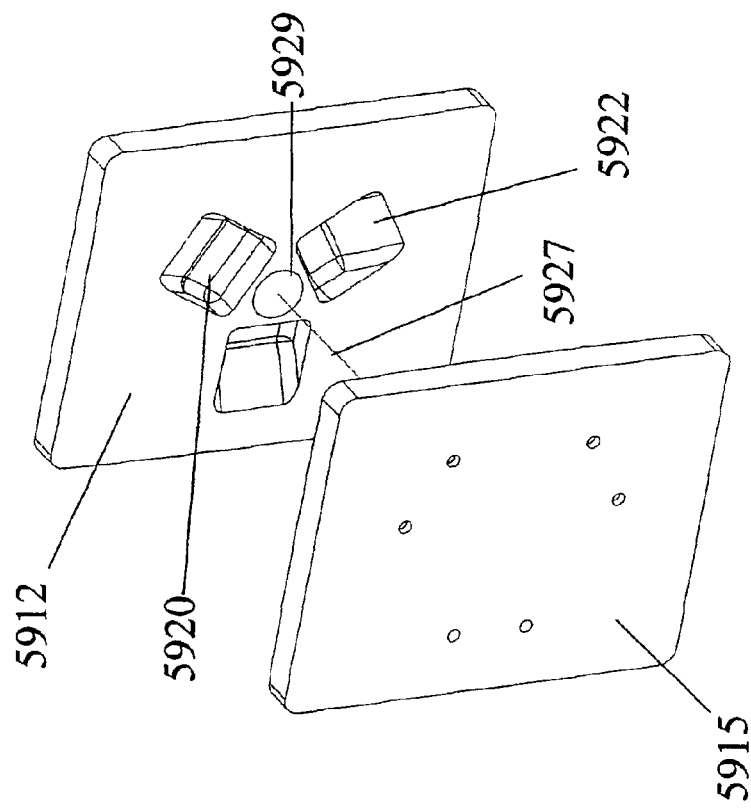
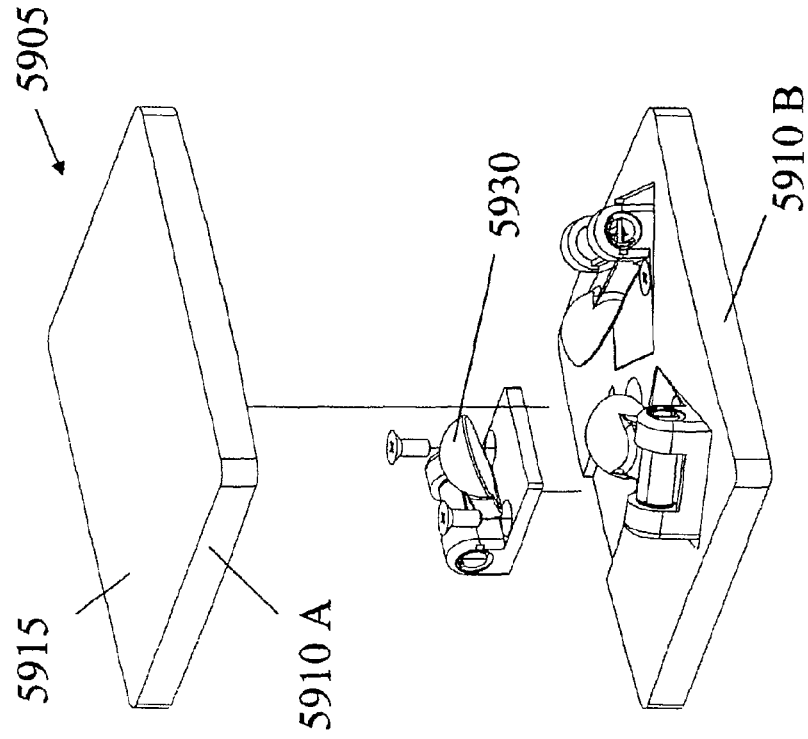

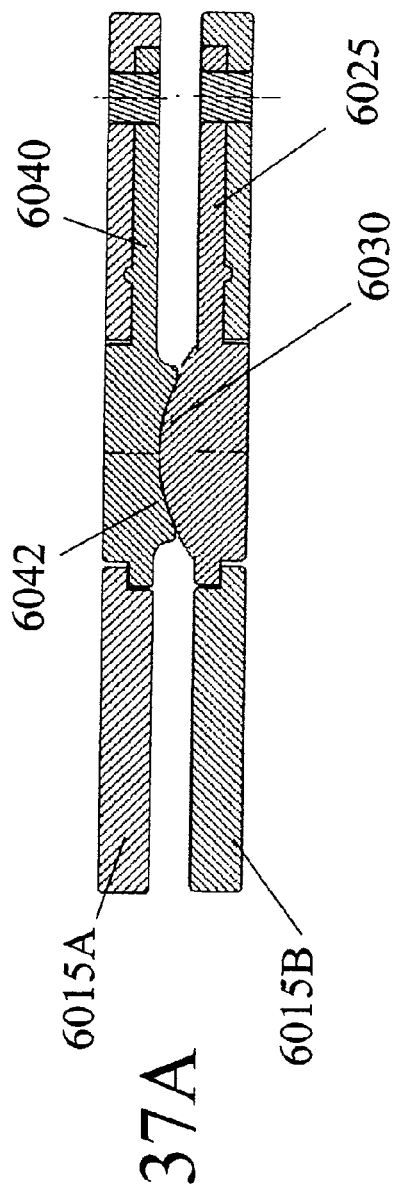
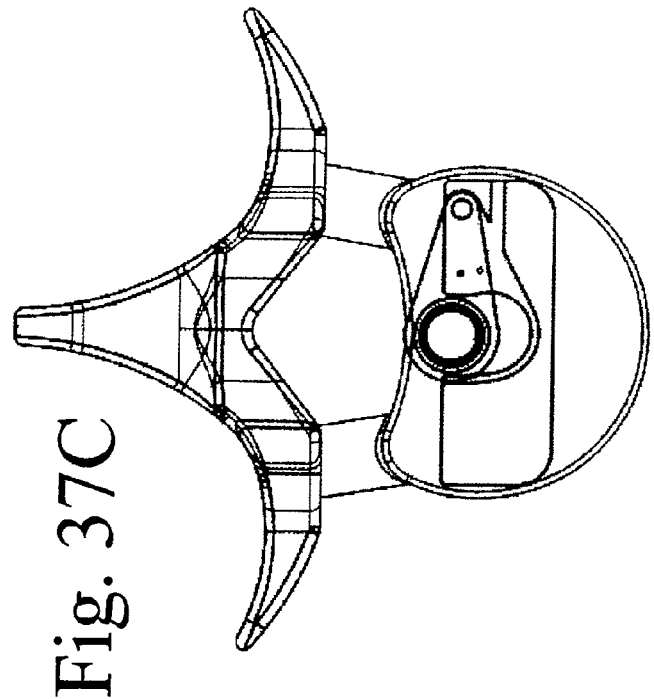
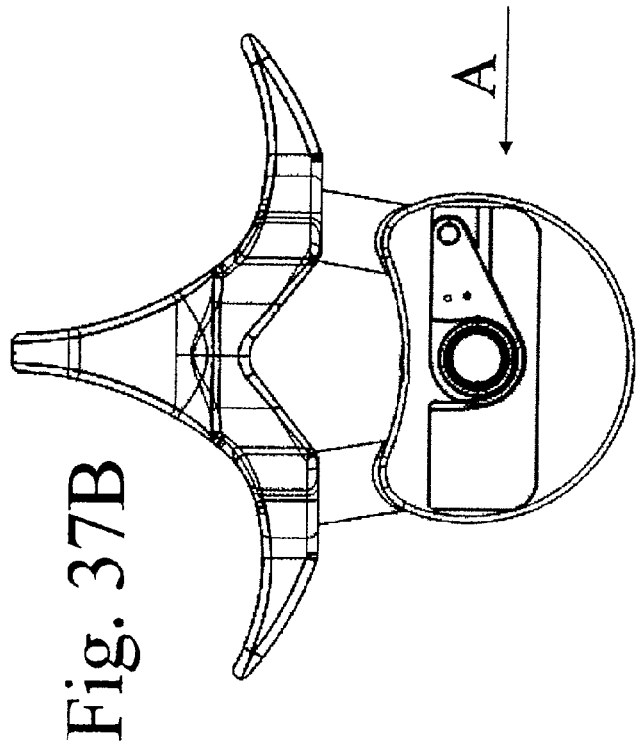
Fig. 37A
Fig. 37B
Fig. 37C

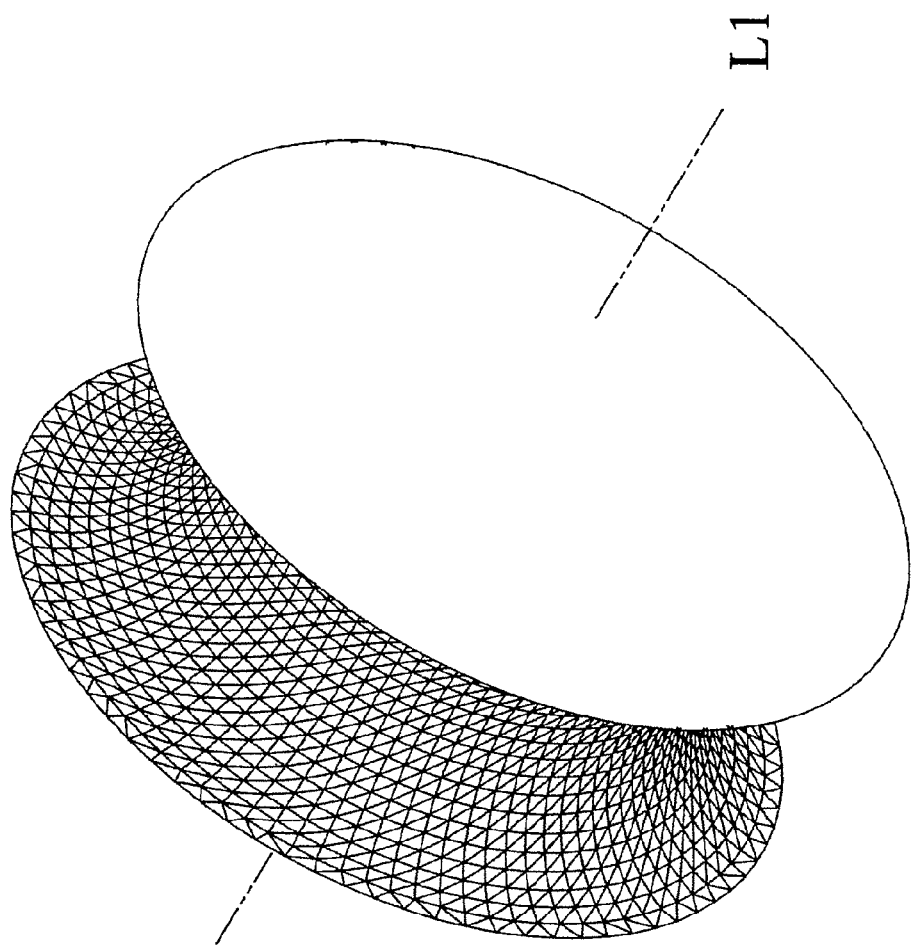
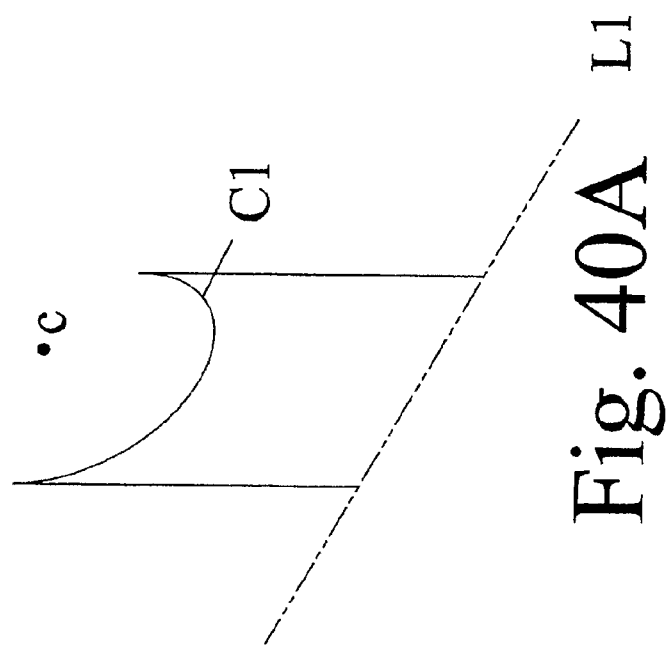
Fig. 40B
Fig. 40A

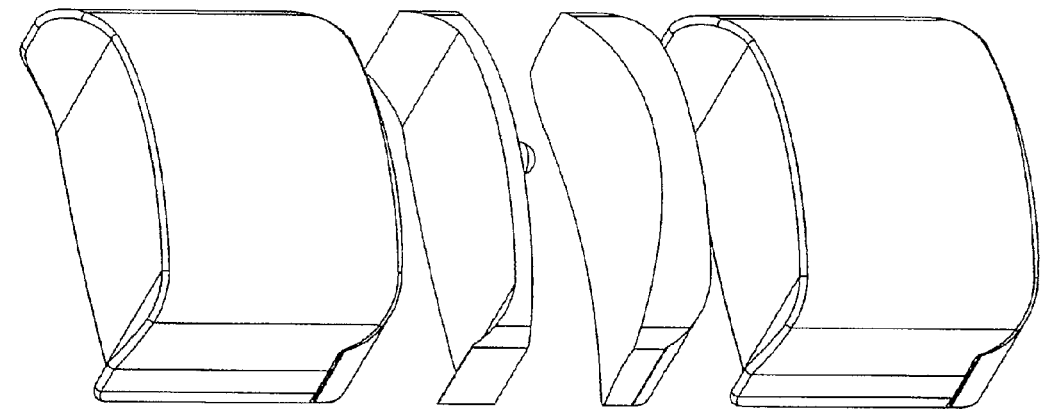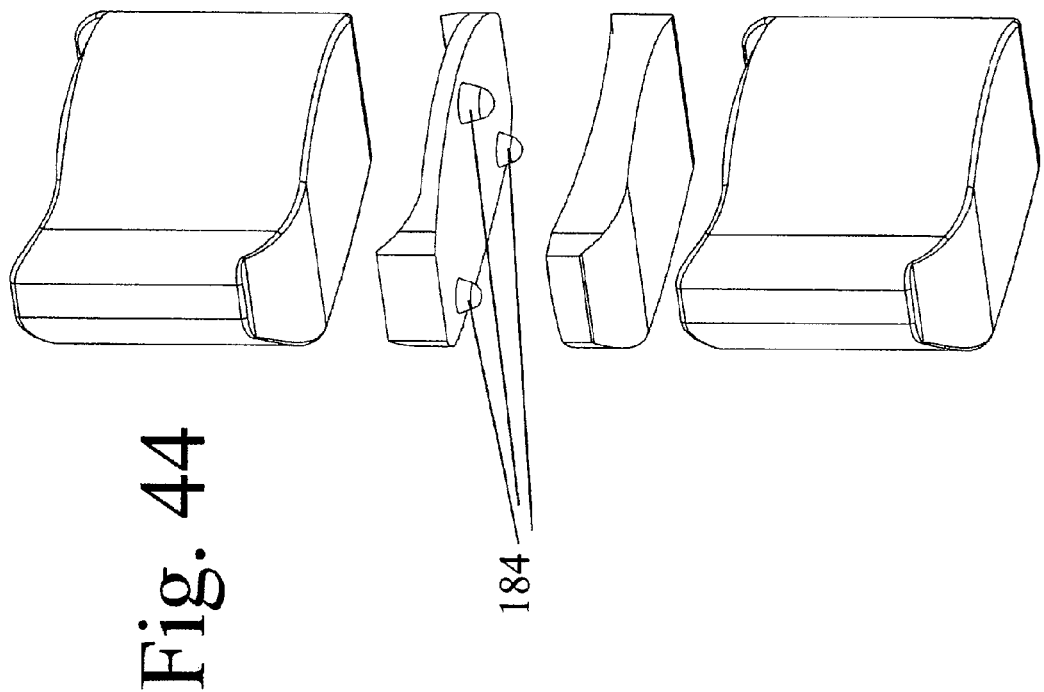
Fig. 44

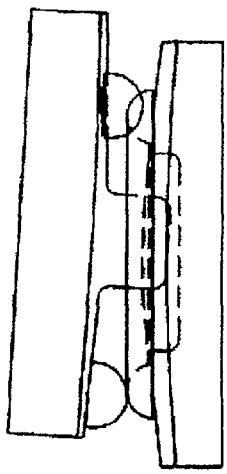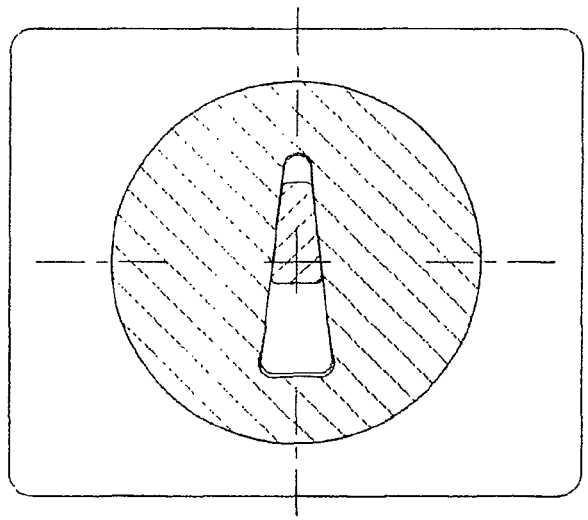
Fig. 47C
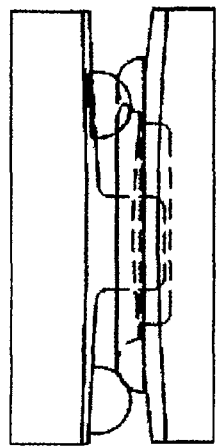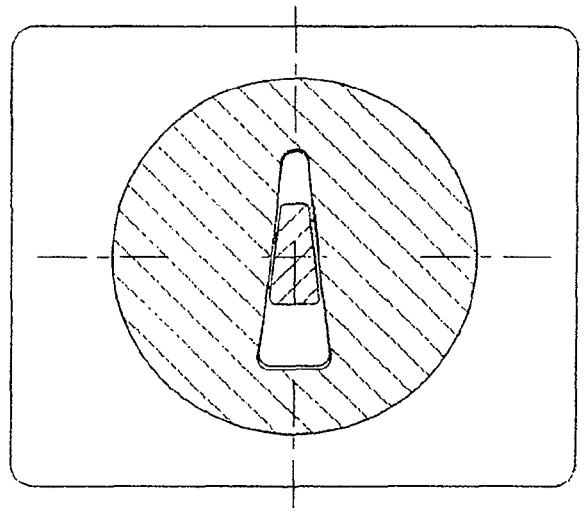
Fig. 47B
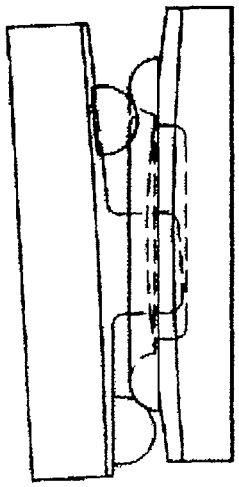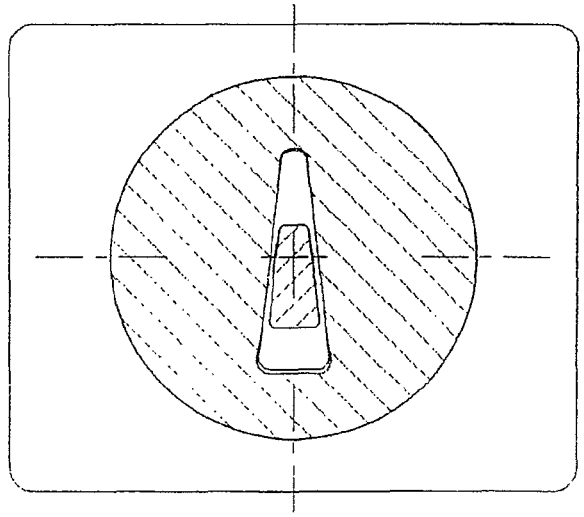
Fig. 47A

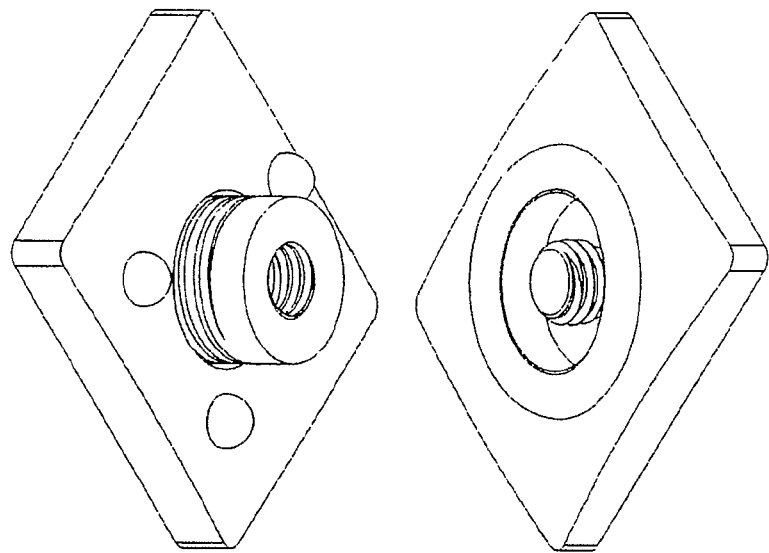
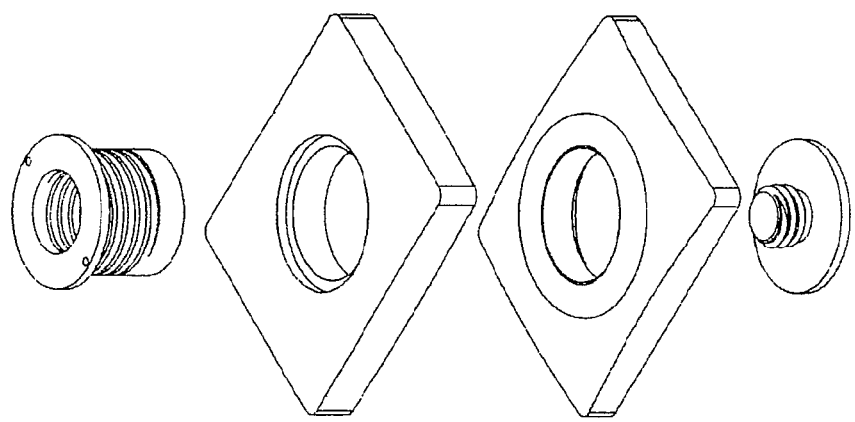

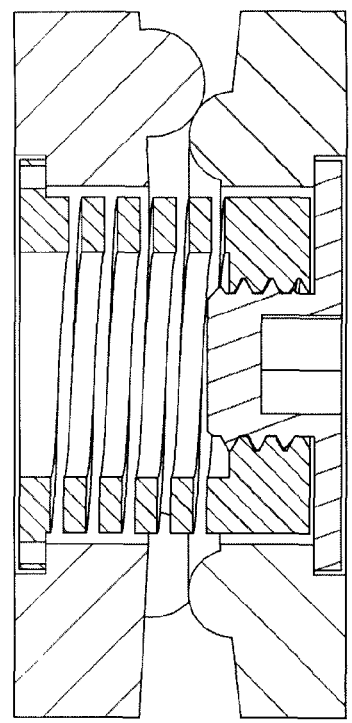
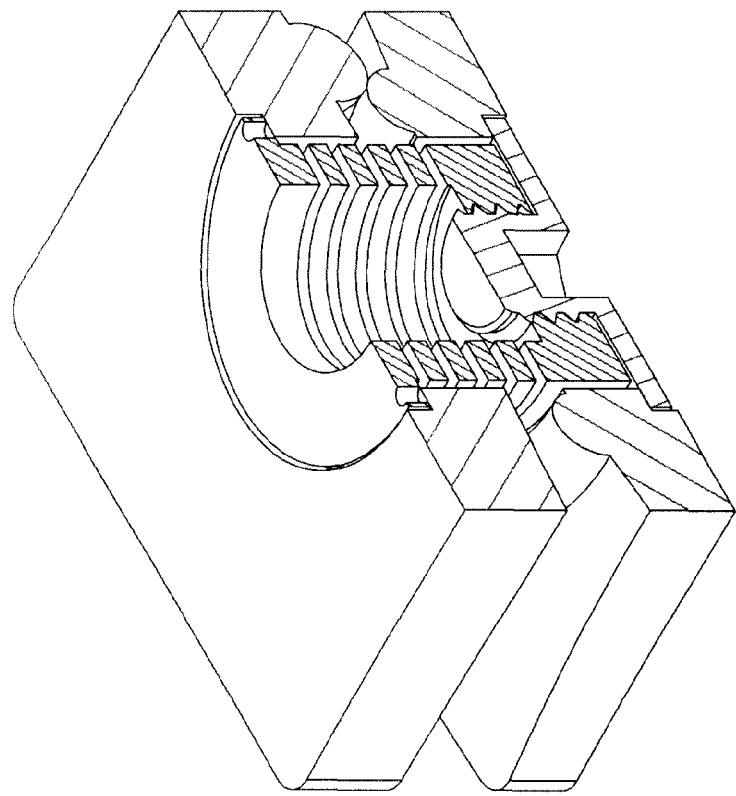
Fig. 51

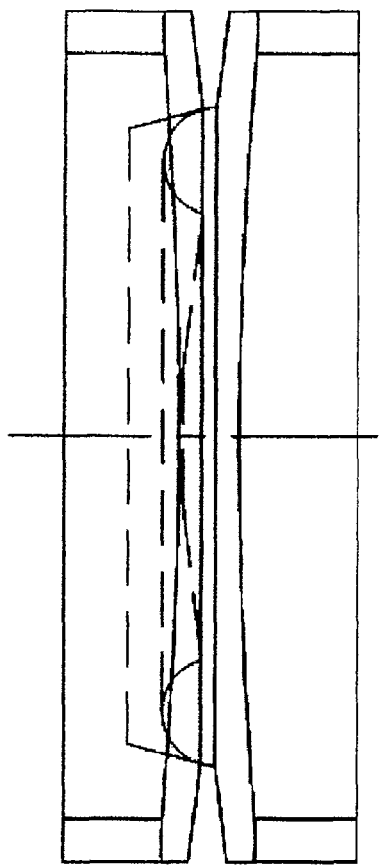
Fig. 53A
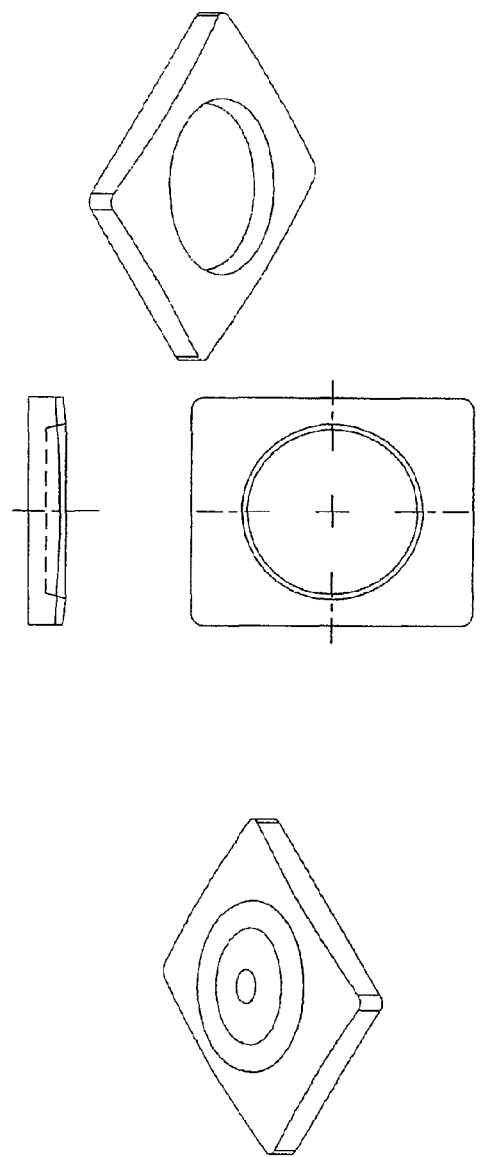
Fig. 53C
Fig. 53B

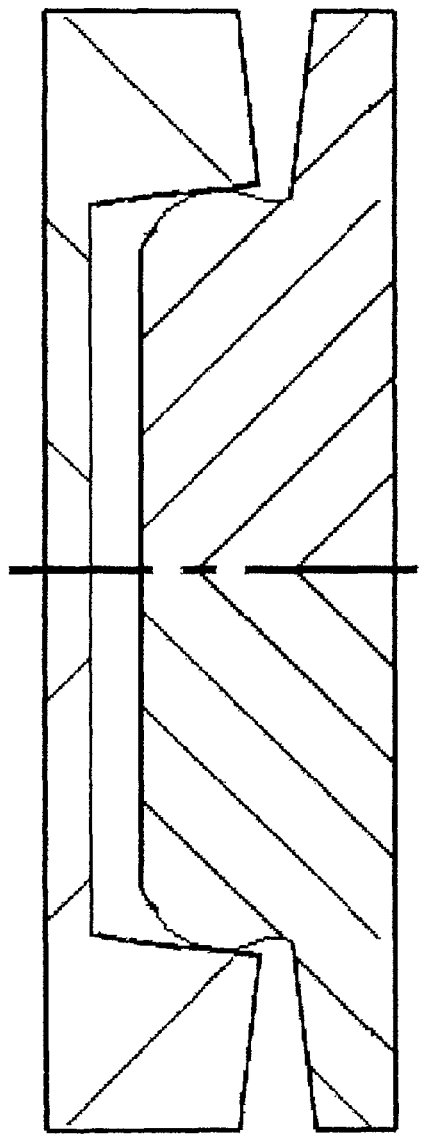
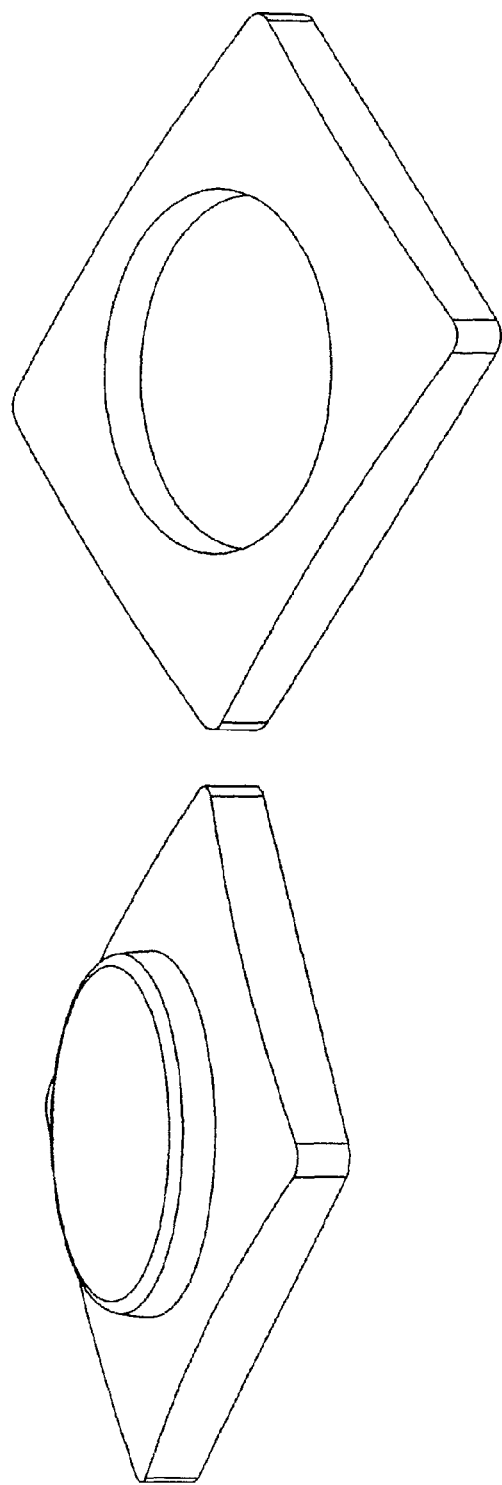
Fig. 54

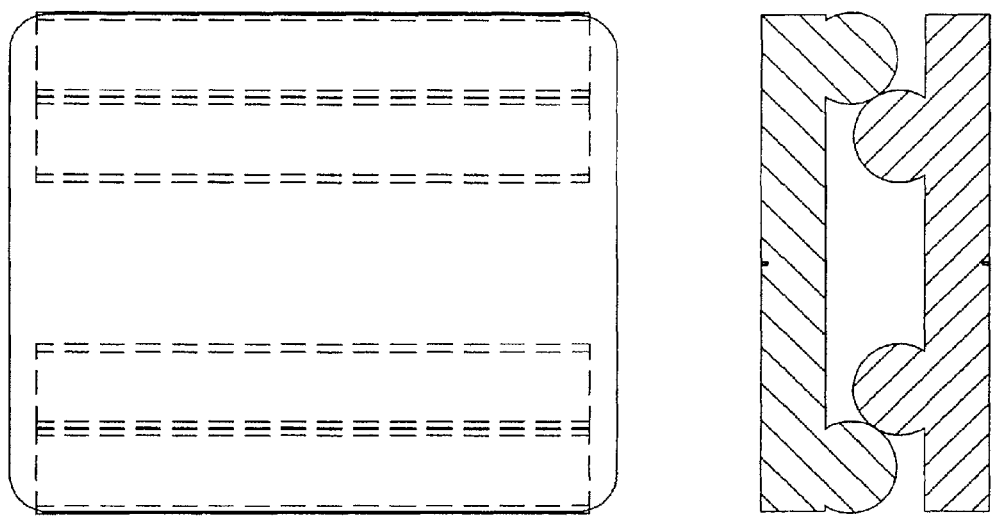
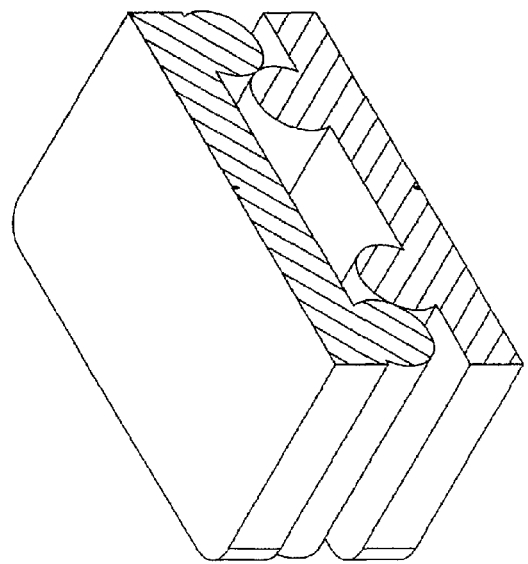
Fig. 55

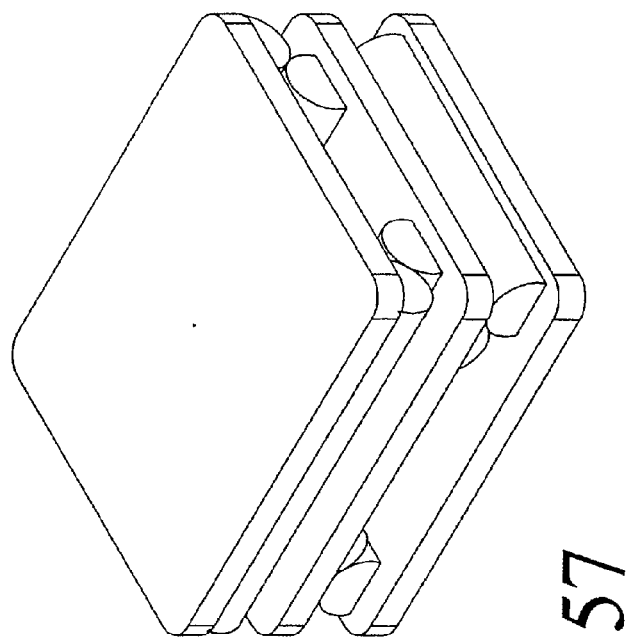
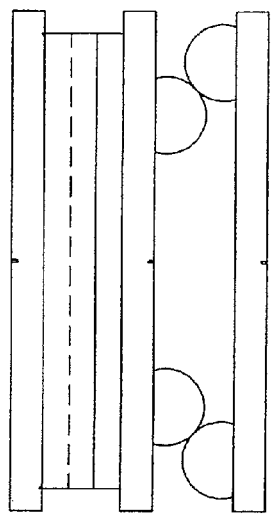
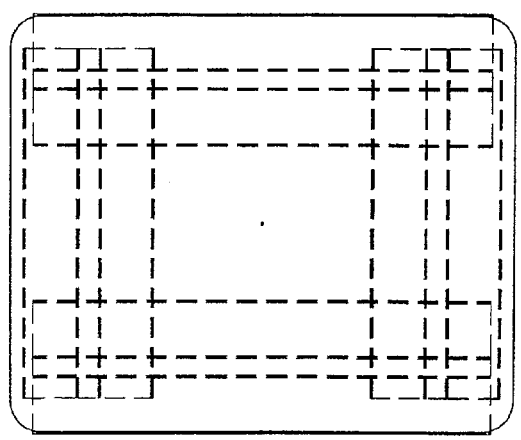
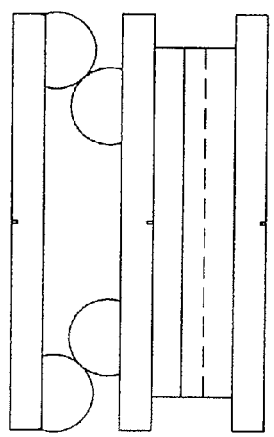
Fig. 57

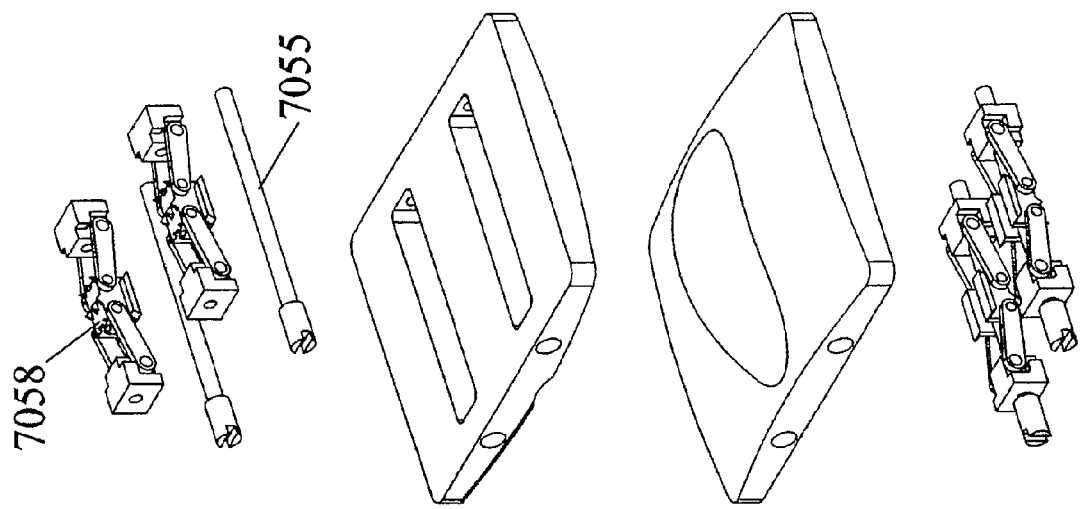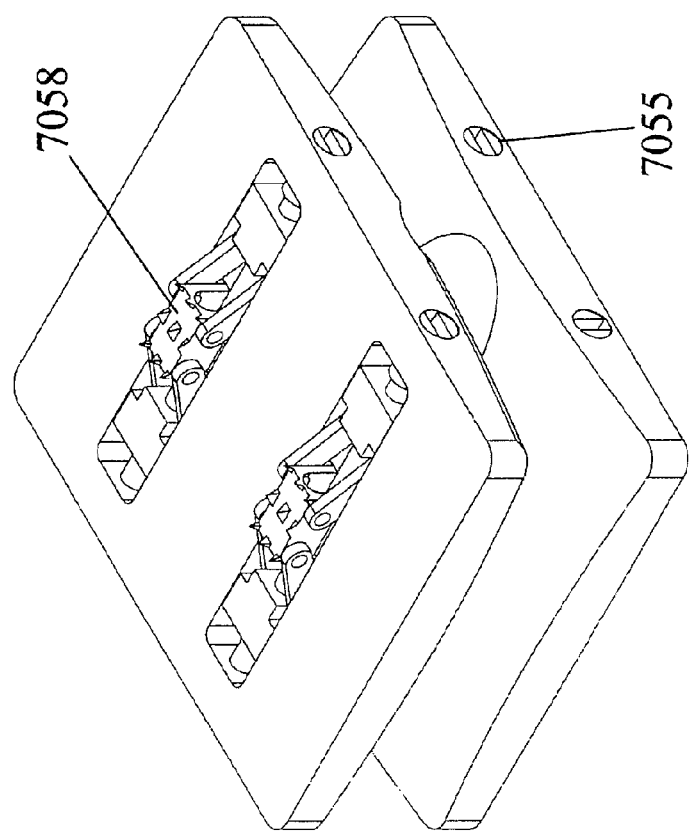
Fig. 61

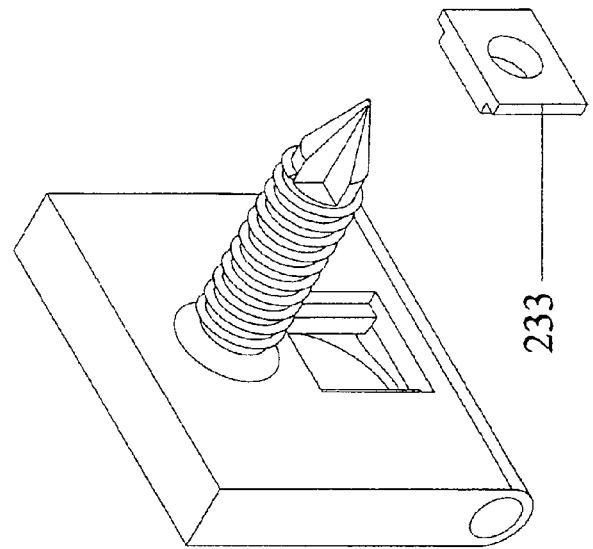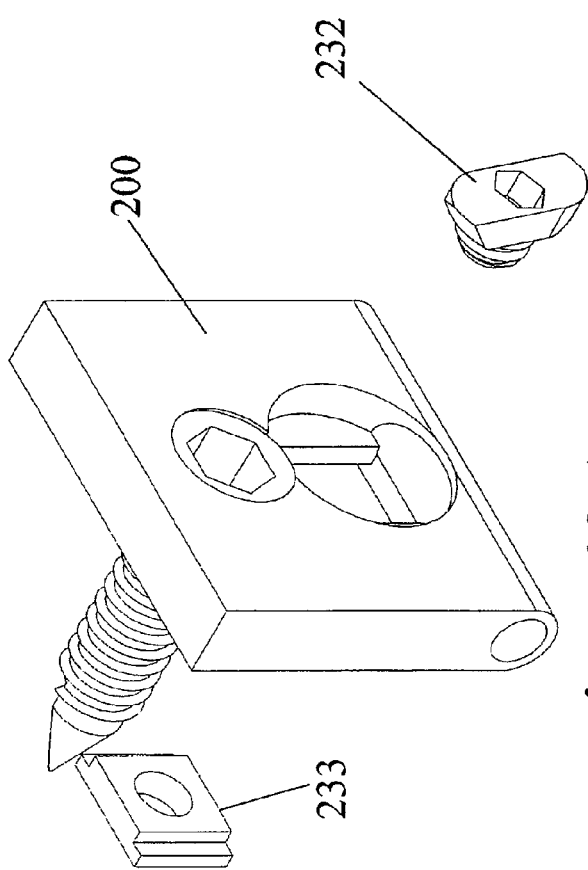

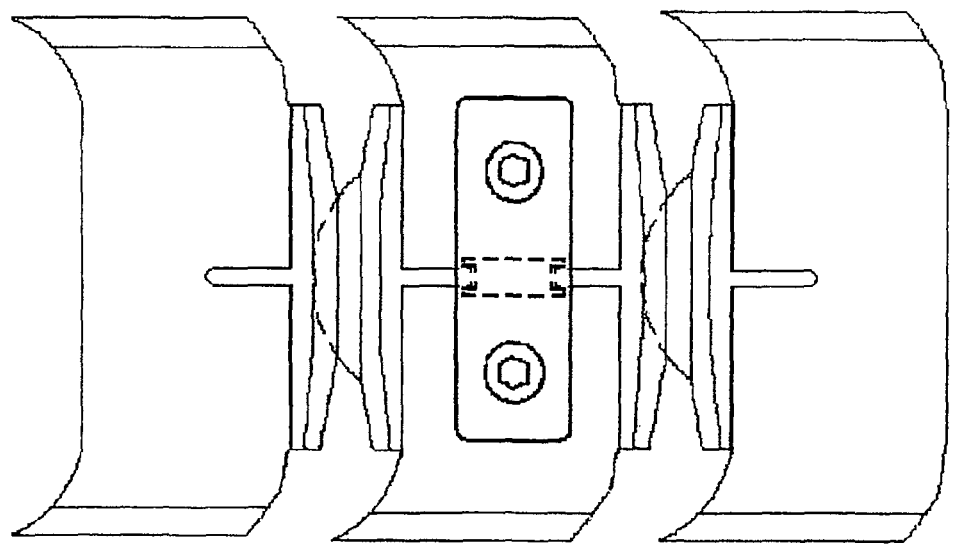
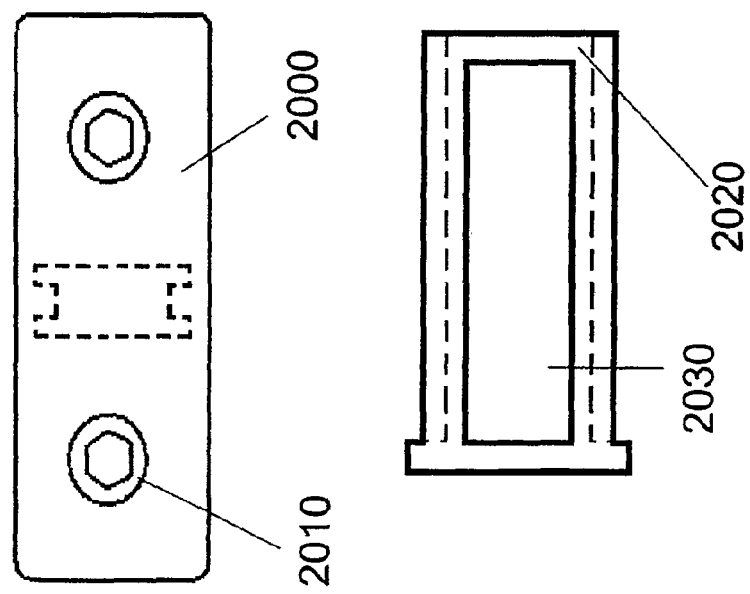

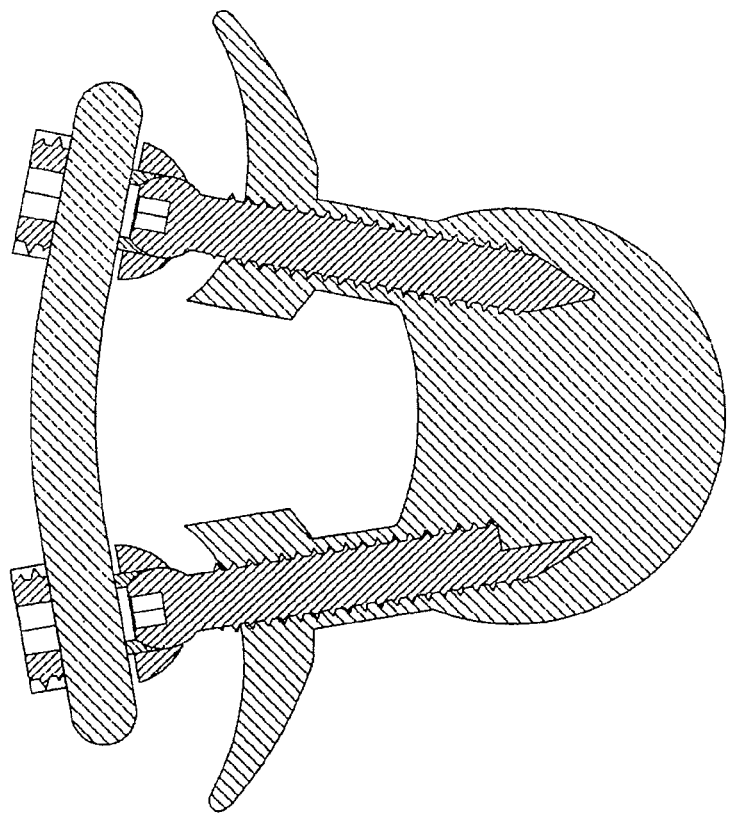
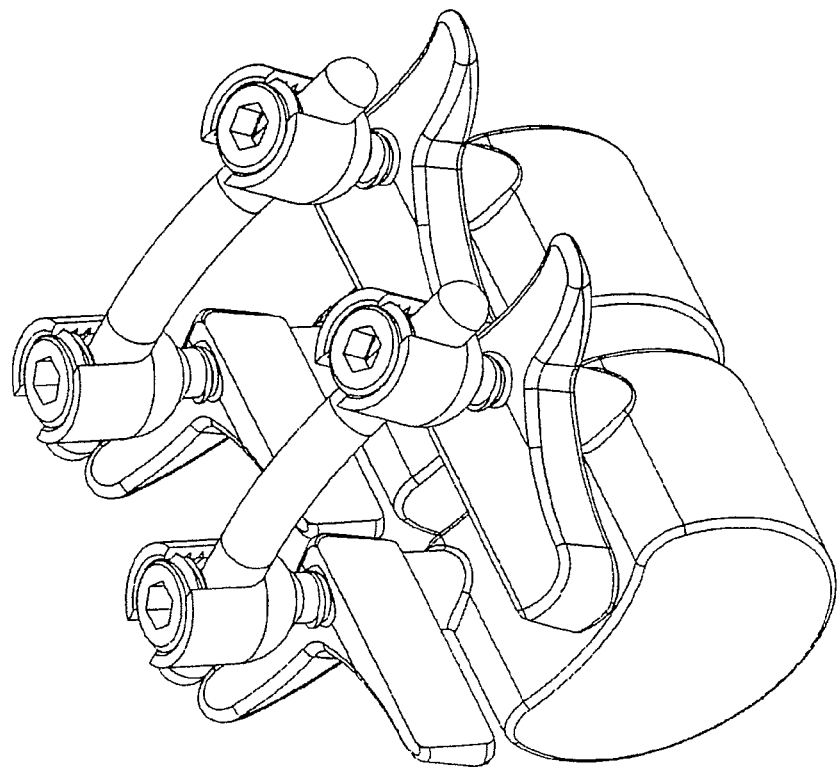
Fig. 74C

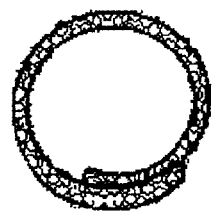
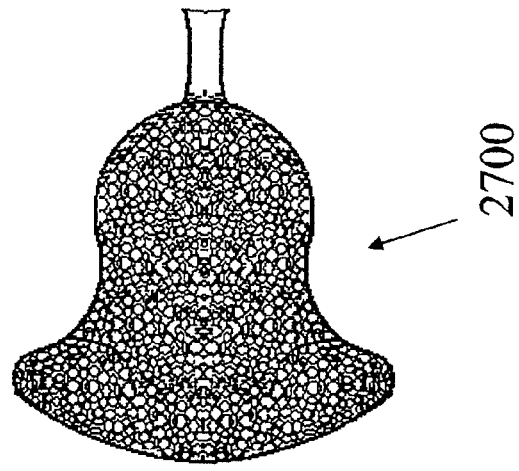
Fig. 78 B
Fig. 78 C
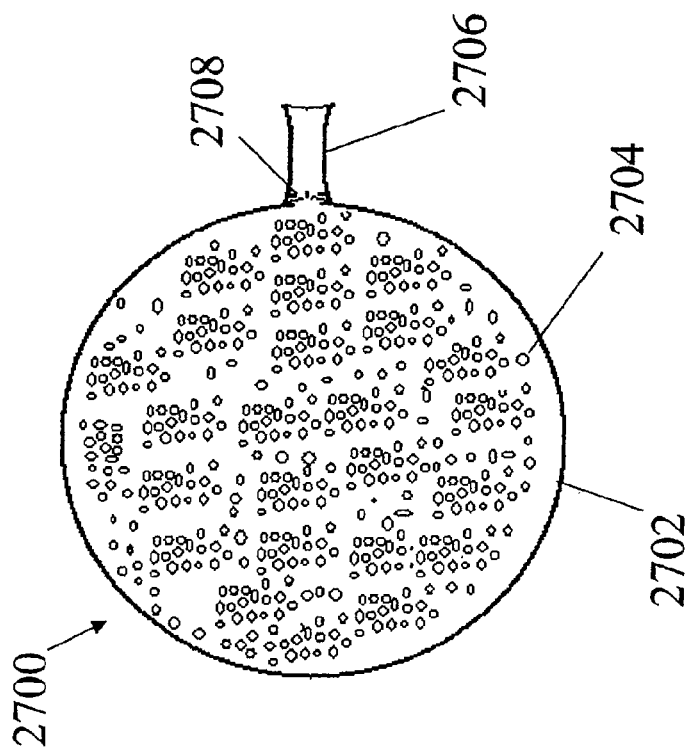
Fig. 78 A

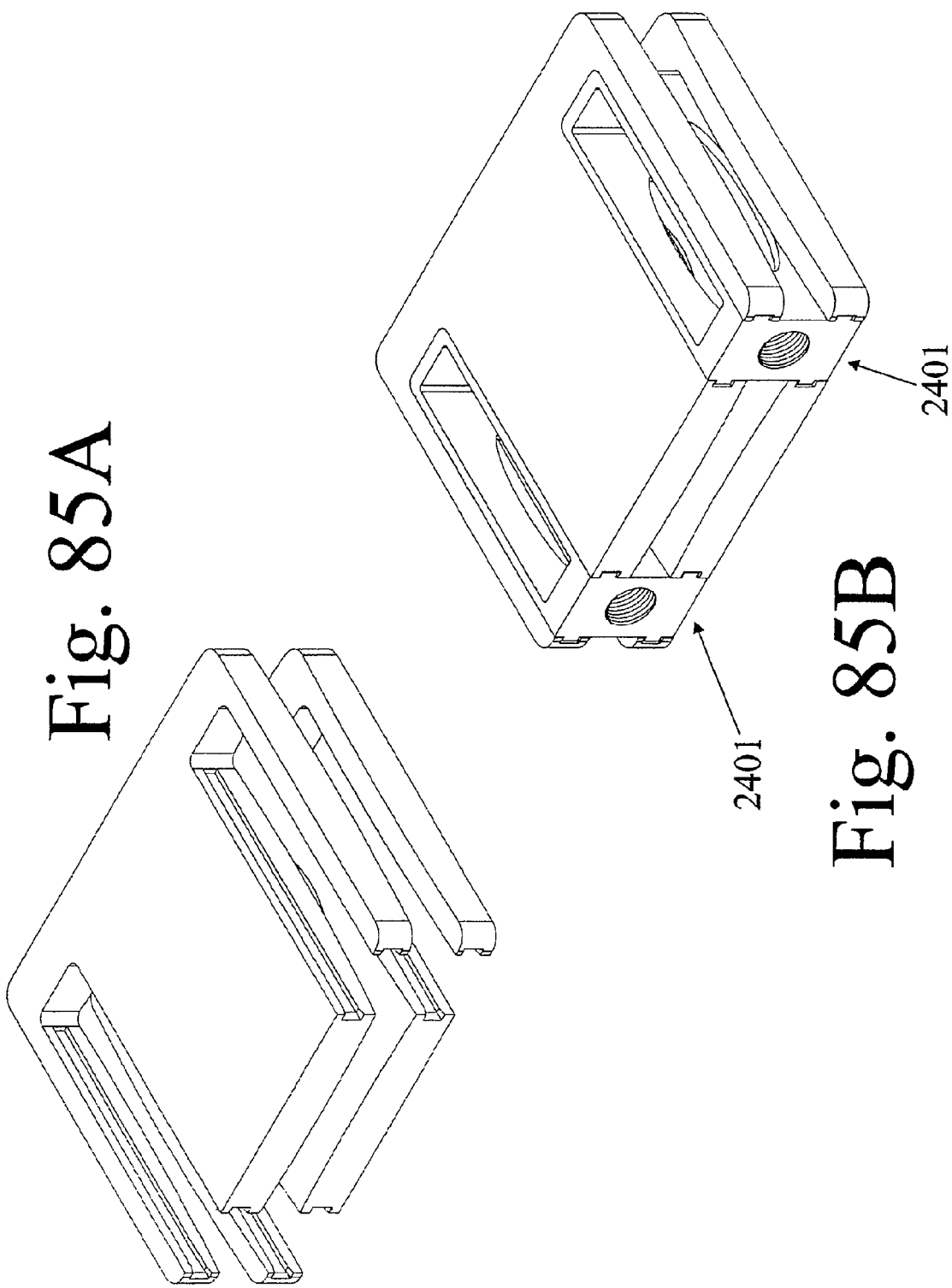

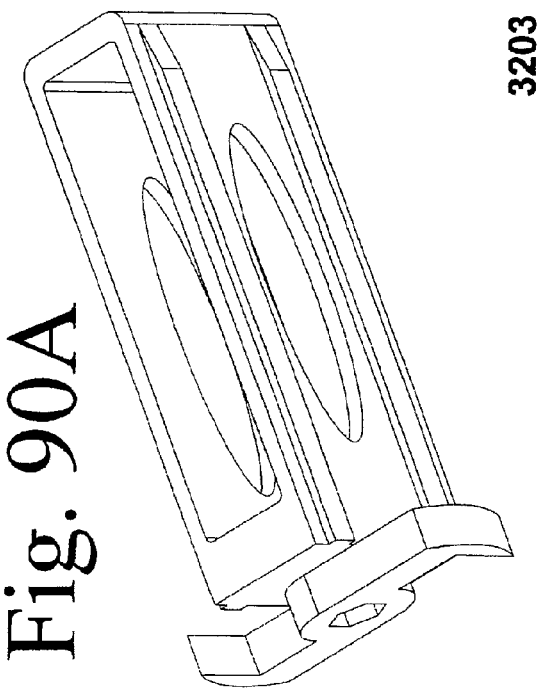
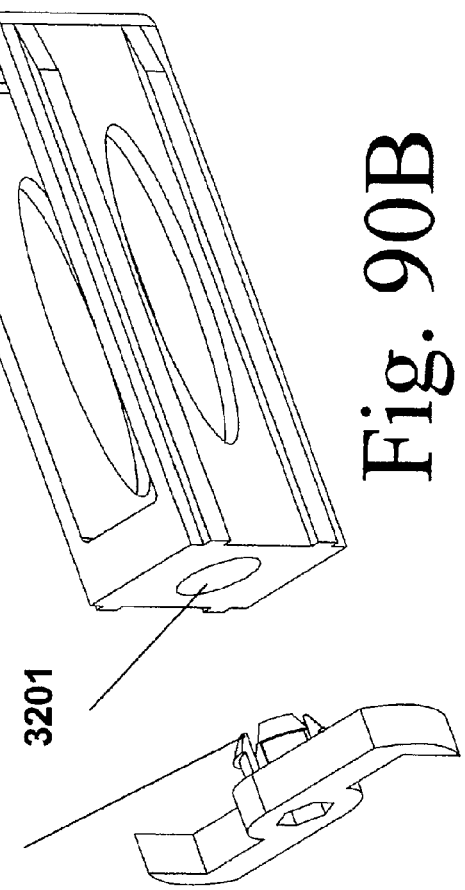
Fig. 90A
Fig. 90B

1

INTER-VERTEBRAL DISC MOTION DEVICES AND METHODS OF USE

REFERENCE TO PRIORITY DOCUMENT

This application claims priority of U.S. Provisional Patent Application Ser. No. 60/809,066, filed May 26, 2006, U.S. Provisional Patent Application Ser. No. 60/840,594, filed Aug. 28, 2006, U.S. Provisional Patent Application Ser. No. 60/850,473, filed Oct. 10, 2006, and U.S. Provisional Patent Application Ser. No. 60/878,612, filed Jan. 4, 2007. Priority of the aforementioned filing dates is hereby claimed and the disclosures of the Provisional Patent Applications are hereby incorporated by reference in their entirety.

BACKGROUND

Pain from degenerative spine disease is a major health problem in the industrialized world and the surgical treatment of spinal pathology is an evolving discipline. The traditional surgical treatment of a degenerating and painful inter-vertebral disc has been the complete immobilization and bony fusion of the involved spinal segment. An extensive array of surgical techniques and implantable devices have been formulated to accomplish this goal.

The growing experience with spinal fusion has shed light on the long-term consequences of vertebral immobilization. It is now accepted that fusion of a specific spinal level will increase the load on, and the rate of degeneration of, the spinal segments immediately above and below the fused level. As the number of spinal fusion operations have increased, so have the number of patients who require extension of their fusion to the adjacent, degenerating levels. The second procedure necessitates re-dissection through the prior operative field and carries significantly greater risk than the initial procedure while providing a reduced probability of pain relief. Further, extension of the fusion will increase the load on the motion segments that now lie at either end of the fusion construct and will accelerate the rate of degeneration at those levels. Thus, spinal fusion begets additional fusion surgery.

There is a growing recognition that segmental spinal fusion and complete immobilization is an inadequate solution to degenerative disc disease. Replacement of the degenerated and painful disc with a mobile prosthesis is a more intuitive and rational treatment option. This approach would permit preservation of spinal mobility in many patients with degenerative disc disease. Eventually, the degenerative process will progress sufficiently so that motion preservation with a mobile prosthesis is no longer possible. Those patients may be treated with fusion. That is, fusion and complete segmental immobilization is reserved for those patients with advanced degenerative disease where the spinal segment is beyond surgical reconstruction.

U.S. Pat. Nos. 4,759,769; 4,997,432; 5,674,294; 5,674,296; 5,676,701; 5,888,226; 6,001,130; 6,019,792; 6,162,252; 6,348,071; 6,368,350; 6,419,706; 6,520,996; 6,540,785; 6,607,558; 6,645,249; 6,673,113; 6,749,635 and many others have illustrated various artificial disc prosthesis. Despite the large number of proposed designs, several issues remain poorly addressed.

The cervical and lumbar spinal regions experience the greatest amount of degeneration and will be the most common recipients of artificial disc devices. However, the movement characteristics at these two anatomical regions are different. In the sagittal plane of cervical and lumbar spines, the motion of the upper vertebra onto the lower vertebra forms an actuate pathway with a center of rotation below the upper surface of the lower vertebra. Further, in the coronal plane of the lumbar spine, the motion of the upper vertebra onto the lower vertebra also forms an actuate pathway with a center of rotation below the upper surface of the lower vertebra. However, in the coronal plane of the cervical spine, the motion of the upper vertebra onto the lower vertebra forms an actuate pathway with a center of rotation above the lower surface of the upper vertebra.

Each spinal motion segment is composed of two adjacent vertebras and the articulations between them. These articulations include the anteriorly positioned inter-vertebral disc and the two posteriorly positioned facet joints. In the transfer of vertical force between adjacent vertebral bodies, the inter-vertebral disc caries approximately 80% of the load while the remaining 20% is borne by the facet joints. A predominate function of the facet joints is to limit the extent of rotation and forward translation between the adjacent bones.

Since the articulation between adjacent vertebral bones is composed of the inter-vertebral disc and two facet joints, any attempt at restoration of vertebral motion must address all three components of the articulation. Replacement of the painful disc with an artificial prosthesis will restore a more full range of motion to the segment and those patients with extensive degenerative disease of the facet joints will experience an increase in facet joint pain after artificial disc implantation because of the increased motion. For this reason, artificial disc placement is contraindicated in those patients with significant facet joint disease. Similarly, those with healthy facet joints at the time of implantation will develop pain as these joints degenerate over time. In fact, the rate of facet joint degeneration and the subsequent development of pain are emerging as major determinates of the clinical success of artificial disc replacement. That is, patient who undergoes artificial disc replacement to treat back pain will have re-emergence of the pain symptoms as the facet joints degenerate and the rate of joint degeneration will determine the time until symptom recurrence. Since the useful life of the prosthesis greatly exceeds the life expectancy of the degenerating facet joint, the rate of joint degeneration becomes the true determinate of the pain-free interval that resides between the time of prosthesis implantation and the time of pain recurrence. The pain-free interval is a prominent statistic in the overall determination of clinical success of these operations.

The design of the implanted disc prosthesis can significantly influence the rate of facet joint degeneration. As expected, a disc prosthesis that significantly loads the facet joints will accelerate the rate of joint degeneration and shorten the pain-free interval. Biomechanical studies have shown that the stress forces inside the facet joints tend to be highest when rotational forces are applied to the motion segment. Prosthetic discs that increase the extent of rotational freedom necessarily increase the load on the facet joints. Further, extreme extension of the motion segment will cause the two joint surfaces to "bottom out" and forcefully abut one another which also increase the rate of joint degeneration. Finally, ball-in-socket device designs with a fixed center of rotation and a large ball radius can produce significant anterior translation of the upper vertebral body with flexion and cause pronounced loading of the facet joints. Conversely, devices with a small ball radius can produce significant facet joint abutment in flexion and an increase in the rate of joint degeneration. Hence, despite advances in implant design, there remains a need in the art for improved implants.

SUMMARY

Accordingly, provided herein are implants that address the aforementioned issues. Multiple artificial disc embodiments are described herein. The implant designs replicate physiologic movement and minimize the stress loads on the facet joints. Some embodiments limit the extent of rotational movement and/or distract the facet joints with movement to reduce the likelihood of aberrant joint surface contact and thereby decrease the rate of joint degeneration. Unique methods of prosthesis attachment onto the vertebral bones are also disclosed. Devices and methods for the conversion of a mobile prosthesis into a fusion device are also discussed. In addition, devices and methods for the repair of vertebral fractures adjacent to the mobile disc device are disclosed.

In one aspect, provided herein is an orthopedic prosthesis, comprising: at least one mobile device adapted to at least partially replace the motion characteristics of a natural inter-vertebral disc positioned in a disc space; and a receptacle coupled to a bearing surface, the receptacle being adapted to accept an implantable material without the removal of the bearing surface, wherein the implantable material contacts the abutment surface of each of the vertebral bodies adjacent to the disc space and leads to fusion and immobilization of two vertebral bodies adjacent the disc space.

In another aspect, provided herein is a method for the correction of vertebral scoliosis without bone fusion using a minimally invasive surgical technique, comprising: laterally approaching a side of a convexity of a deformity in the spine, wherein the side of the convexity is a side of the vertebral midline in which the vertical distance between the pedicle portion of each vertebral body of the spine is greatest; and placing a mobile orthopedic prosthesis into a disc space via the lateral approach, wherein the orthopedic prosthesis contains at least one bearing surface that is adapted to at least partially replace a natural inter-vertebral disc, wherein the dimension of the prosthesis in the coronal plane is less than that of the inter-vertebral disc.

In another aspect, provided herein is a method of repairing and augmenting a fractured vertebral body that abuts an implanted mobile disc prosthesis without fusion to another vertebral body, comprising: placing a rigid orthopedic brace across a fracture site and anchoring the brace to bone using bone fasteners on either side of the fracture site, wherein the brace contains at least one rigid member; and preserving the mobility of a natural disc or mobile disc prosthesis that abuts the fractured vertebra.

In another aspect, provided herein is an orthopedic prosthesis, comprising: a mobile device that is adapted to at least partially reproduce the motion characteristics of a natural cervical inter-vertebral disc by at least partially replacing an unco-vertebral joint portion of a natural cervical disc without concurrently replacing a portion of the body of the disc that is interposed between each of the two unco-vertebral joints of that disc.

Other features and advantages should be apparent from the following description of various embodiments, which illustrate, by way of example, the principles of the invention.

DESCRIPTION OF THE FIGURES

FIG. 2 shows additional views of the prosthesis of FIG. 1.
FIGS. 3A and 3B show exploded views of the prosthesis of FIG. 1.
FIGS. 4A and 4B show coronal cross-sectional views of the assembled prosthesis.
FIGS. 5A and 5B show sagittal cross-sectional views of the assembled prosthesis.
FIGS. 6A-10 show an exemplary method of implanting the prosthesis.
FIG. 12 shows an enlarged view of rotatable fixation
FIGS. 19A and 19B show exploded views of the prosthesis of FIG. 18.
FIGS. 20A and 20B show coronal cross-sectional views of the prosthesis of FIG. 18.
FIG. 24 shows transparency views of the prosthesis of FIG. 23.
FIG. 28 shows another embodiment of the prosthesis.
FIGS. 29A and 29B illustrate another embodiment of a prosthesis.
FIGS. 34A and 34B illustrate partially exploded views of another device embodiment that is sized and shaped to be positioned within an inter-vertebral disc space, wherein the natural disc has been at least partially evacuated.
FIG. 37A show cross-sectional views of the prosthesis.
FIG. 37B shows a protrusion that resides within anterior indention when the device is in a first, closed configuration.
FIG. 37C shows the prosthesis in the second, open configuration with protrusion in the posterior indentation.

FIGS. 40A-41B illustrate exemplary curved contoured surfaces.

FIG. 44 shows another embodiment of a prosthesis.

FIGS. 47A to 47C illustrate the interactions of the protrusion and indentation during different stages of flexion/extension.

FIGS. 50A and 50B show exploded views of the prosthesis of FIG. 49.

FIG. 51 shows cross-sectional views of the prosthesis of FIG. 49.

FIGS. 53A-53C show another embodiment wherein one member has a toroid articulation surface and the other member uses a segment of a cone as its articulation surface.

FIG. 54 shows another embodiment of a prosthesis.

FIGS. 55-58 show additional prosthesis embodiments.

FIG. 61 shows another embodiment of a prosthesis.

FIGS. 68A and 68B illustrate partially exploded views of a member with a rotatable member and its complimentary attachment member.

FIG. 73A shows perspective views of an additional embodiment of a prosthesis.

FIG. 73B shows the device of FIG. 73A attached to the fractured vertebral body with the artificial disc prosthesis in place.

FIGS. 74A, 74B and 74C illustrate alternative embodiments of a device used to repair the vertebral fracture(s) while retaining the prosthetic disc devices.

FIGS. 78A-78C illustrate an additional embodiment of a prosthesis. FIG. 78C illustrates a central corridor that can be used to perform the surgical procedure.

FIG. 85A illustrates an embodiment of a disc prosthesis device prior to insertion of the bone cage.

FIG. 85B shows the prosthesis after a single bone cage has been placed within the openings on each side of the midline.

FIGS. 90A and 90B show a bone anchor connected to and disconnected from the bone cage.

DETAILED DESCRIPTION

Figure 1:
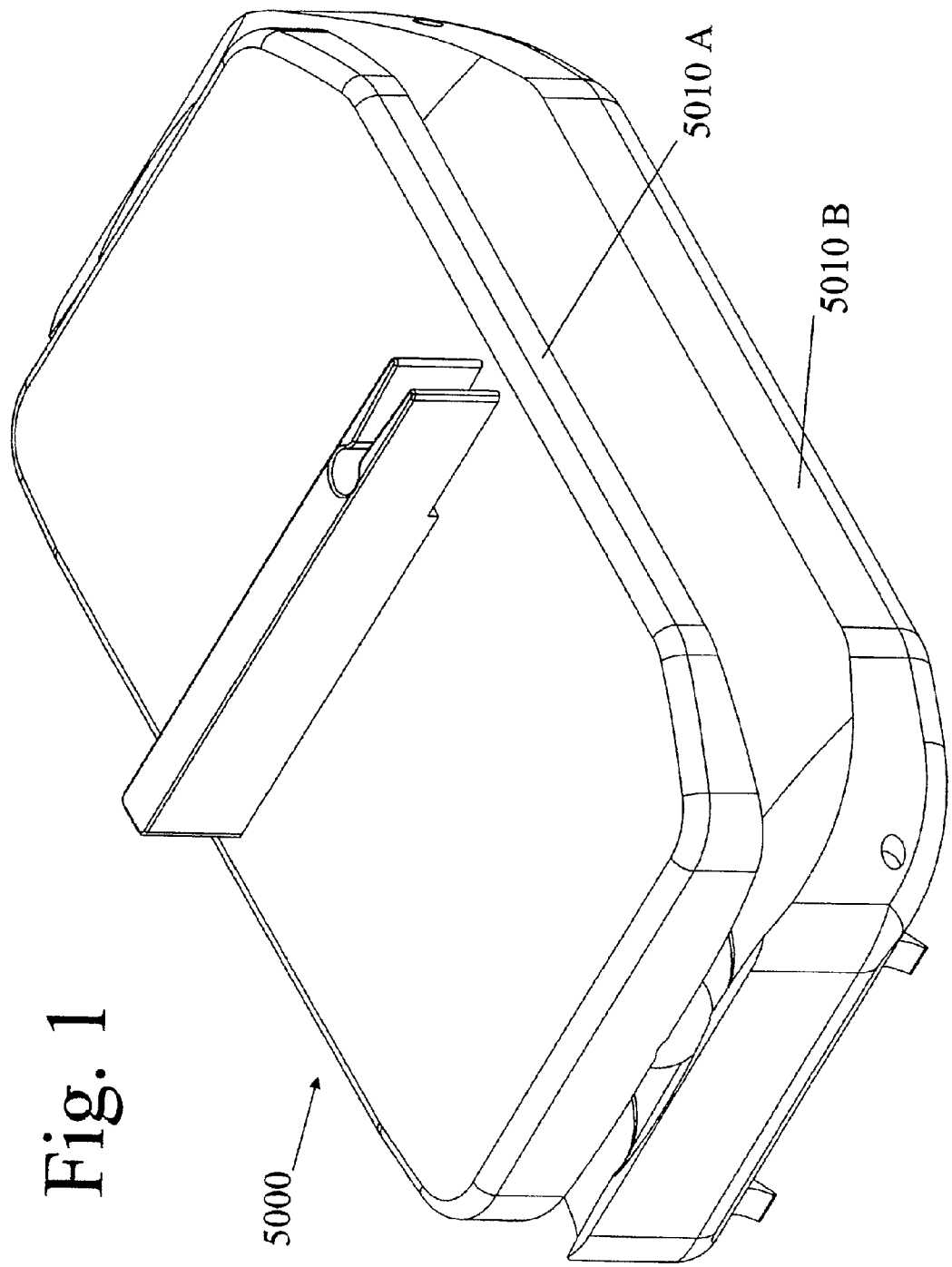
FIG. 1 illustrates a perspective view of an artificial disc prosthesis.
Figure 8B:
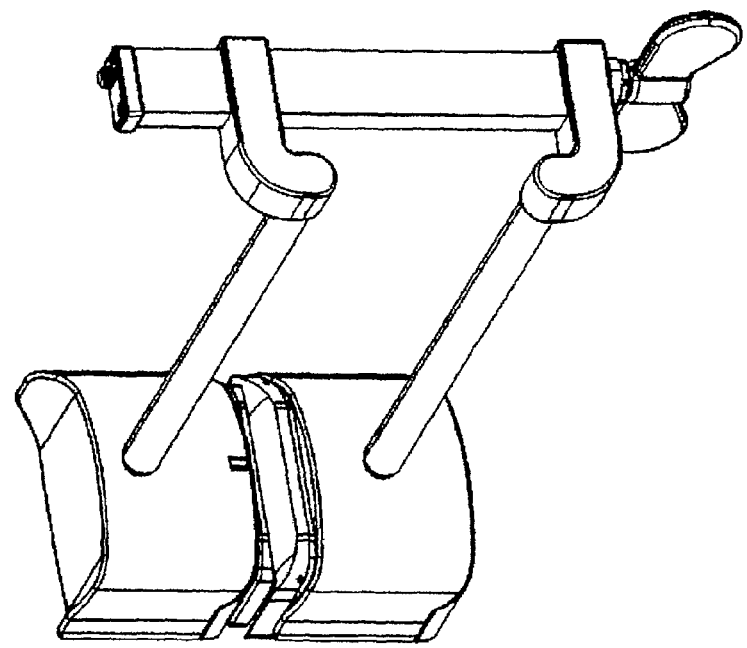
Figure 8A:
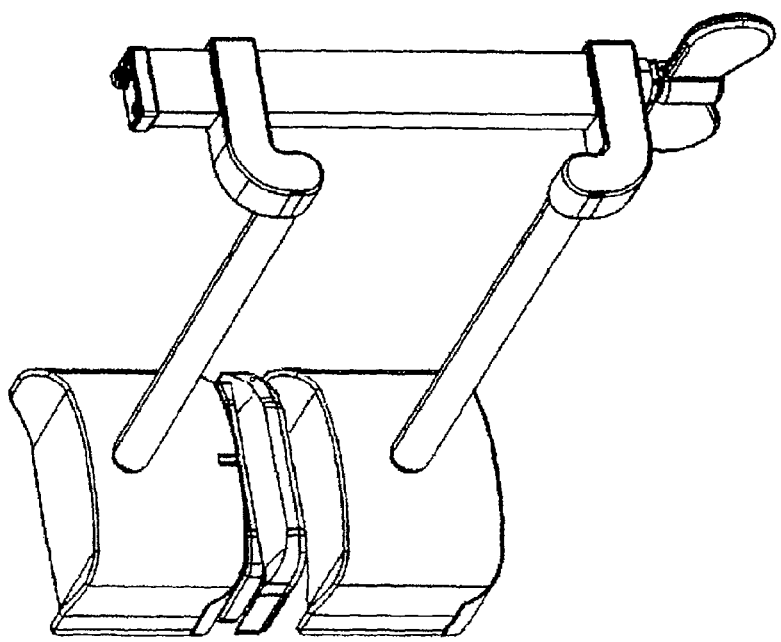
Figure 9B:
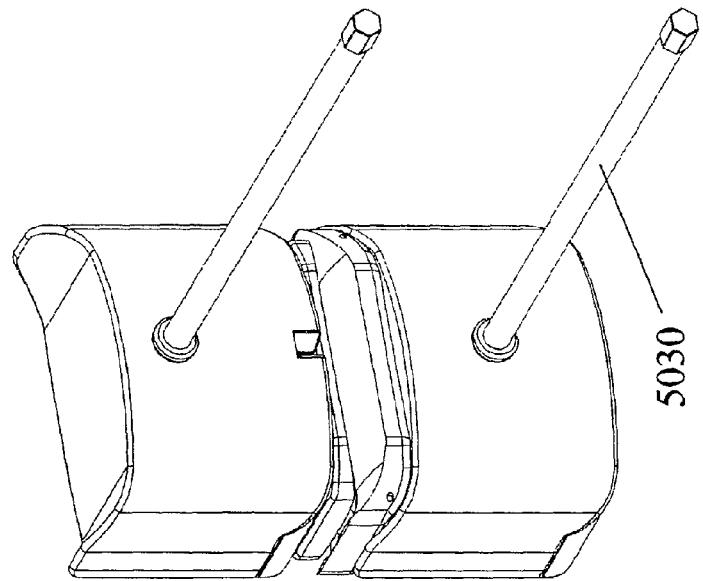
Figure 9A:
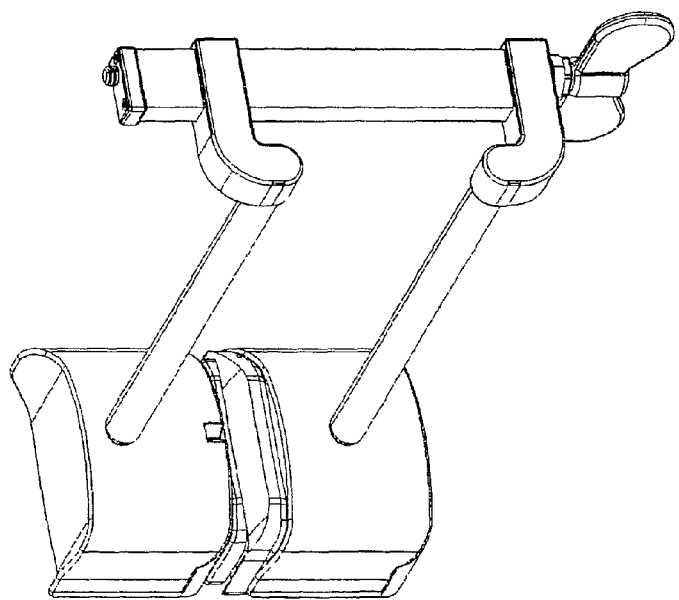

FIG. 1 illustrates a perspective view of an artificial disc prosthesis 5000 while FIG. 2 show multiple additional views. Exploded views of the device are shown in FIGS. 3A and 3B. The device is made up of a superior member 5010A and an inferior member 5010B that are joined together by spring member 5020. The spring is integrally attached to the upper member and attached to lower member 5010B by coupling with threaded locking cap 5021. The spring is preferably a precision machined spring. An articulation exists between the two members 5010 and permits movement between them.

After removal of a diseased inter-vertebral disc, the device is placed within the evacuated disc space and replaces the function of a natural inter-vertebral disc. The top surface of upper member 5010A abuts the lower surface of the upper vertebra while the bottom surface of the lower member 5010B abuts the upper surface of the lower vertebra. The bone-abutting surfaces may be further textured to increase bone contact and/or coated with osteo-conductive (such as demineralized bone matrix, hydroxyapatite, and the like) and/ or osteo-inductive (such as Transforming Growth Factor "TGF-B," Platelet-Derived Growth Factor "PDGF," Bone-Morphogenic Protein "BMP," and the like) bio-active materials that promote bone in-growth, bone formation, or establish a mineralized connection between the bone and the implant. They may be also directly made of materials known to promote bone formation.

At least one spherical protrusion 5015 descends from the inferior aspect of upper member 5010A and forms the articulation surface of that member. Lower member 5010B has a cut-out 5023 with end segments 5025 wherein segments 5025 form the articulation surface of the lower member. Segments 5025 are portions of a cone that is centered about the center line of bore hole 5028. Coronal cross-sectional views of the assembled device are shown in FIGS. 4A and 4B. Sagittal cross-sectional views of the assembled in are shown in FIGS. 5A and 5B.

The articulation formed between member 5010 permits movement in the sagittal (anterior-posterior) plane with a curved pathway that has center of rotation along a line connecting the contact points between spherical members 5015 and end segments 5025. It permits movement in the coronal plane with a center of rotation at a point above the articulation surfaces. Rotational movement in the axial plane of member 5010A relative to member 5010B is permitted within confines of conical end segments 5025. Movement within these planes is partially resisted by the action of spring member 5020. Member 5020 acts to return the device to a neutral position after movement. These motion characteristics collectively replicate the movement profile of a natural cervical spine disc and this embodiment is well suited for cervical disc replacement.

Figure 10:
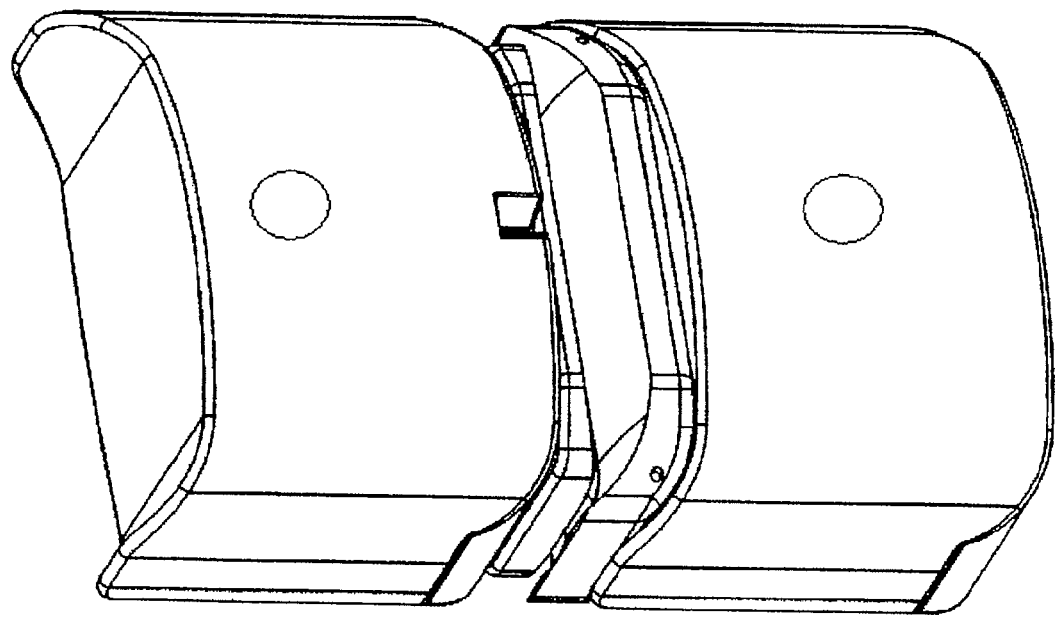

FIGS. 6A-10 illustrate a placement method. In FIG. 6A, distraction screws 5030 are placed into the vertebral bodies above and bellow the disc space to be implanted. The screws are preferably placed in the midline of the coronal (right to left) plane. Removal of the diseased disc material may be performed before placement of the distraction screws but the procedure is simplified when the distraction screws are placed before the evacuation of the disc space. After the disc has been removed and the disc space have been prepared, a cut is made in the coronal midline of the inferior aspect of the upper vertebral body, as shown in FIG. 6B. FIGS. 7A and 7B illustrate placement of a distractor onto the distraction screws and its use in the separation of the vertebral bodies before implant placement. (In actual practice, the distractor will have been already placed during disc removal.) In FIG. 8A, the prosthesis is placed into the evacuated disc space with keel 5034 aligned with the previously-made bony cut. The force of distraction is removed by closing the distractor and allowing the prosthesis to forcefully abut the superior aspect of the lower vertebral body (FIG. 8B). The rotatable fixation pins 5039 that are positioned within the inferior aspect of the implant are forcibly rotated and driven into the inferior vertebral body, as discussed below. In FIG. 9A, members 5033 of the split end of keel 5034 are separated in order to fixate and secure the device within the upper vertebral body (separation device not shown). The distractor and distraction screws 5030 are removed as shown in FIGS. 9B and 10, respectively.

Figure 11:
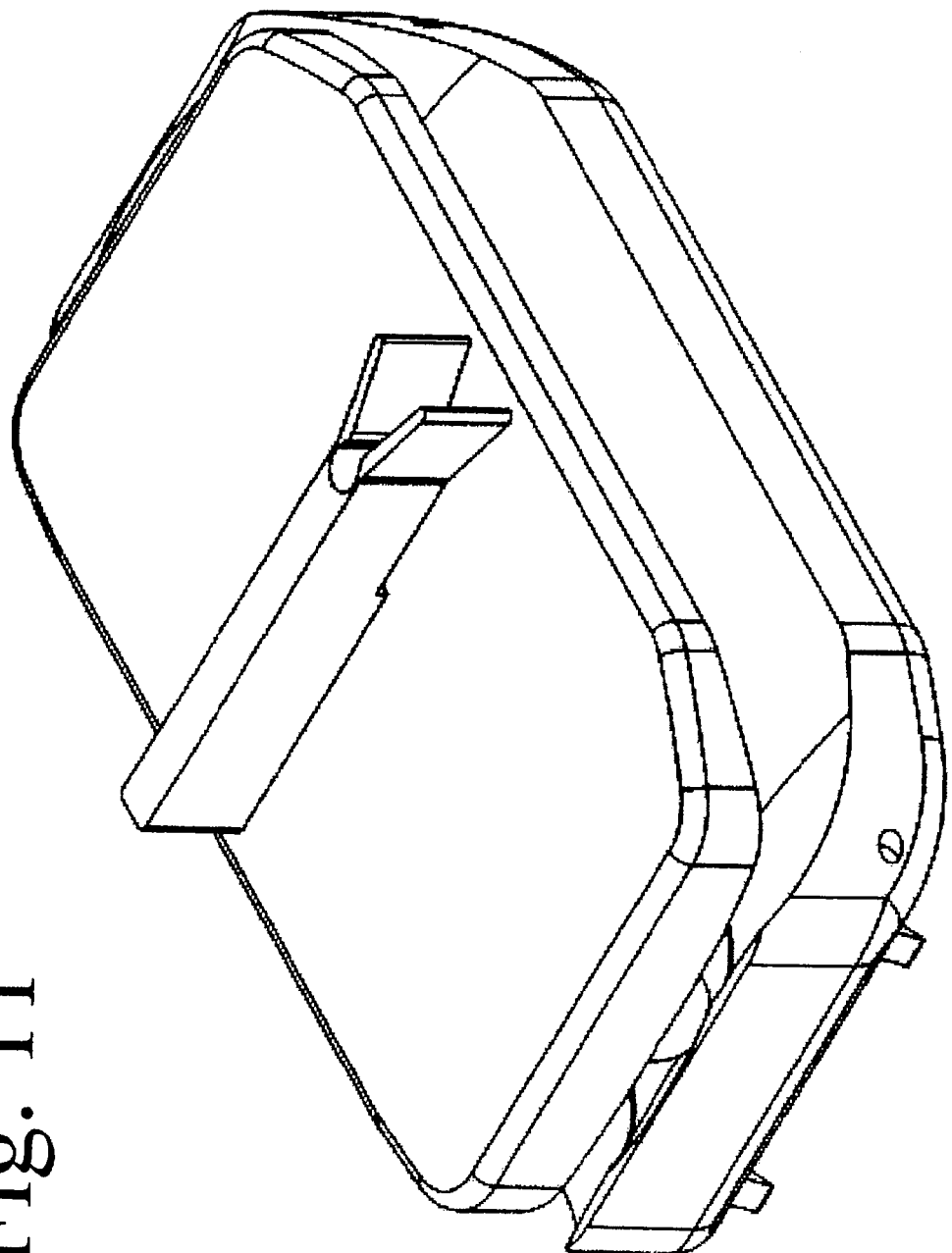
FIG. 11 shows the implanted prosthesis without the vertebral bones
Figure 13A:
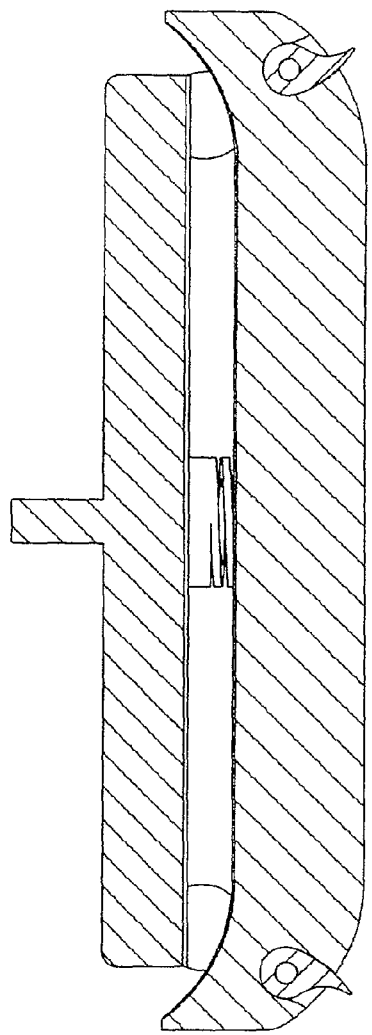
FIG. 13A shows a coronal cross-sectional view of the prosthesis before pin rotation
Figure 13B:
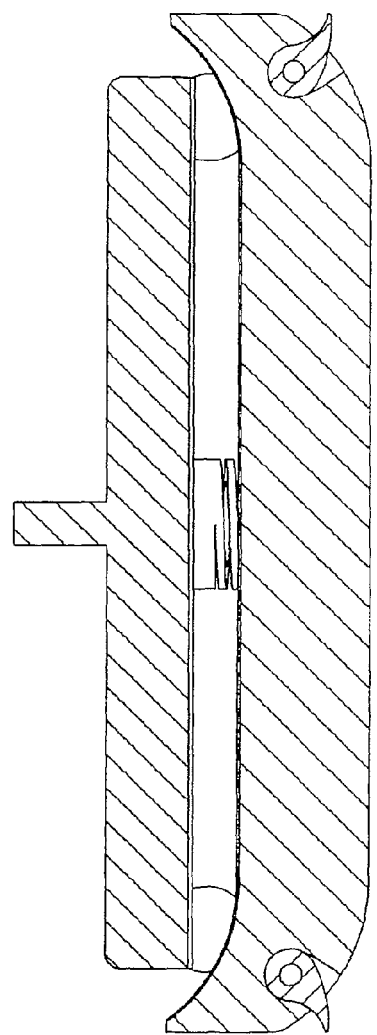
FIG. 13B shows a similar view as FIG. 13A after pin rotation.

The implanted device is illustrated without the vertebral bones in FIG. 11. The separated members 5033 of the end of the split keel 5034 are shown and, as noted, this feature increases the extent of device fixation into the vertebral bone. In FIG. 12, the rotatable fixation pins 5039 are shown. Removal of the distraction force after device implantation (FIG. 8B) forcibly drives the pins into the unco-vertebral portion of the superior aspect of the lower vertebral body. Pin anchoring within the vertebral bone is enhanced by the outward rotation of the pins in reaction to the vertical load. FIG. 13A shows a coronal cross-sectional view of the device before pin rotation while FIG. 13B shows a similar view after pin rotation. This feature will further increase the extent of device fixation into the underling bone. Moreover, normal upright patient activity and movement within the post-operative period will further drive the pins into bone.

Figure 14:
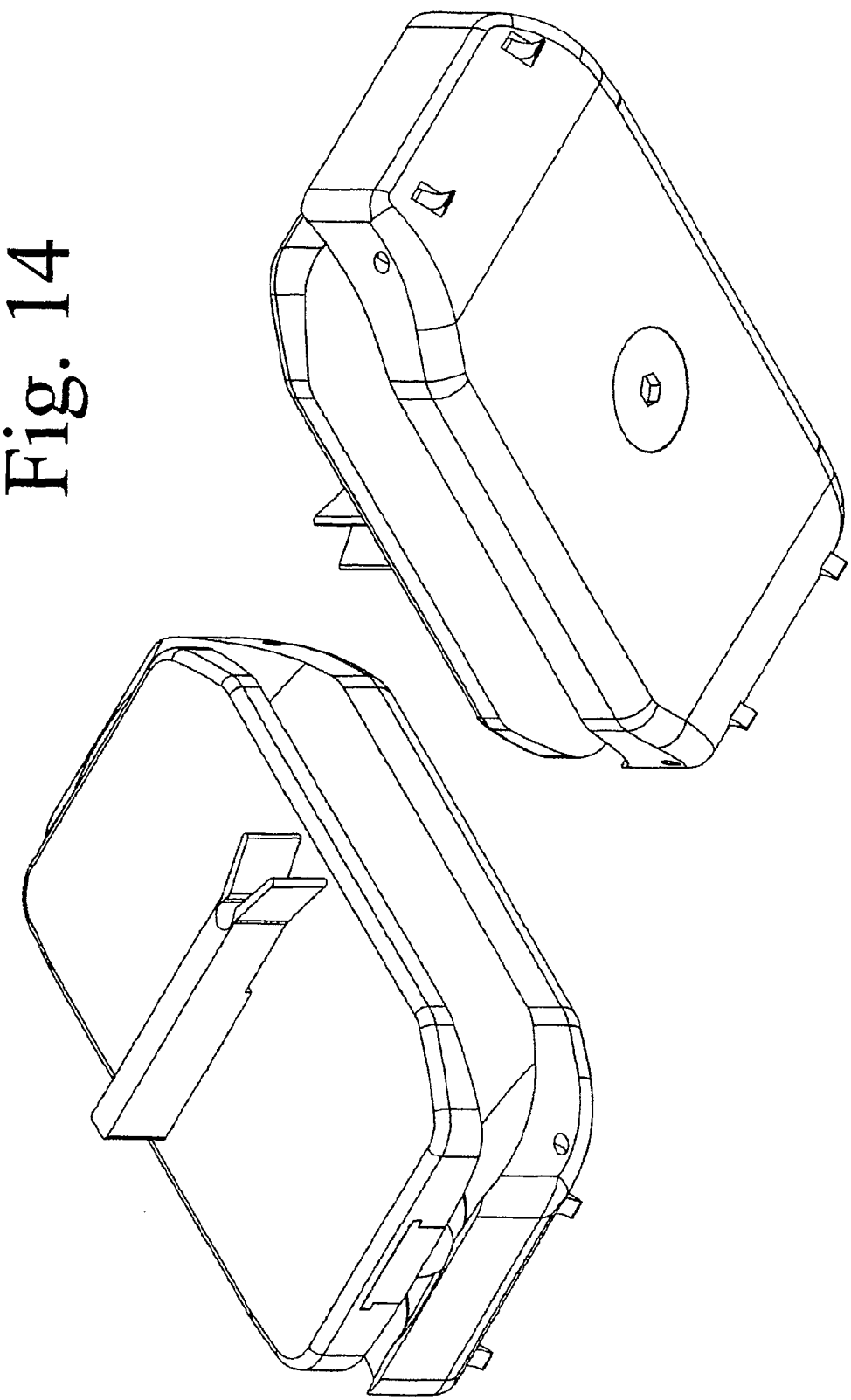
FIG. 14 shows an alternative embodiment of the prosthesis.
Figure 15B:
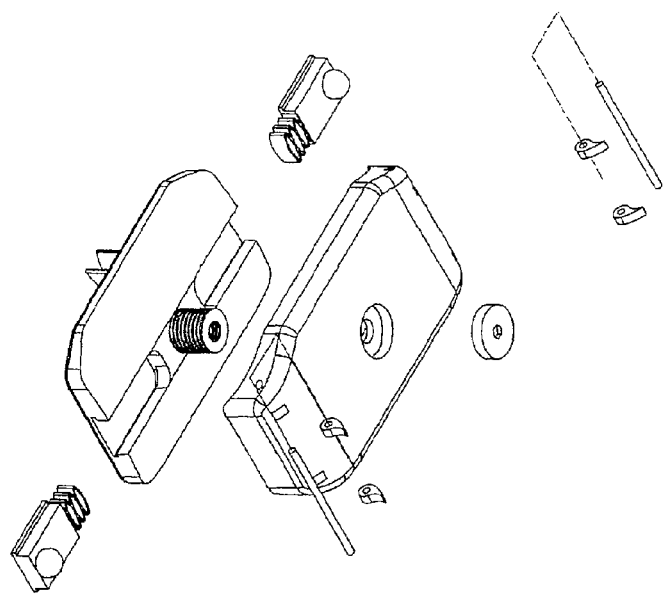
FIGS. 15A and 15B show exploded views of the prosthesis of FIG. 14.
Figure 15A:
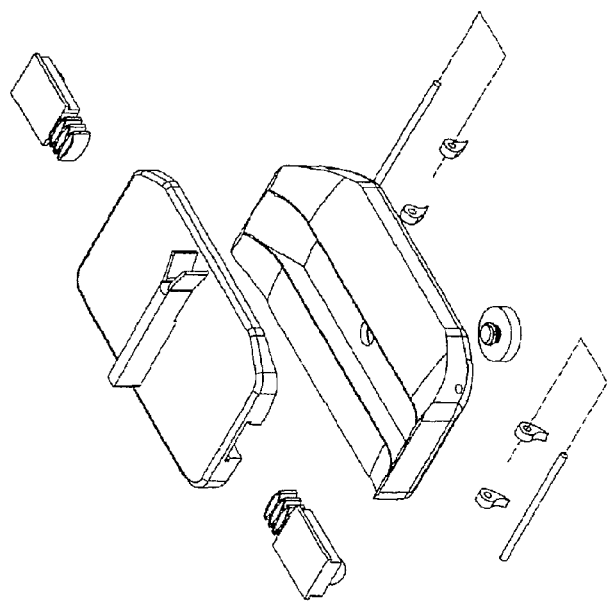

A second prosthesis embodiment is shown in FIG. 14. Exploded views are illustrated in FIGS. 15A and 15B. In the prior embodiment, the device had no specific mechanism capable of dampening the fluctuations in vertical load. That is, the implant transmitted the vertical load from the upper to lower vertebra with no specific feature that would function as a "shock absorber". Since the native inter-vertebral disc has a dampening effect on an applied vertical load, the current embodiment contains a feature that would replicate this property. The lower member 5010B is unchanged from the prior embodiment. The upper member 5010A contains cut-outs 5042. Member 5045 has spherical extension 5048 which functions as an articulation surface with lower member 5010B. Member 5045 also has a malleable feature 5060 on one end. While depicted as an integral spring member, malleable feature 5060 may be alternatively made of an elastomer or it may be comprised of any other integral or separate substance and/or mechanism that is adapted to function as a malleable member.

Figure 16A:
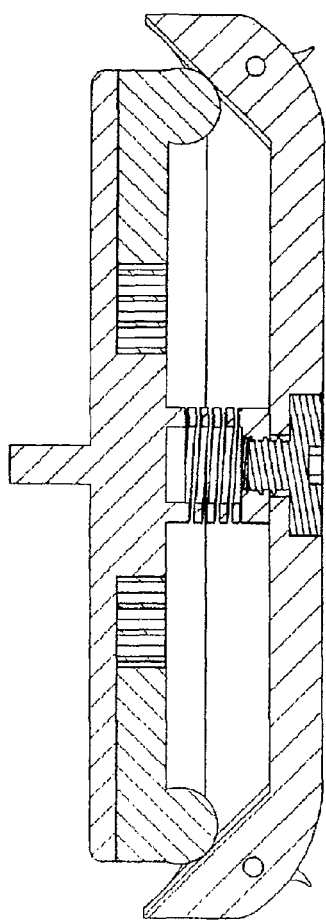
FIGS. 16A and 16B illustrate cross-sectional views of the assembled prosthesis in the coronal plane.
Figure 16B:
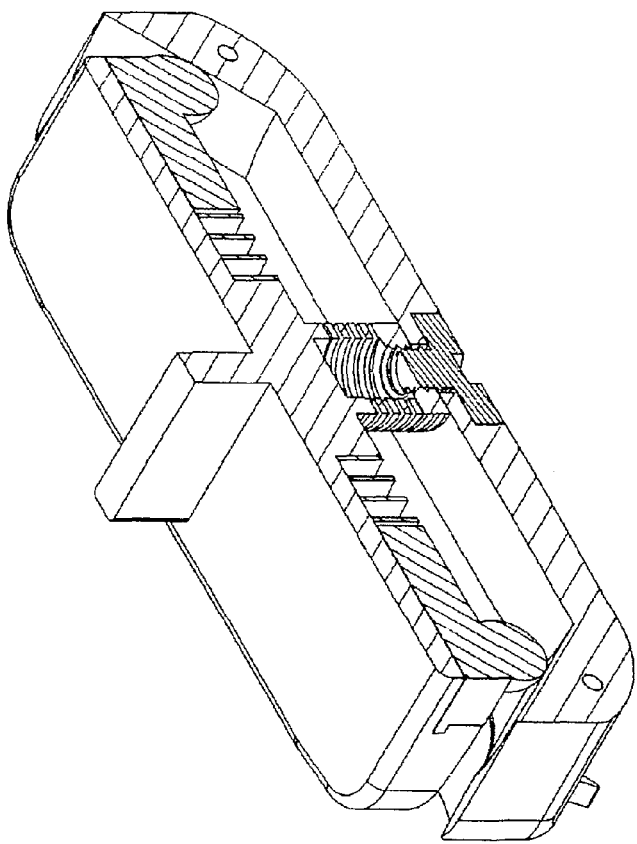
Figure 17A:
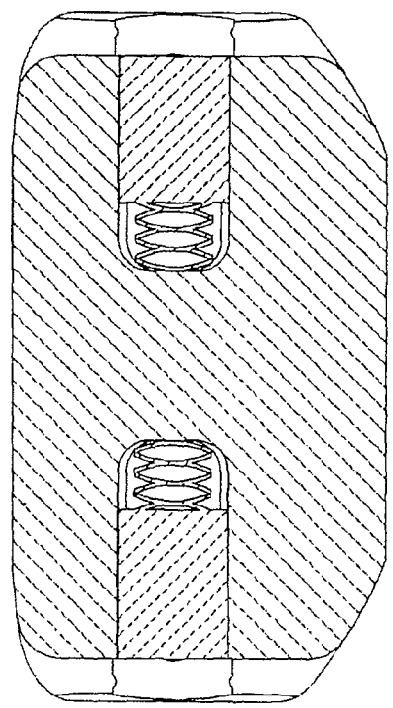
FIGS. 17A and 17B show axial cross-sectional views of the prosthesis.
Figure 17B:
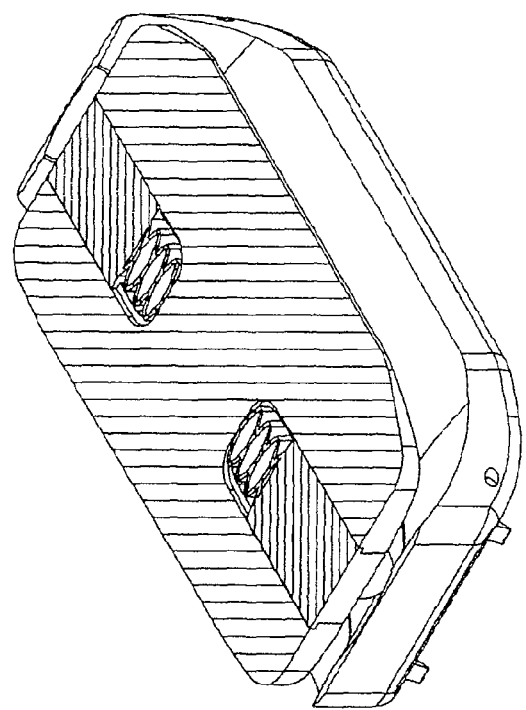

FIGS. 16A and 16B illustrate cross-sectional views of the assembled device in the coronal plane. Axial cross-sectional views are shown in FIGS. 17A and 17B. Application of a vertical force onto the implant produces the inward migration of member 5045 within cut-out 5042 on each side of the implant. Movement of member 5045 within cut-out 5042 is resisted by malleable members 5060. Thus, the prosthesis is capable of dampening the effect of a vertical load by the action of a malleable member in a non-vertical plane. Given the limited vertical dimensions of the disc space, this feature provides a significant design advantage and allows the prosthesis to more perfectly replicate the properties of the natural disc.

Figure 18:
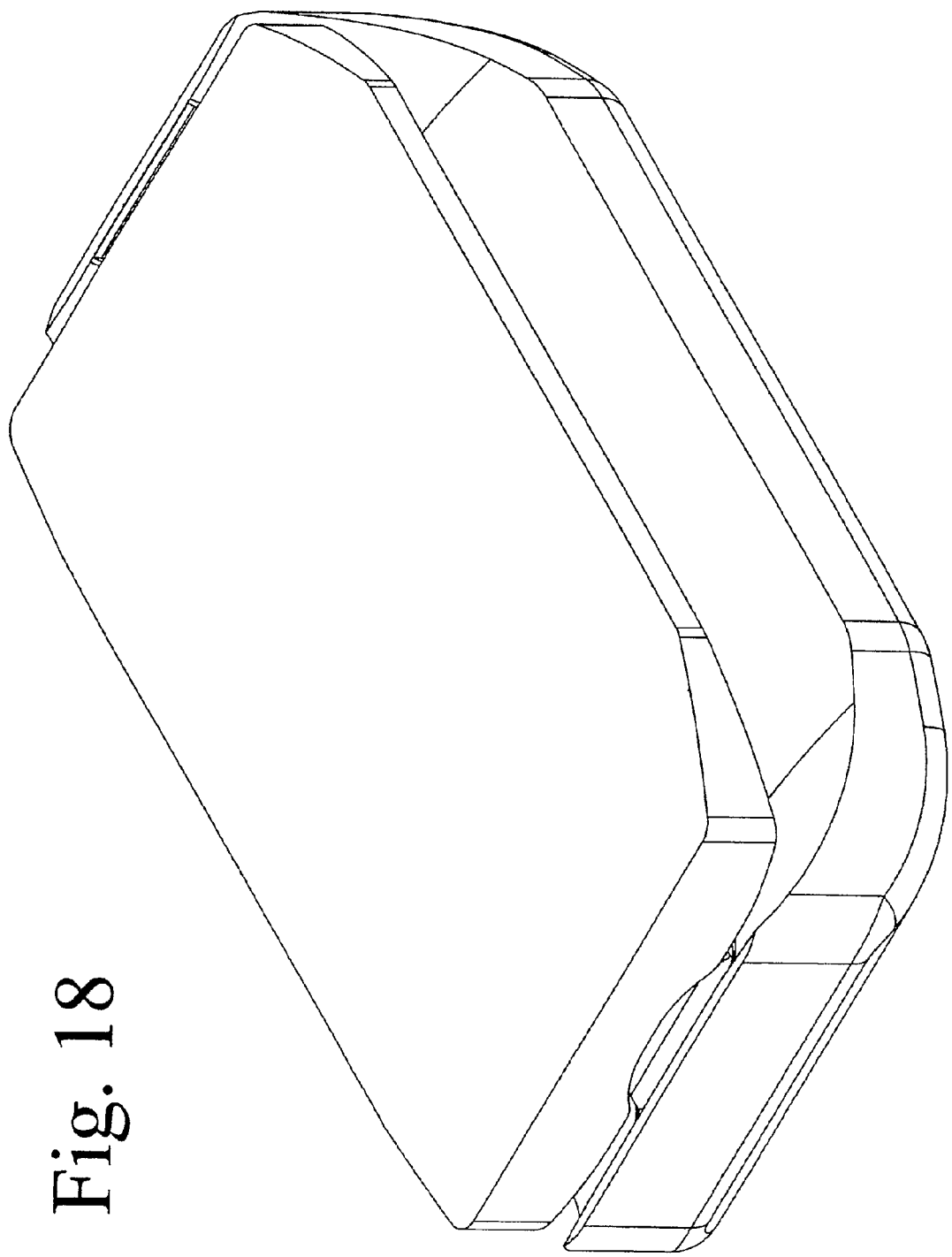
FIG. 18 shows an alternative embodiment of the prosthesis.

Another embodiment is shown in FIG. 18 while exploded views are illustrated in FIGS. 19A and 19B. The present embodiment is similar to the first embodiment but incorporates two sets of articulation surfaces. The expandable keels and rotatable bone pins have been omitted for diagrammatic simplicity. In this embodiment, the articulation surface 5025 of lower member 5010B is an inclined plane. Upper member 5010A contains cylindrical cut-out 5062 with end protrusions 5063. Middle member 5010C contains cylindrical protrusions 5065, wherein the long axis of each protrusion is in the sagittal (anterior-posterior) plane. The protrusions 5065 articulate with inclined plane surface 5025 of lower member 5010B to form the inferior articulation. Preferably, cylindrical protrusions 5065 are of lesser anterior-to-posterior length than the anterior-to-posterior length of surfaces 5025, allowing some anterior/posterior translation of the two surfaces relative to one another. The superior aspect of the middle member 5010C is a cylindrical surface 5070 with its long axis in the coronal (right to left) plane. The cylindrical surface 5070 of the middle member 5010C articulates with the cylindrical cut-out 5062 of the upper member 5010A to form the superior articulation. Preferably, the radius of the cylindrical surface 5070 is slightly less than that of cylindrical cut-out 5062. Also, the length of cylindrical surface 5070 in the coronal (side-to-side) plane is slightly less than that of cut-out 5062. These differences permit additional rotational and translational movement between the cylindrical surface 5070 and cut-out 5062.

Figure 21:
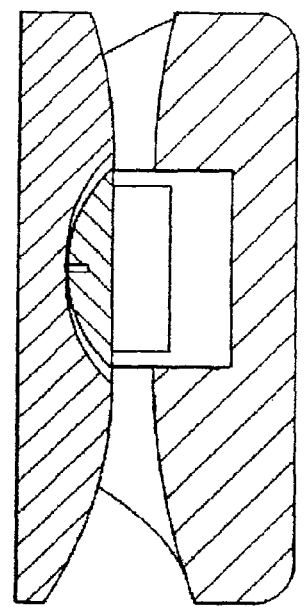
FIGS. 21A and 21B show sagittal cross-sectional views of the prosthesis of FIG. 18.
Figure 21:
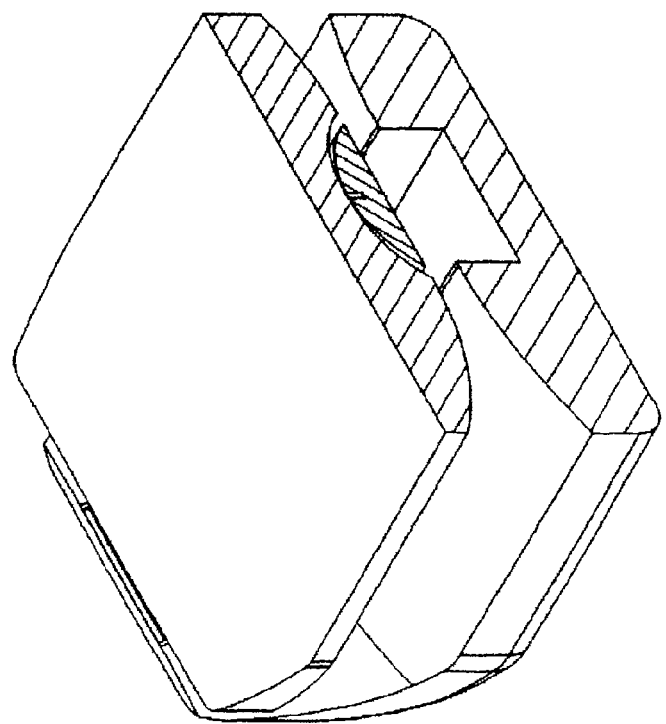
Figure 22A:
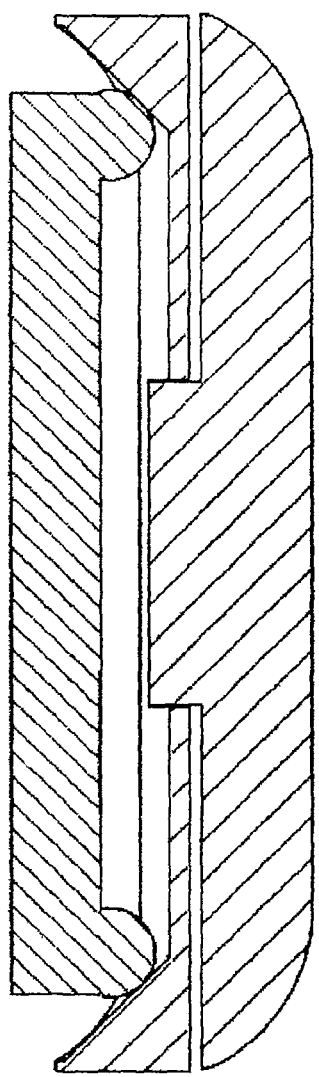
FIGS. 22A and 22B show additional embodiments of the prosthesis.
Figure 22B:
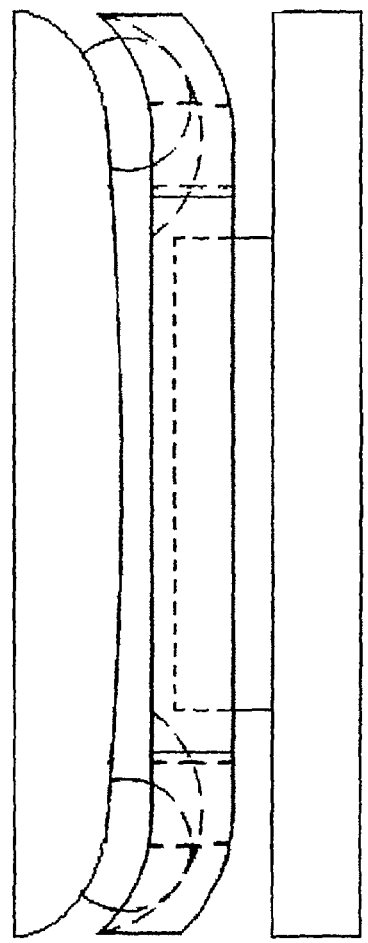

Coronal sectional views of the device are shown in FIGS. 20A and 20B. Sagittal sectional views are illustrated in FIGS. 21A and 21B. In use, the inferior articulation permits arcuate movement in the coronal plane and translational movement in the sagittal plane. Rotation is resisted at the inferior articulation. The superior articulation permits arcuate movement in the sagittal plane and translational movement in the coronal and sagittal planes. Limited rotational movement is also permitted. Additional embodiments are shown in FIGS. 22A and 22B. Both of these embodiments contain two sets of articulation surfaces wherein the inferior articulation allows, at a minimum, arcuate movement in the sagittal plane while the superior articulation allows, at a minimum, arcuate movement in the coronal plane.

Figure 23:
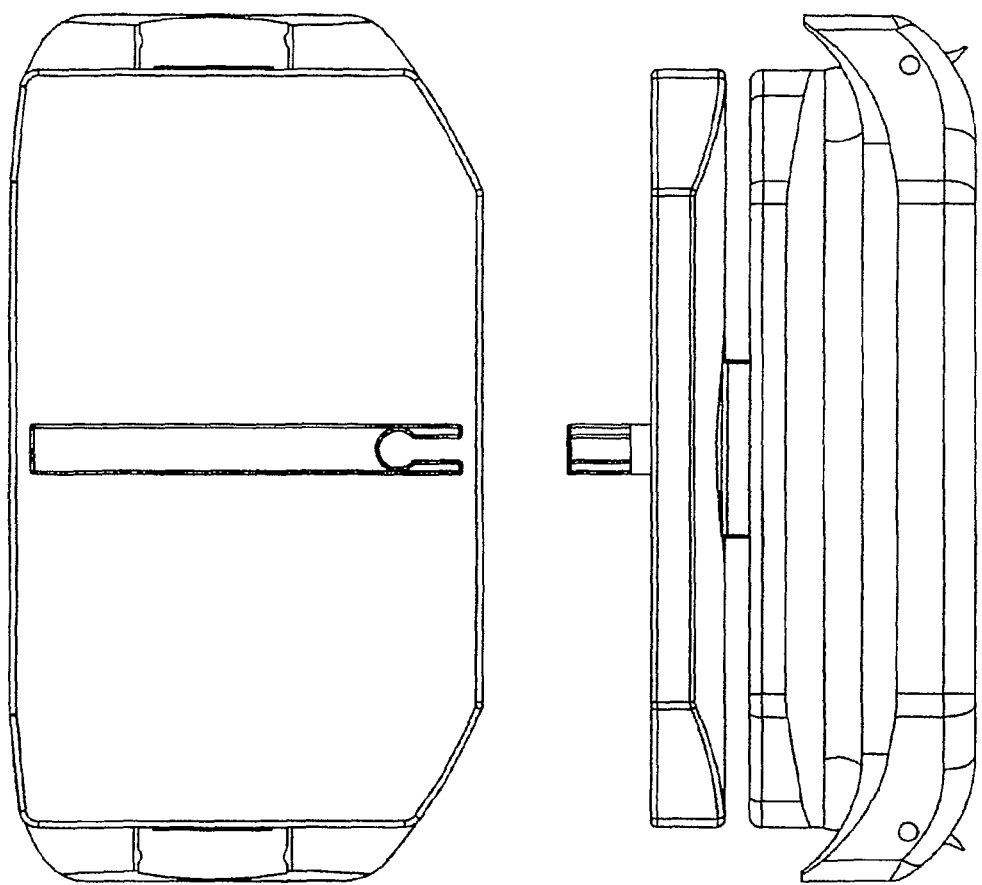
FIG. 23 illustrates an additional embodiment of the prosthesis.
Figure 25:
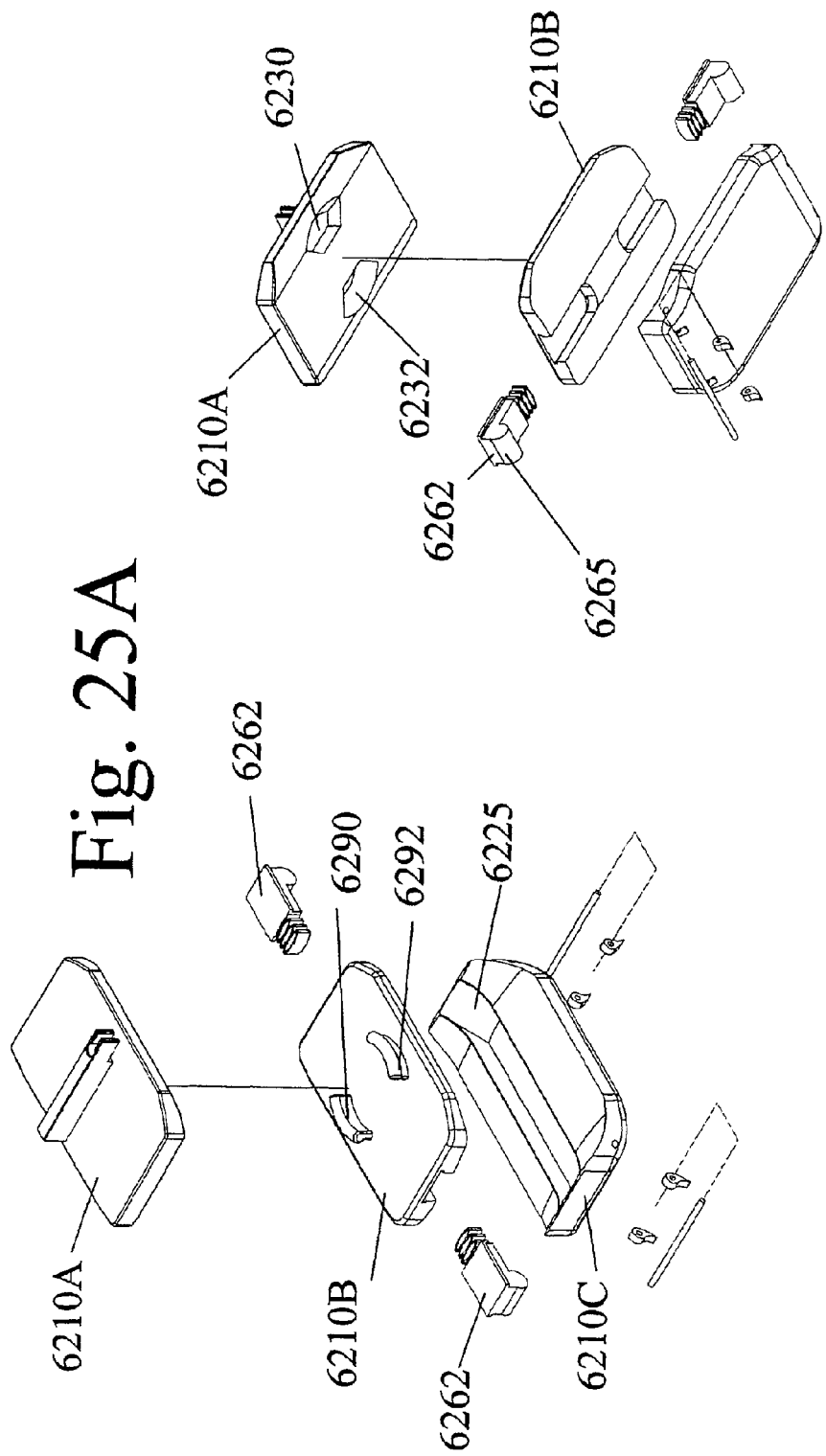
FIGS. 25A and 25B shows cross-sectional views of the prosthesis of FIG. 23.
Figure 26:
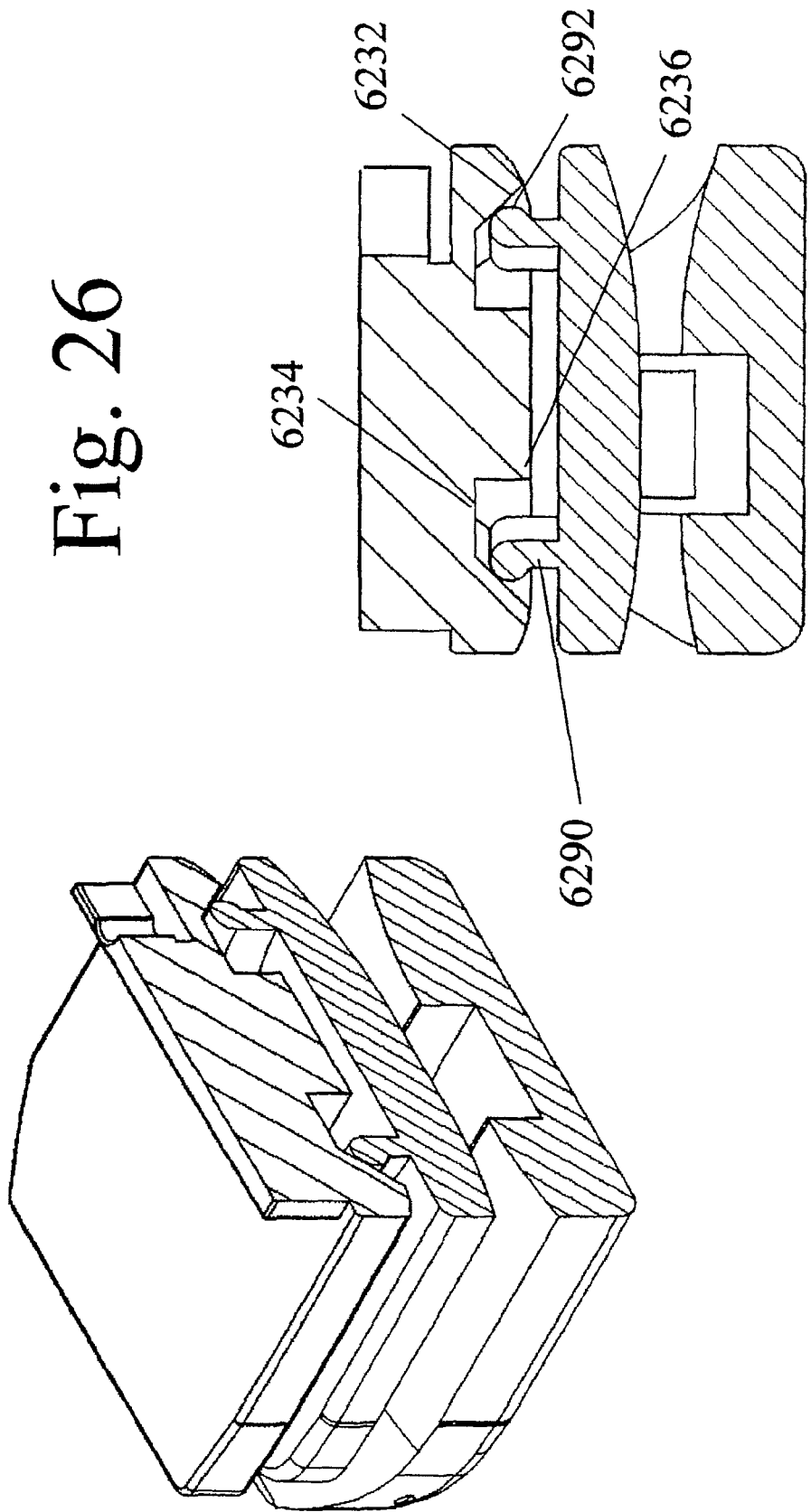
FIG. 26 shows exploded views of the prosthesis.

Another embodiment is shown in FIG. 23 while transparency views are illustrated in FIG. 24. Upper, middle and lower member articulate to form a mobile prosthesis 6200 with an articulation between the upper and middle members and an articulation between the middle and lower members. Exploded views of the prosthesis are shown in FIGS. 25A and 25B while cross-sectional views of the assembled device are illustrated in FIG. 26. As in previous embodiments, the upper and lower components 6210 each have an abutment surface that is adapted to abut against a vertebra when the implant is positioned within an evacuated disc space. The abutment surfaces of the upper and lower components are preferably adapted to promote boney ingrowth and integration.

The articulation between the lower member 6210C and the middle member 6210B is similar to the articulation described in the second embodiment. In this embodiment, the articulation surface 6225 of lower member 6210C is an inclined plane. Member 6262 contains cylindrical protrusions 6265, wherein the long axis of each protrusion is in the sagittal (anterior-posterior) plane. The protrusions 6265 articulate with inclined plane surface 6225 of lower member 6210C to form the inferior articulation. Preferably, cylindrical protrusions 6265 are of lesser anterior-to-posterior length than the anterior-to-posterior length of surfaces 6225, allowing some anterior/posterior translation of the two surfaces relative to one another.

Figure 27A:
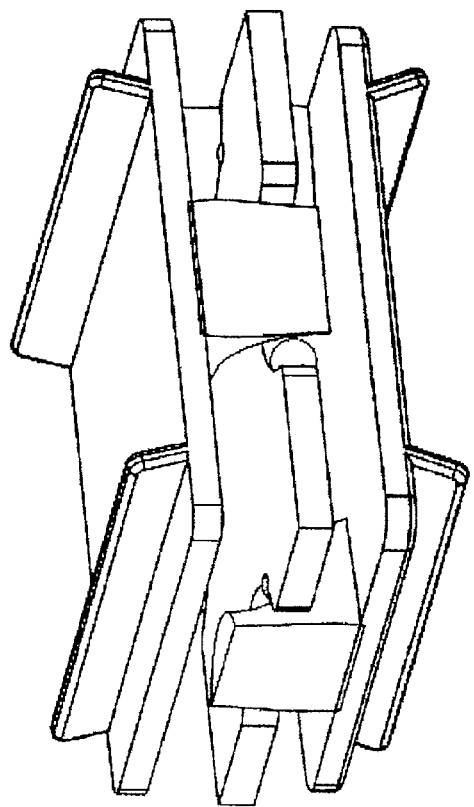
FIGS. 27A and 27B show another embodiment of the prosthesis.
Figure 27B:
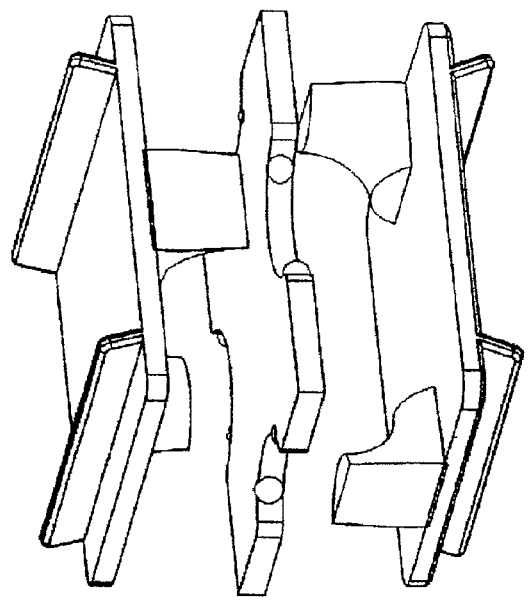

Upper member 6210A has two cavities 6230, wherein each cavity is sized to receive at least a portion of the articulation protrusion 6290 of middle member 6210B. A cross sectional view of the articulation between the middle and upper members is illustrated in FIG. 26. Each cavity 6230 has lateral surface 6232 that is formed as segment of a conical slice, wherein the conical slice has a top surface 6234 of cavity 6230, bottom surface 6236 of member 6210A and a center line is substantially parallel to the vertical center line of upper member 6210A. Each lateral surface 6232 is a segment of the circumferential outer surface of the aforementioned conical section. Surface 6232 forms an articulation with surface 6292 of protrusion 6290 of middle member 6210B. As shown in FIG. 24, the length of protrusion 6290 in the coronal (side to side) plane is preferably smaller that of cavity 6230 so that limited rotation and coronal translation are also permitted. An additional three member embodiment is illustrated in FIG. 27.

Figure 30:
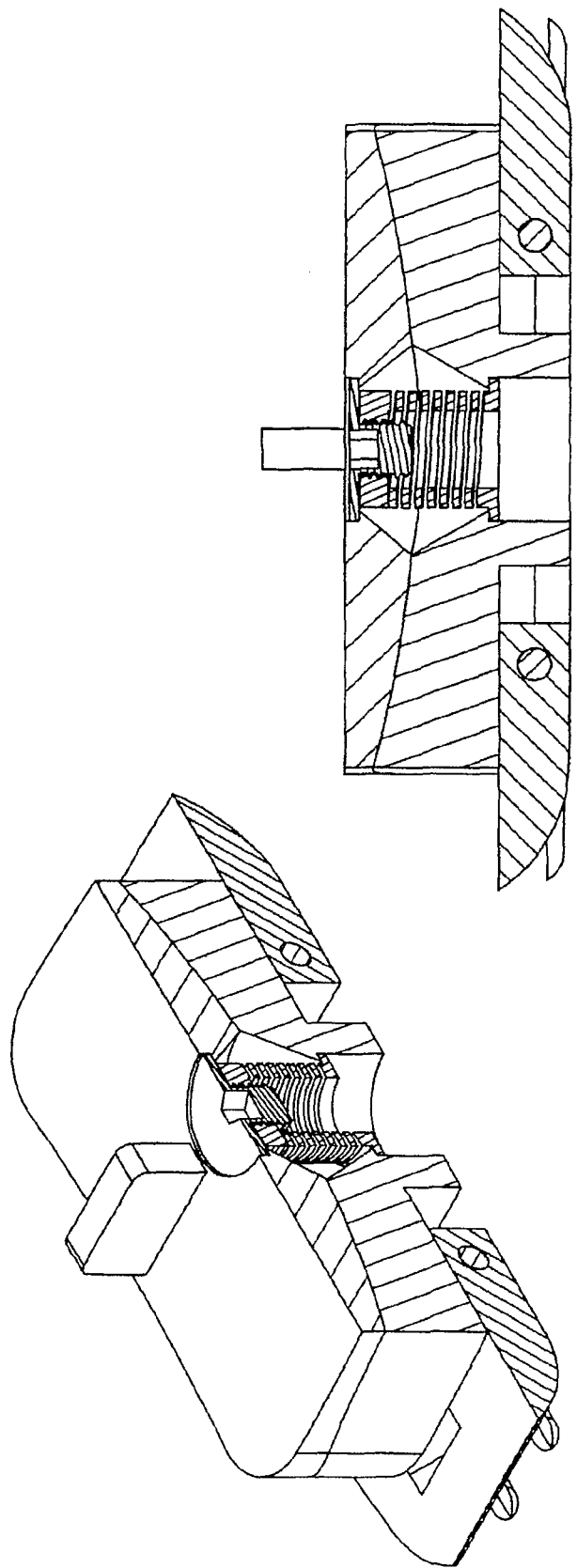
FIG. 30 shows cross-sectional views of the prosthesis.

FIG. 28 illustrates an additional embodiment. The device contains unique bone attachment mechanisms and a self-centering feature. Once again, an upper and a lower member articulate to form a mobile prosthesis. Exploded views of the prosthesis are shown in FIGS. 29A and 29B while cross-sectional views of the assembled device are illustrated in FIG. 30. Regardless of the specifics of the articulation surfaces, the device has a split keel embodiment attached to at least one device member. Unlike the prior split keel embodiment, the present embodiment expands and opens in a different direction. The lower member has movable attachments 5075 that slidably affix onto its inferior surface.

Figure 31A:
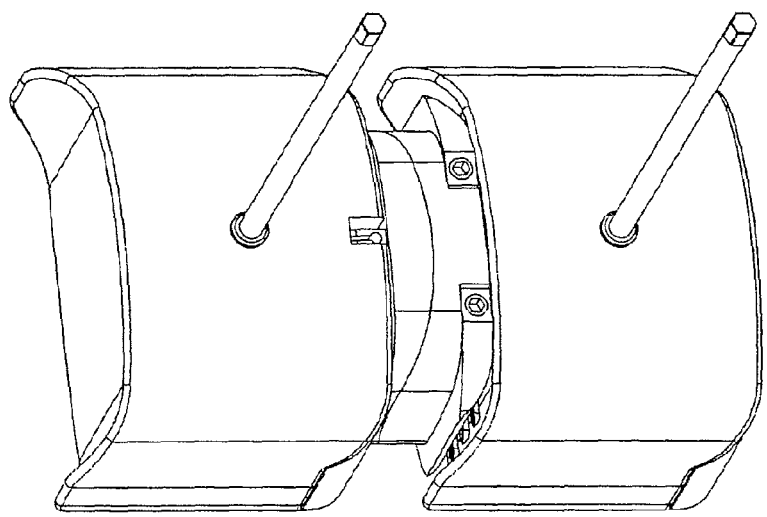
FIG. 31A shows the device within the evacuated disc space.
Figure 31B:
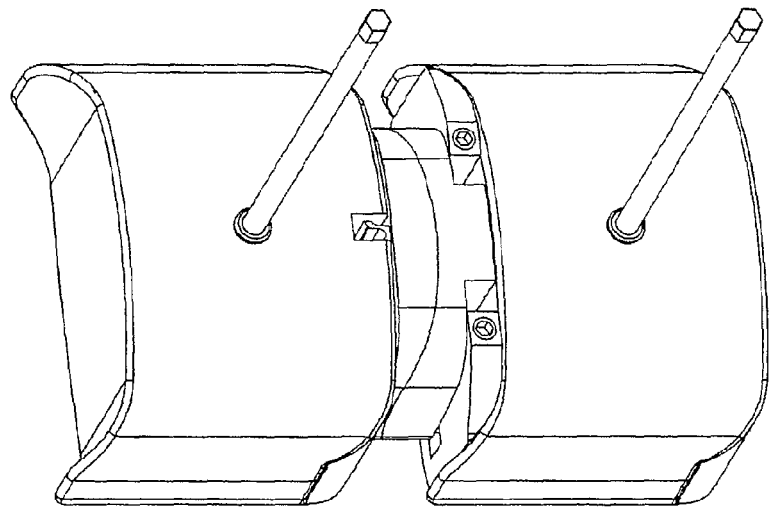
FIG. 31B shows movable attachments translated laterally so that bone pins are forcibly imbedded into the superior aspect of the lower vertebra.
Figure 32:
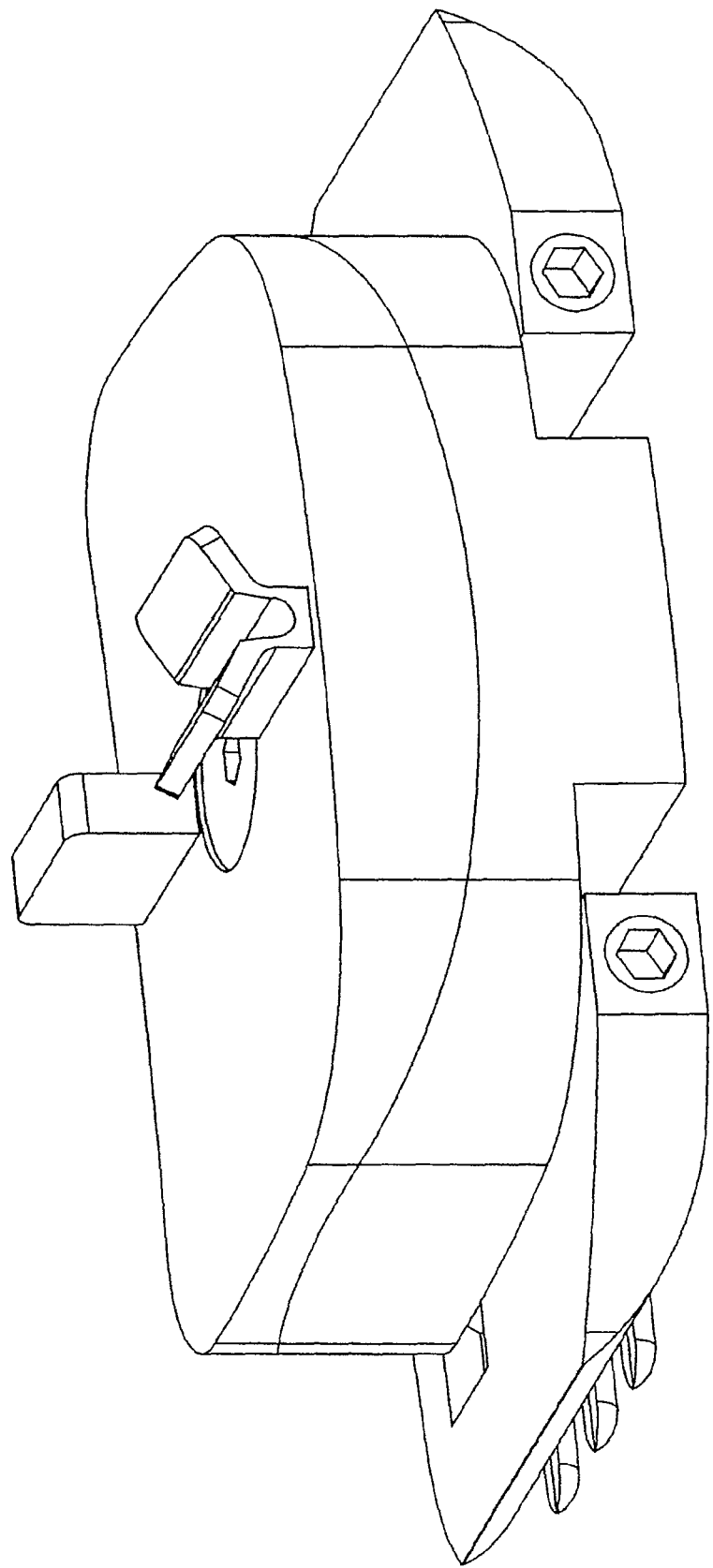
FIG. 32 shows the implanted prosthesis without the vertebral bones.
Figure 33A:
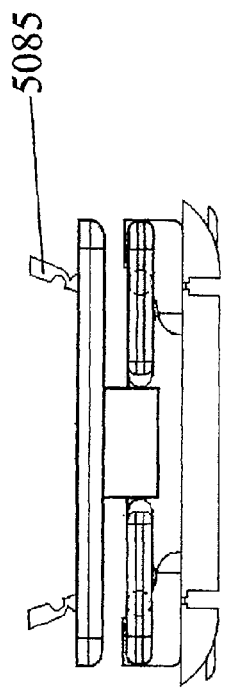
FIGS. 33A-33C illustrate a malleable keel feature that is a variant of the expandable keel design.
Figure 33C:
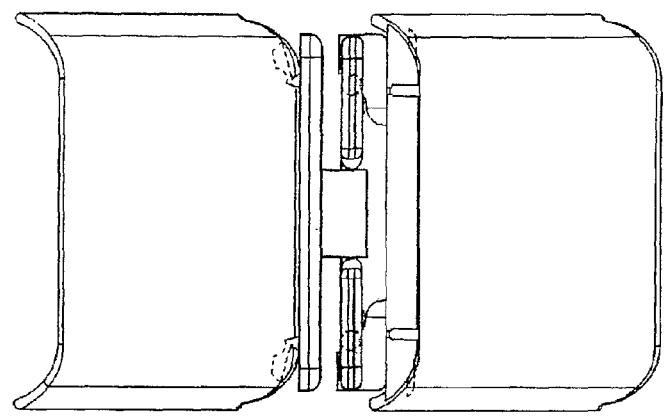
Figure 33B:
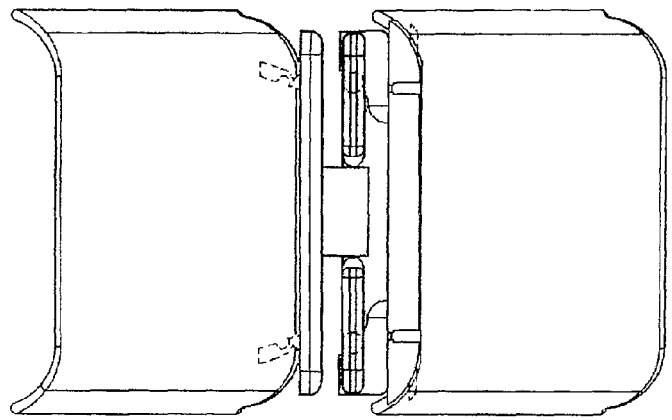

In FIG. 31A, the device is shown within the evacuated disc space. In FIG. 31B, the movable attachments are translated laterally so that bone pins 5077 are forcibly imbedded into the superior aspect of the lower vertebra. Locking screws 5079 are then engaged to retain attachment members 5075 in the bone-engaging position. The implanted device is illustrated without the vertebral bones in FIG. 32. The open keel superiorly and separated attachment members 5075 inferiorly advantageously increases the extent of device fixation into the vertebral bones. In addition, the independent movement of each member 5075 allows the device to center itself relative to the unco-vertebral joints without the need for intra-operative X-ray localization. FIGS. 33A-33C illustrate a malleable keel feature 5085 that is a variant of the expandable keel design. Like the prior embodiments, it is based on the principle of keel placement through a pre-cut bone corridor with a subsequent change in configuration so that the keel is retained within the bone.

FIGS. 34A and 34B illustrate partially exploded views of another device embodiment that is sized and shaped to be positioned within an inter-vertebral disc space, wherein the natural disc has been at least partially evacuated. The implant 5905 includes an upper component 5910A and a lower component 5910B. As in the previous embodiment, the upper and lower components each have an abutment surface 5915 that is adapted to abut against a vertebra when the implant is positioned within an evacuated disc space. The abutment surfaces 5915 of the upper and lower components are preferably configured to promote interaction with the adjacent bone and affix the implant to the bone.

Figure 35A:
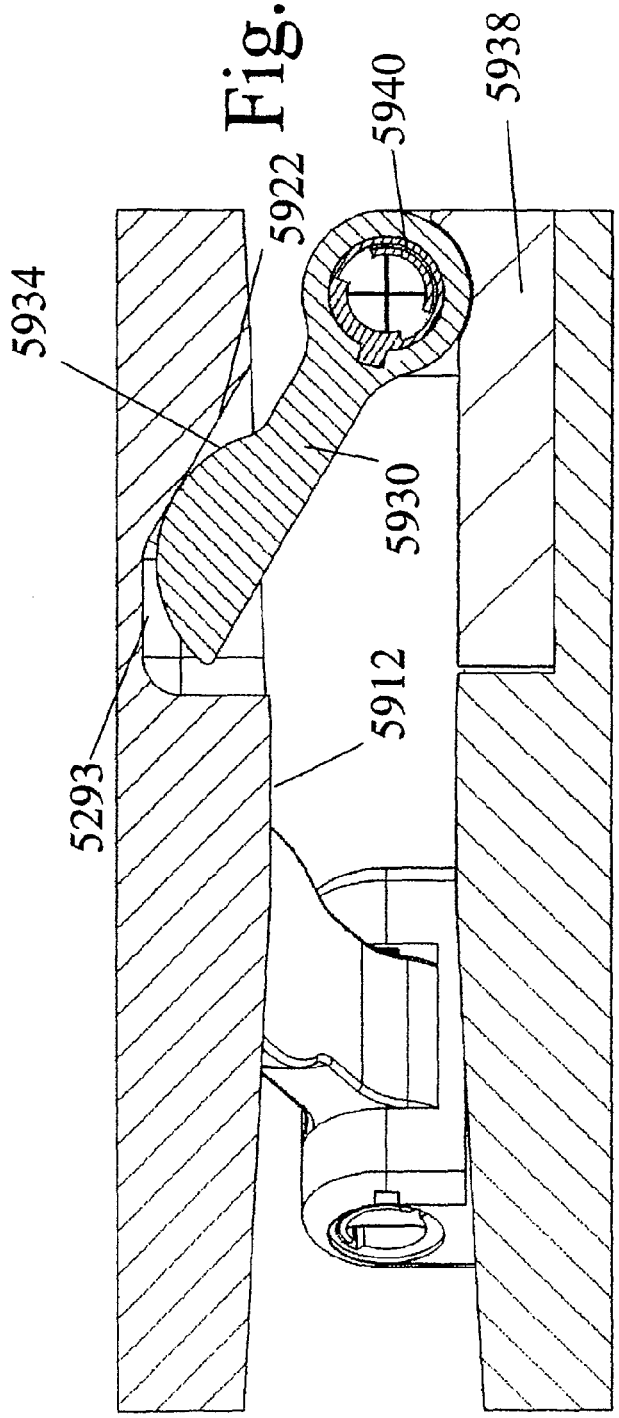
FIG. 35A shows a cross sectional view of the articulation between a swing arm and a cavity.

The upper component 5910A has preferably three interior cavities 5920, wherein each cavity 5920 is sized to receive at least a portion of a swing arm 5930. A cross sectional view of the articulation between a swing arm 5930 and a cavity 5920 is illustrated in FIG. 35A. Each cavity 5920 has lateral surface 5922 that is formed as segment of a conical slice that has a top surface 5293 of cavity 5920, bottom surface 5912 of component 5910A and has a center line 5927 of circle 5929. Each lateral surface 5922 is a segment of the circumferential outer surface of the conical section thus firmed. Surface 5922 forms an articulation with the surface 5934 of swing arm 5930.

In addition to the articulation with upper component 5910A, each swing arm 5930 is adapted to deform or otherwise yield in response to a compressive vertical component of a load placed upon device 5905. In this regard, the swing arm 5930 is biased toward a default position such that the swing arm returns to that configuration or position after the force acting upon the implant has dissipated. One such default configuration or position is shown in FIG. 35A. With reference to FIG. 35A, the swing arm 5930 functions as a lever member that is pivotably coupled to removable member 5938 by malleable hinge member 5940. The hinge member 5940 mounts within a slotted shaft at the base of swing arm 5930 and within another slotted shaft within removable member 5938.

In a default state, the swing arm 5930 is biased toward the position shown in FIG. 35A. The swing arm 5930 is adapted to pivot about an axis defined by the hinge member 5940 such that the swing arm can move about a curvilinear pathway. In this manner, the swing arm 5930 can change position in response to loads applied to implant 5905 such that the upper and lower components can move toward one another in a manner that is determined and limited by motion characteristics of hinge member 5940.

Figure 35B:
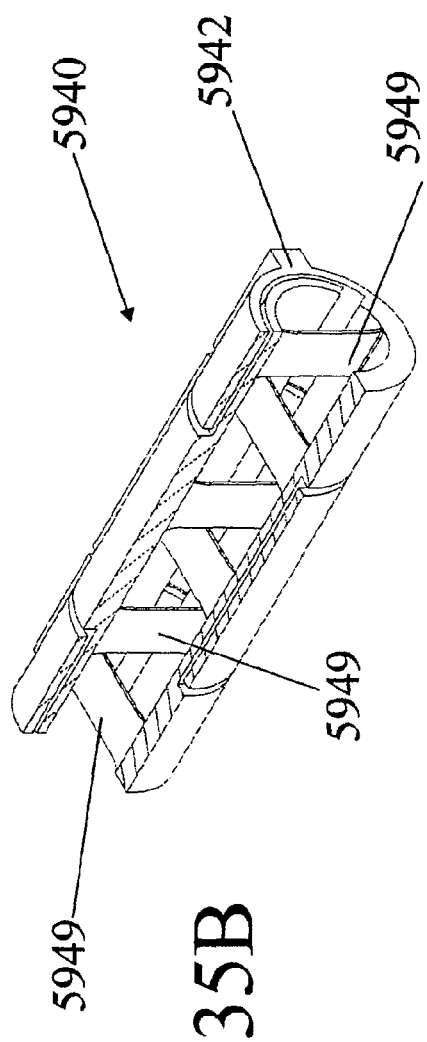
FIG. 35B shows a perspective view of the hinge member with one quadrant of outer wall removed.

FIG. 35B shows a perspective view of the hinge member 5940 with one quadrant of outer wall removed. The hinge member 5940 includes an outwardly extending tooth 5942 that mates with complimentary-shaped slot within the mounting shaft of the base of swing arm 5930 and removable member 5938. The hinge member 5940 is formed of a plurality of sections. The hinge member utilizes internal flat crossed members 5942, capsuled in a multi-segmental cylindrical housing, to provide precise rotation movement with low hysteresis characteristics. The hinge member 5940 provides relatively friction-free angular motion, requires no lubrication, and returns to a pre-determined default (neutral) position after the force acting upon it has dissipated. Members 5949 resist rotational movement away from the default state and the extent of resistance to rotation is directly related to the extent of rotation. The extent of total resistance to rotational is a pre-determined property of the device. In one embodiment, the hinge member has high radial stiffness, high axial stiffness, provides frictionless rotational movement and produces little to no particle wear debris. An exemplary hinge member of the type shown in FIG. 30B is distributed by Riverhawk Company of New York under the name FLEX PIVOT.

Figure 36:
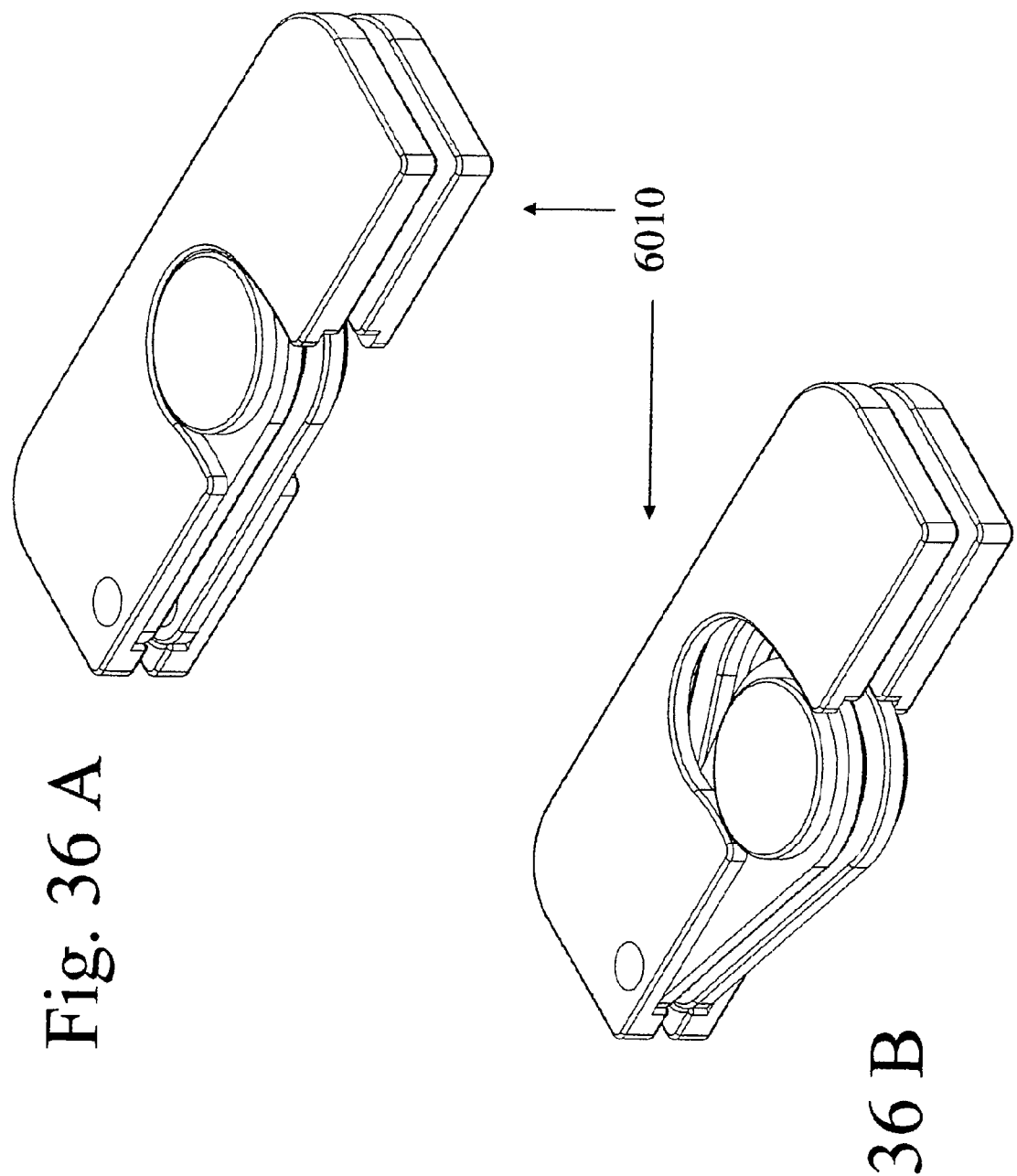
FIG. 36A illustrates another prosthesis embodiment.
FIG. 36B shows the prosthesis of FIG. 26 in an open state.
FIGS. 36C and 36D show exploded views of the prosthesis.
Figure 36D:
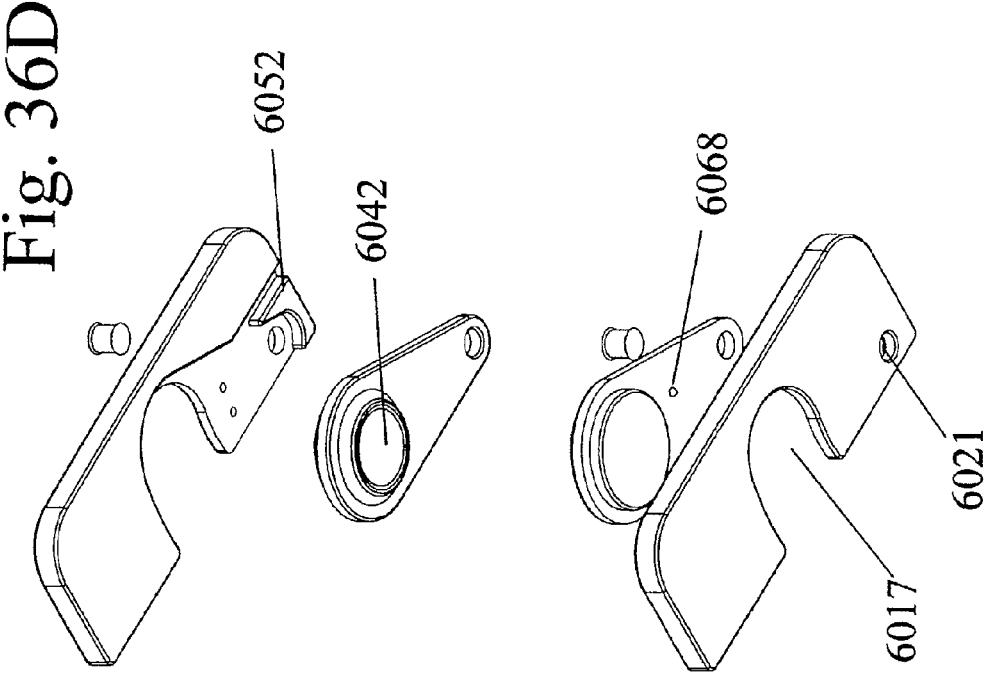
Figure 36C:
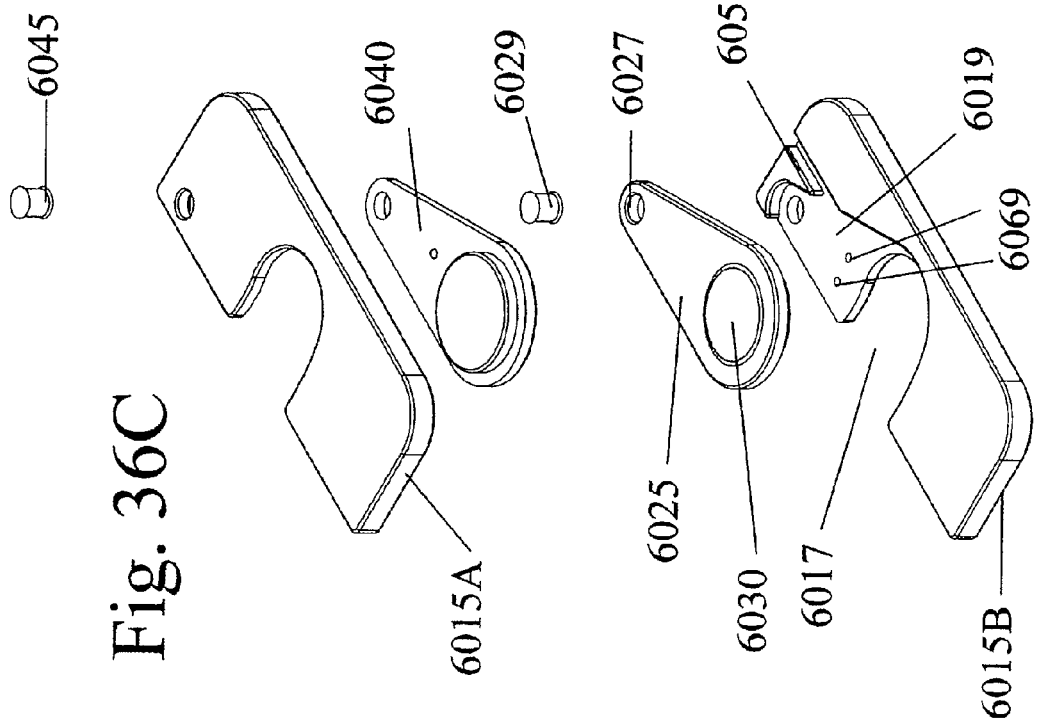

FIG. 36A illustrates another device embodiment. Once again, an upper and a lower member articulate to form a mobile prosthesis 6010. Exploded views of the prosthesis are shown in FIGS. 36C and 36D while cross-sectional views of the assembled device are illustrated in FIG. 37A. As in previous embodiments, the upper and lower components 6015 each have an abutment surface that is adapted to abut against a vertebra when the implant is positioned within an evacuated disc space. The abutment surfaces of the upper and lower components are preferably configured to promote interaction with the adjacent bone.

The embodiment has a retractable articulating surface so that device 6010 may be configured in a first, closed state as shown in FIG. 36A or configured in a second, open state as shown in FIG. 36B. With reference to FIG. 36C, lower component 6015B has full thickness bore 6017 and partial thickness shelf 6019 with second bore hole 6021. Member 6025 contains bore 6027 on one end, which is adapted to accept fastener 6029. In the assembled state, fastener 6029 resides within bore 6027 of member 6025 and within bore 6021 of component 6015B and serves to couple 6025 to 6015B while still permitting rotational movement between these two members. Member 6025 has a spherical protrusion 6030 that forms a ball-and-socket articulation with complimentary surface 6042 of member 6040. A cross-sectional view of the articulation is illustrated in FIG. 37A. Upper segment 6015A is formed as a mirror image of 6015B and is similarly adapted to couple with member 6040 using fastener 6045.

Device 6010 is preferably implanted into the evacuated disc space from a lateral approach (arrow A, FIG. 37B). Since various important nerve structures will cross the lateral aspect of the disc space, the device is implanted in a first, closed configuration in order to minimize the size of the implantation pathway and decrease the possibility of nerve damage. After implantation, articulation member 6025 and 6040 are jointly rotated away from stationary upper and lower components 6015 to form a second, open prosthesis configuration. FIG. 37A illustrates an implanted device 6010 in a first, closed configuration while FIG. 37B shows the device 6010 in a second, open configuration. The rotational movement of member 6025 and 6040 is produced by the advancement of a tool (not shown) within slot 6051 of component 6015B and slot 6052 of component 6015A. While components 6015 are held stationary, the tool is advanced and used to abut and forcibly rotate member 6025 and 6040 relative to components 6015.

The inferior surface of member 6025 abuts and rests upon the partial thickness shelf 6019 of component 6015B. Protrusion 6068 emerges from the inferior surface of member 6025 and is adapted to fit within and interact with either of the two indentations 6069 on shelf 6019. As shown in FIG. 37B, protrusion 6068 resides within anterior indention 6069 when the device is in a first, closed configuration and the interaction of the protrusion/indentation retains the device in the first configuration. Conversely, FIG. 37C shows the device in the second, open configuration with protrusion 6068 in the posterior indentation 6069. Similar complimentary retaining features are found in the upper surface of member 6040 and the lower surface of component 6015A. FIG. 37A shows the interactions in a cross-sectional view.

In an alternative embodiment (not shown), these retaining features are removed so that the movement of member 6025 relative to component 6015B and the movement of member 6040 relative to component 6015B are no longer constrained. In this way, the unhindered movement of member 6025 relative to component 6015B forms a second articulation within the prosthesis while the movement member 6040 relative to component 6015A forms a third articulation. With motion, all three articulations can participate in movement of the vertebral bodies.

Figure 38:
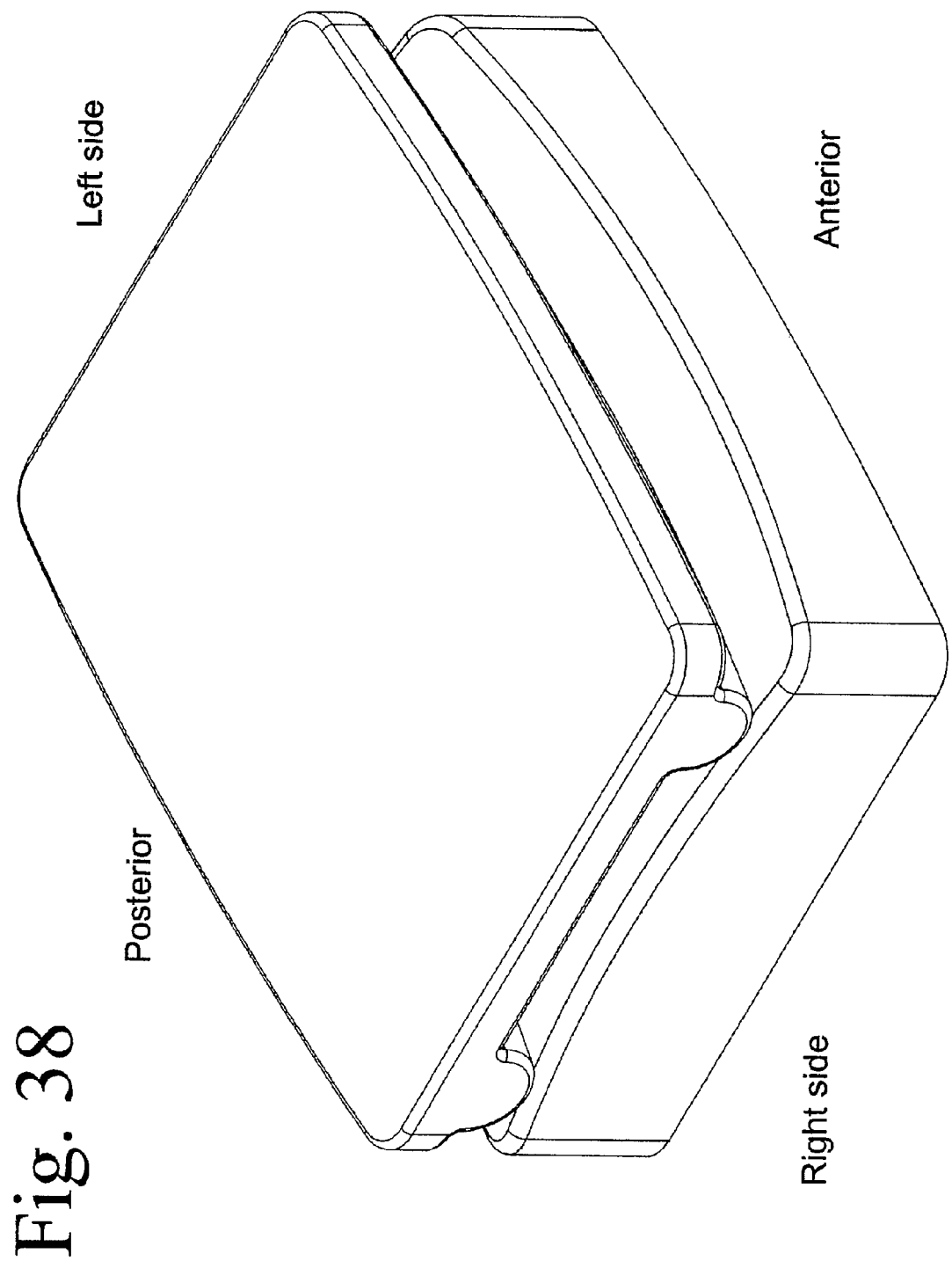
FIG. 38 illustrates another embodiment of an artificial disc prosthesis.
Figure 39:
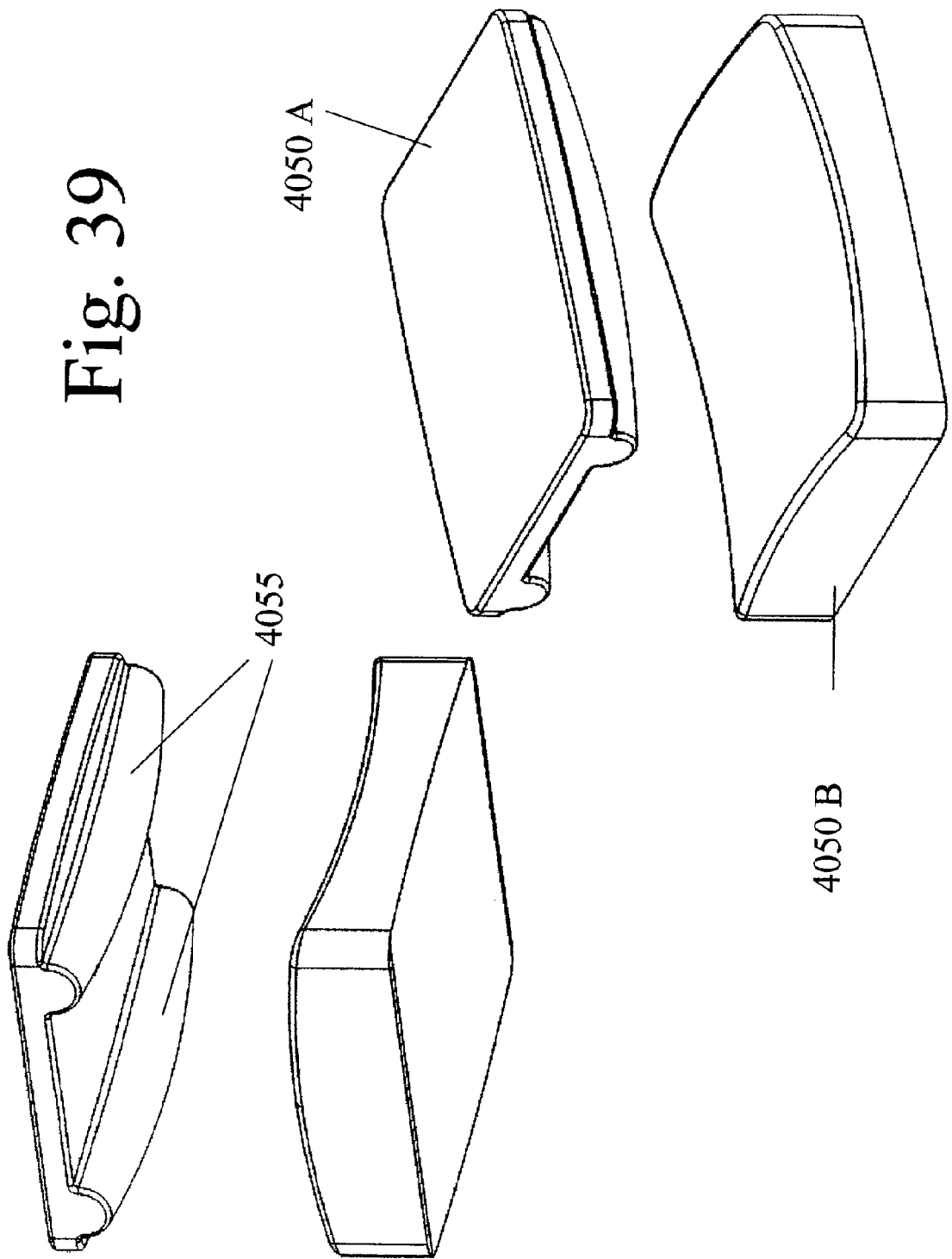
FIG. 39 shows perspective views of the prosthesis with a two members separated.

FIGS. 38 and 39 illustrate another embodiment of an artificial disc prosthesis. The device is made up of a superior member 4050A and an inferior member 4050B. After removal of an inter-vertebral disc, the device is placed within the evacuated disc space and replaces the function of a natural inter-vertebral disc. The top surface of upper member 4050A abuts the lower surface of the upper vertebra while the bottom surface of the lower member 4050B abuts the upper surface of the lower vertebra. The bone-abutting surfaces may be further textured to increase bone contact and/or coated with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone in-growth, bone formation, or establish a mineralized connection between the bone and the implant. They may be also made of materials known to promote bone formation.

An articulation is formed between the two members 4050 and provides movement between them and the attached vertebral bodies. FIG. 39 shows perspective views of the device with the two members 4050 separated. The articulating surface of the inferior member 4050B is a sub-segment of a three-dimensional structure similar to that diagrammatically shown in FIG. 40B. The illustrated three-dimensional structure is generated by the rotation of the circle C1 (with center point C) about center line L1—as shown in FIG. 40A. Thus, the articulating surface of the inferior member 4050B is convex in the sagittal (anterior-posterior) plane and concave in the coronal (right-to-left) plane. A coronal section through the prosthesis contains line L1.

Figure 41B:
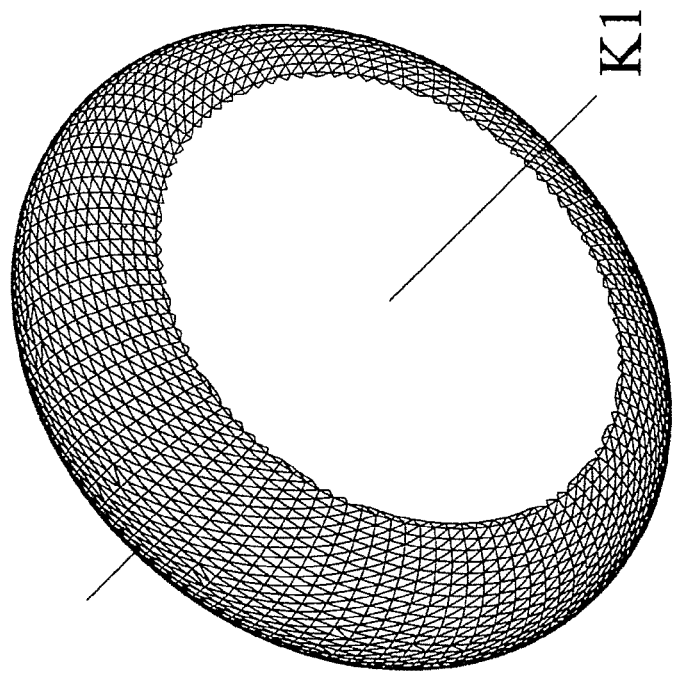
Figure 41A:
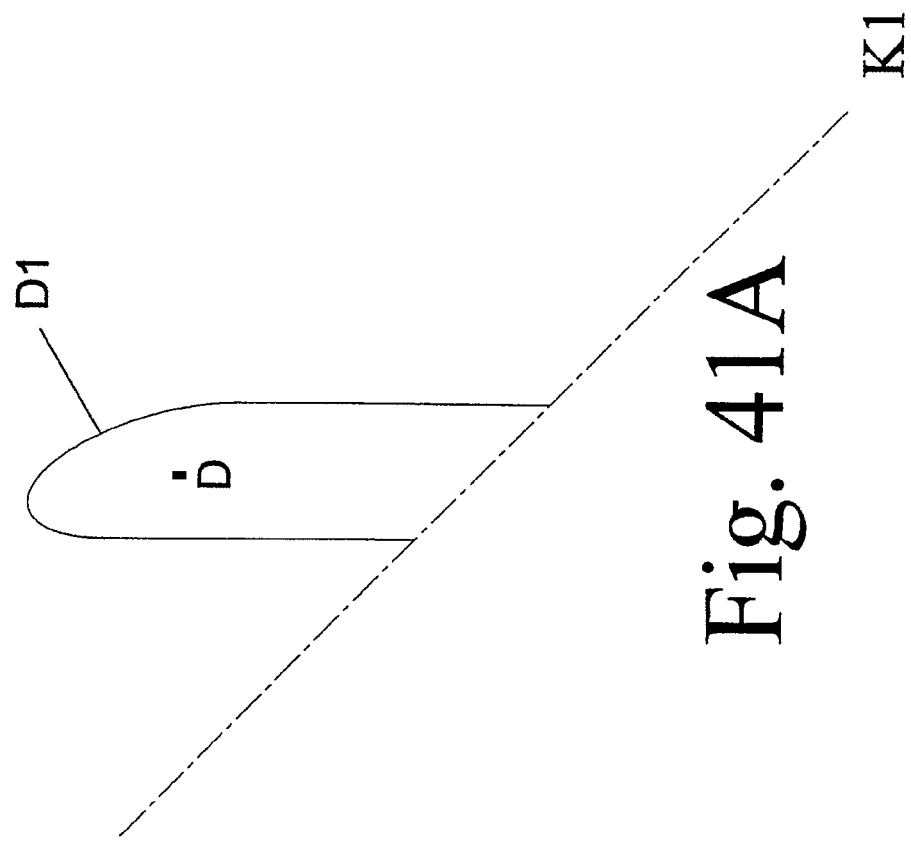
Figure 42:
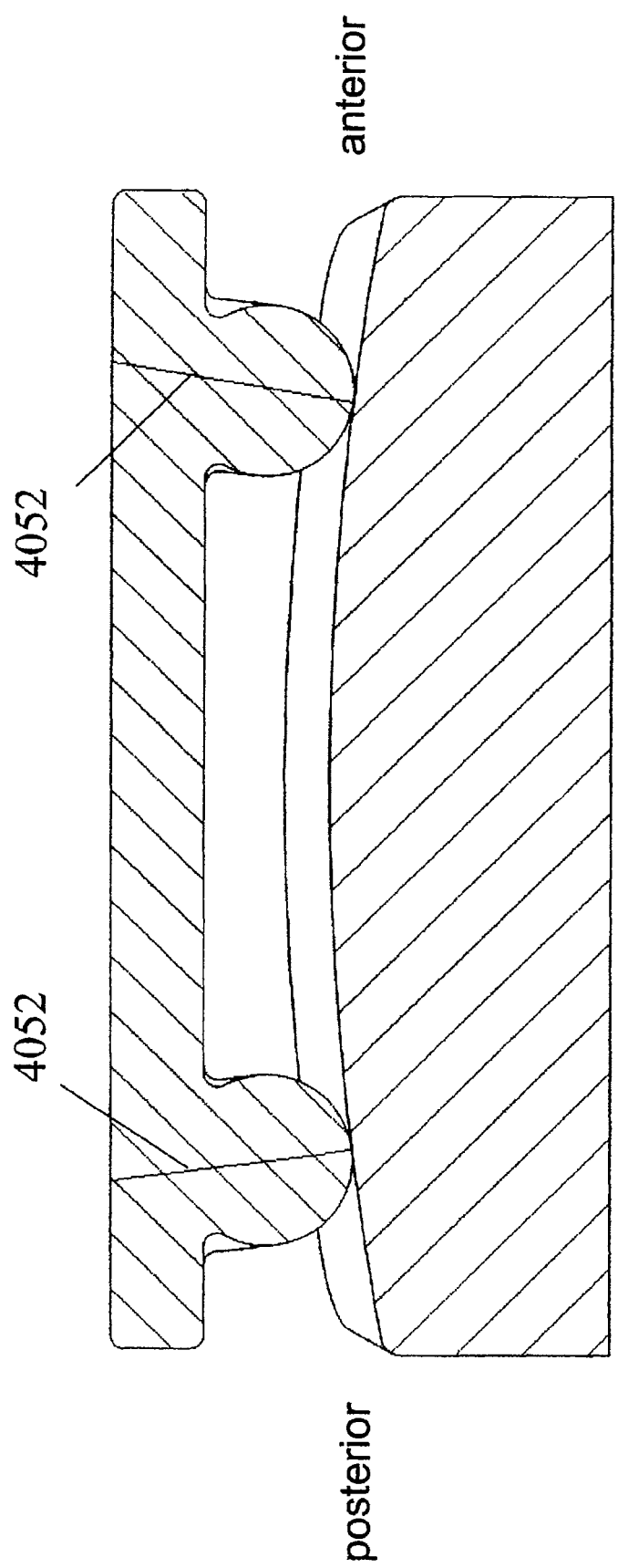
FIG. 42 shows a sagittal (anterior-posterior) section through the prosthesis illustrates the orientation of angled coronal plane.

The superior member has an articulating surface made-up of at least one protrusion 4055 oriented with long axis in the coronal (right to left) plane, wherein protrusion 4055 is a sub-segment of a three-dimensional structure similar to that diagrammatically shown in FIG. 41B. The illustrated structure is generated by the rotation of a circle D1 with center D about a center line K1 (FIG. 41A). In the illustrated embodiment, superior member 4050A has two protrusions 4055. In the preferred embodiment, each protrusion 4055 is oriented so that a coronal section 4052 through the protrusion contains center line L1 that was to generate the articulating surface of the inferior member 4050B. FIG. 42 shows a sagittal (anterior-posterior) section through the prosthesis and illustrates the orientation of angled coronal plane 4052.

The articulation formed permits movement in the sagittal (anterior-posterior) plane with a center of rotation along line L1 which is below the articulation surfaces. It permits movement in the coronal plane with a center of rotation at C (the center point of circle C1—FIG. 40A) which is above the articulation surfaces. Rotation in the axial plane is partially resisted by the articulation surfaces, but when it occurs, it increases the overall height of the entire prosthesis. These motion characteristics replicate the movement of the cervical spine and this embodiment is well suited for cervical disc replacement.

Figure 43:
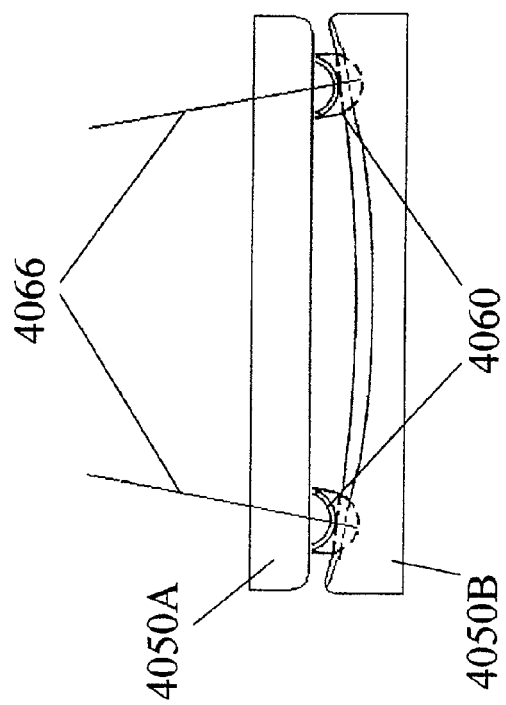
FIG. 43A shows another embodiment of a prosthesis.
FIG. 43B illustrates an exemplary curved contoured surface
Figure 43:
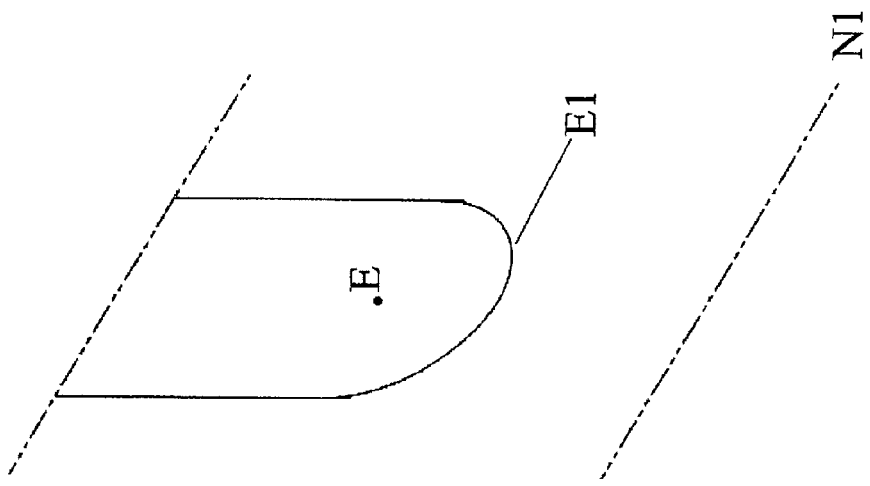

An alternative embodiment is shown in FIG. 43A. A coronal (right-to-left) section through the device is illustrated. While the articulation of the inferior member 4050B is similar to the previous embodiment, the superior articulating surface is different. In this embodiment, one or more protrusions 4060 are oriented with long axis in the sagittal (anterior-posterior) plane, wherein protrusion 4060 is a sub-segment of a three-dimensional structure similar to that diagrammatically shown in FIG. 43B. Circle E1 with center at E is rotated about line N1 to form the articulation surface 4062 of protrusion 4060. Each protrusion 4060 is oriented so that a sagittal section 4066 through the protrusion contains center point C of circle C1 that was to generate the articulating surface of the inferior member 4050B (FIG. 40A). FIG. 43A shows a coronal section through the prosthesis and illustrates the orientation of angled sagittal plane 4066.

FIG. 44 shows another embodiment. The surfaces of the disc prosthesis that abut the vertebral surfaces are preferably shaped to conform to the general outline of the cervical disc space. The articulation surface of the inferior member is similar to the previous embodiment but the superior articulating surface is different. The superior member has three peg-like protrusions with semi-spherical ends that interact with the articulation surface of the inferior member.

Figure 45:
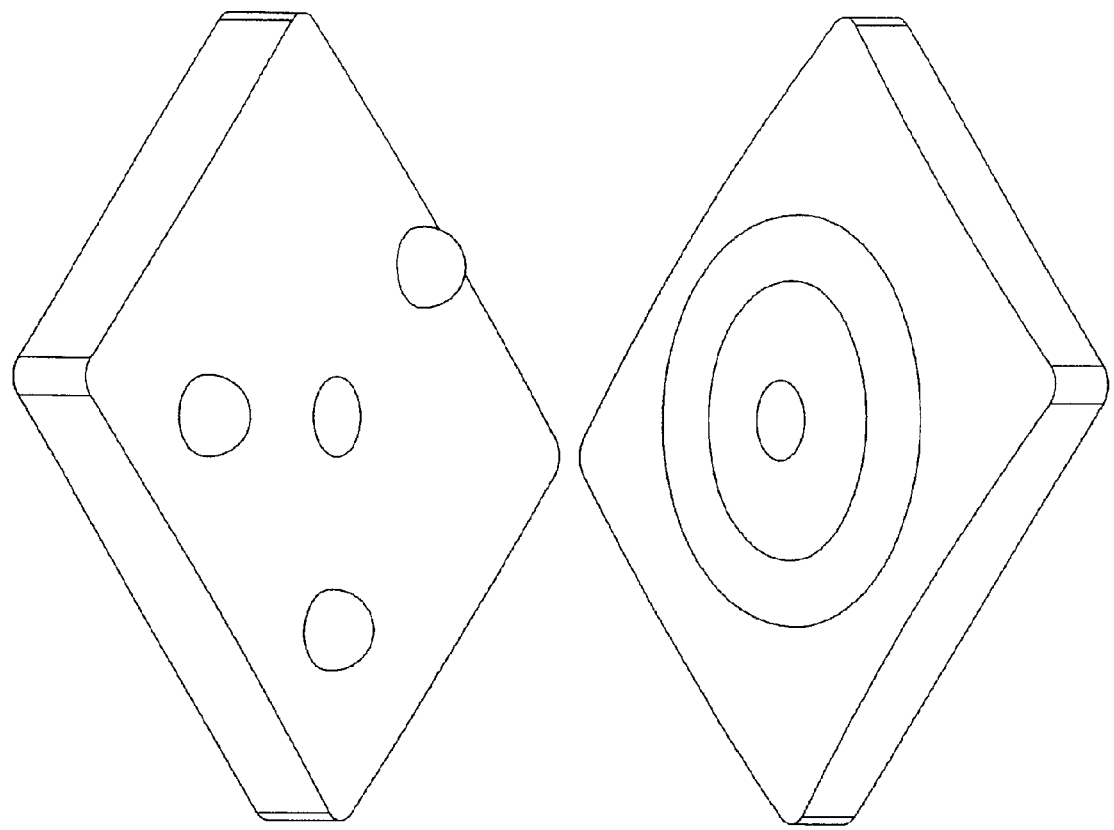
FIG. 45 shows another embodiment of a prosthesis.
Figure 46:
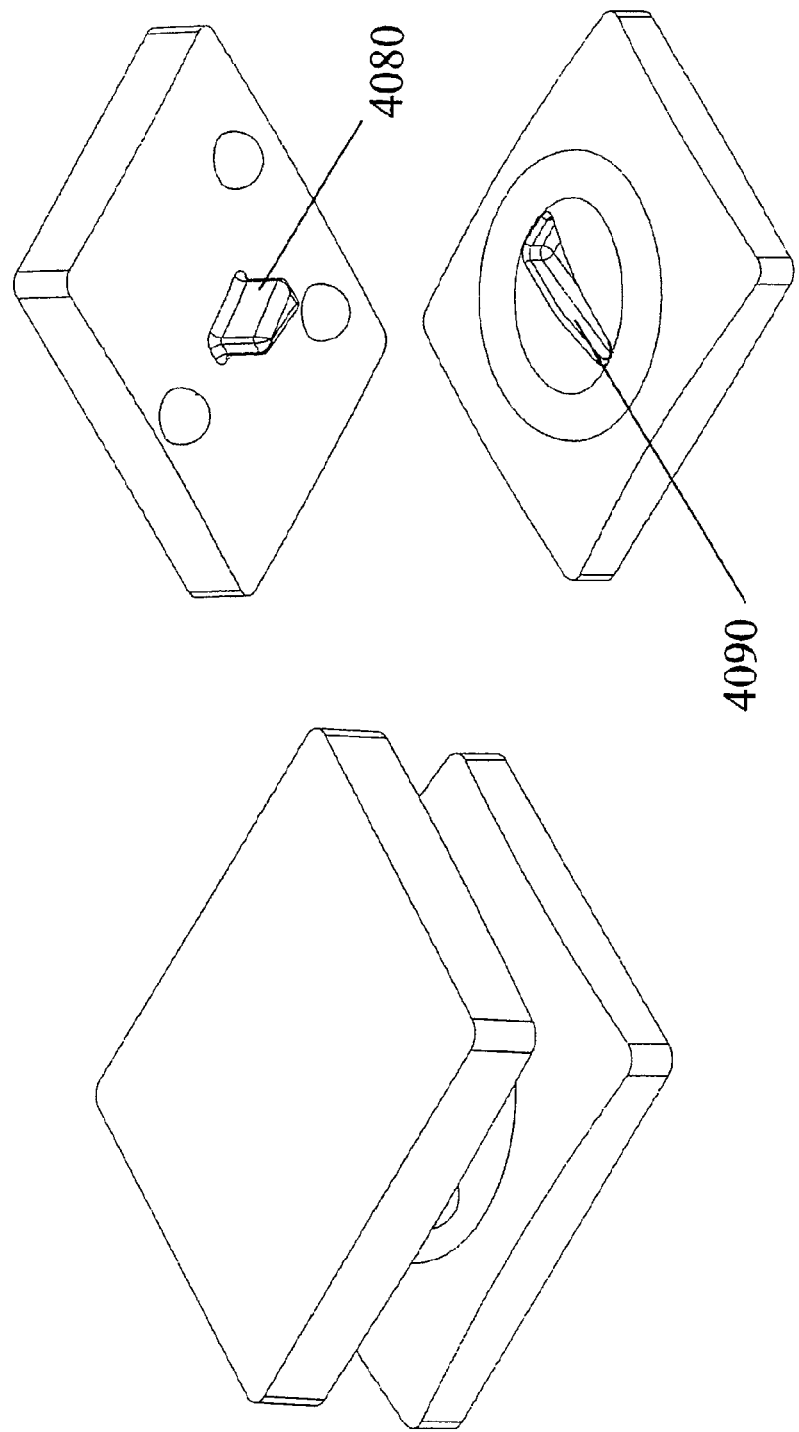
FIG. 46 illustrates an additional embodiment of a prosthesis's which rotation is constrained.

An additional articulation embodiment is shown in FIG. 45. The superior member has three spherical protrusions (alternatively, peg-like protrusions may be used) that articulate with the toroid articulating surface of the inferior member. The movement produced by this articulation follows a curved pathway with a variable center of rotation that is located below the articulating surfaces. This movement profile is displayed in both the sagittal and coronal plane and more closely replicates the motion characteristics of the lumbar spine. While rotation is not limited in this embodiment, FIG. 46 illustrates an additional embodiment in which rotation is constrained. Protrusion 4080 of the superior member interacts with complimentary indentation 4090 of the inferior member to limit rotation. In order to more perfectly replicate the motion characteristics of the natural disc, the extent of rotation permitted by the prosthesis should vary directly with extent of flexion. That is, the prosthesis should permit a greater amount of rotational freedom between the superior and inferior members when the members are in flexion relative to one another than when they are in extension. FIGS. 47A to 47C illustrate the interactions of the protrusion 4080 and indentation 4090 during different stages of flexion/extension. FIG. 47A shows the device in flexion and illustrates that the space between 4080 and 4090 is greater than when the device is in neutral position (FIG. 47B) or in extension (FIG. 47C). The space between 4080 and 4090 determines the extent of rotation permitted by the prosthesis.

Figure 48A:
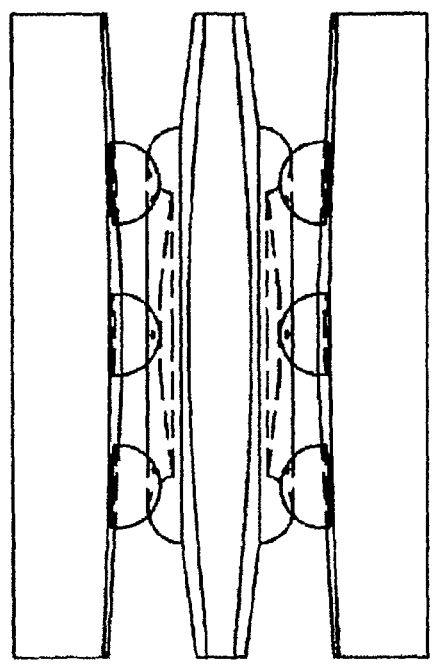
FIGS. 48A and 48B illustrate two additional prosthesis embodiments.
Figure 48B:
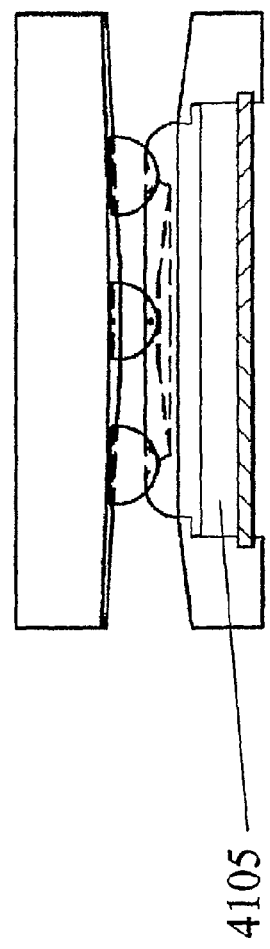

FIGS. 48A and 48B illustrate two additional device embodiments. In FIG. 48A, the superior and inferior members are similar and the articulation of each consists of three spherical protrusions. A third, intermediate member with a toroid articulation surface on either side is positioned between the superior and inferior members providing the device with an articulation between the superior and intermediate members and a second articulation between the intermediate and inferior members. The embodiment of FIG. 48B has spherical protrusions similar to that of the embodiment shown in FIG. 45. However, the articulation surface of the inferior segment can move in the longitudinal direction within cavity 4105. An elastomeric member is placed within cavity 4105 to resist the downward movement of the articulating surface and impart a dampening or shock-absorption property to the prosthesis.

Figure 49:
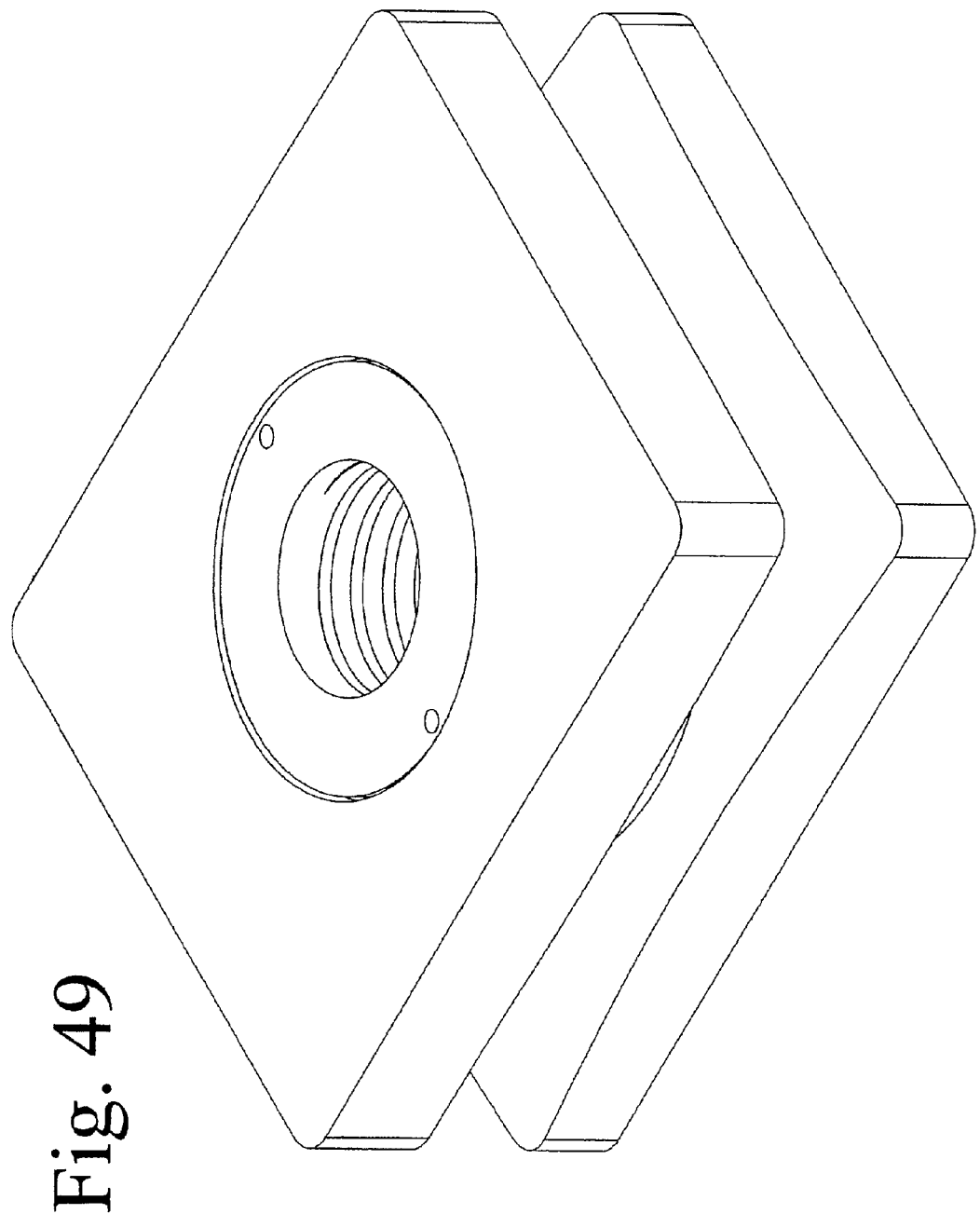
FIG. 49 illustrates another prosthesis embodiment.

FIG. 49 illustrates another device embodiment while FIGS. 50A and 50B show exploded views. Superior member 4050A and inferior member 4050B articulate using three-spherical protrusions on one member and a toroid surface on the other member. Spring member 4120 is preferably a helical machined spring member. The spring member is placed through bore hole 4125 of the superior member and resides at the center of the articulation surface. Inferior member 4050B contains bore hole 4130 and is adapted to accept cap member 4122. The cap has a threaded protrusion that can interact and thread into spring member 4120. The assembled device is seen in cross-section in FIG. 51.

Figure 52:
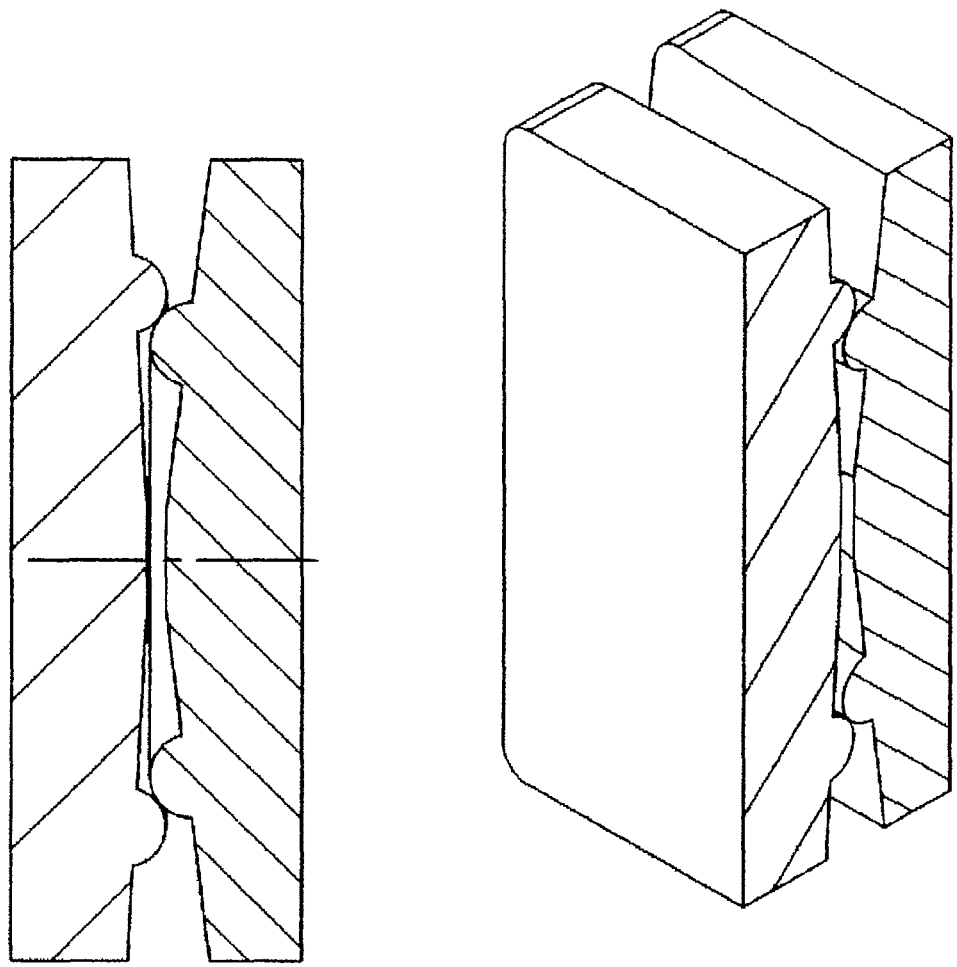
FIG. 52 illustrates another prosthesis embodiment.

An additional embodiment is illustrated in FIG. 52. A toroid articulation surface is located on each of the superior and inferior members, wherein the toroids are of different radii. A variation is shown in FIGS. 53A-53C wherein one member has a toroid articulation surface and the other member uses a segment of a cone as its articulation surface. The embodiment of FIG. 54 is a variation of that shown in FIG. 53. However, in the former, the central portion of the toroid has been filed with material.

Figure 56:
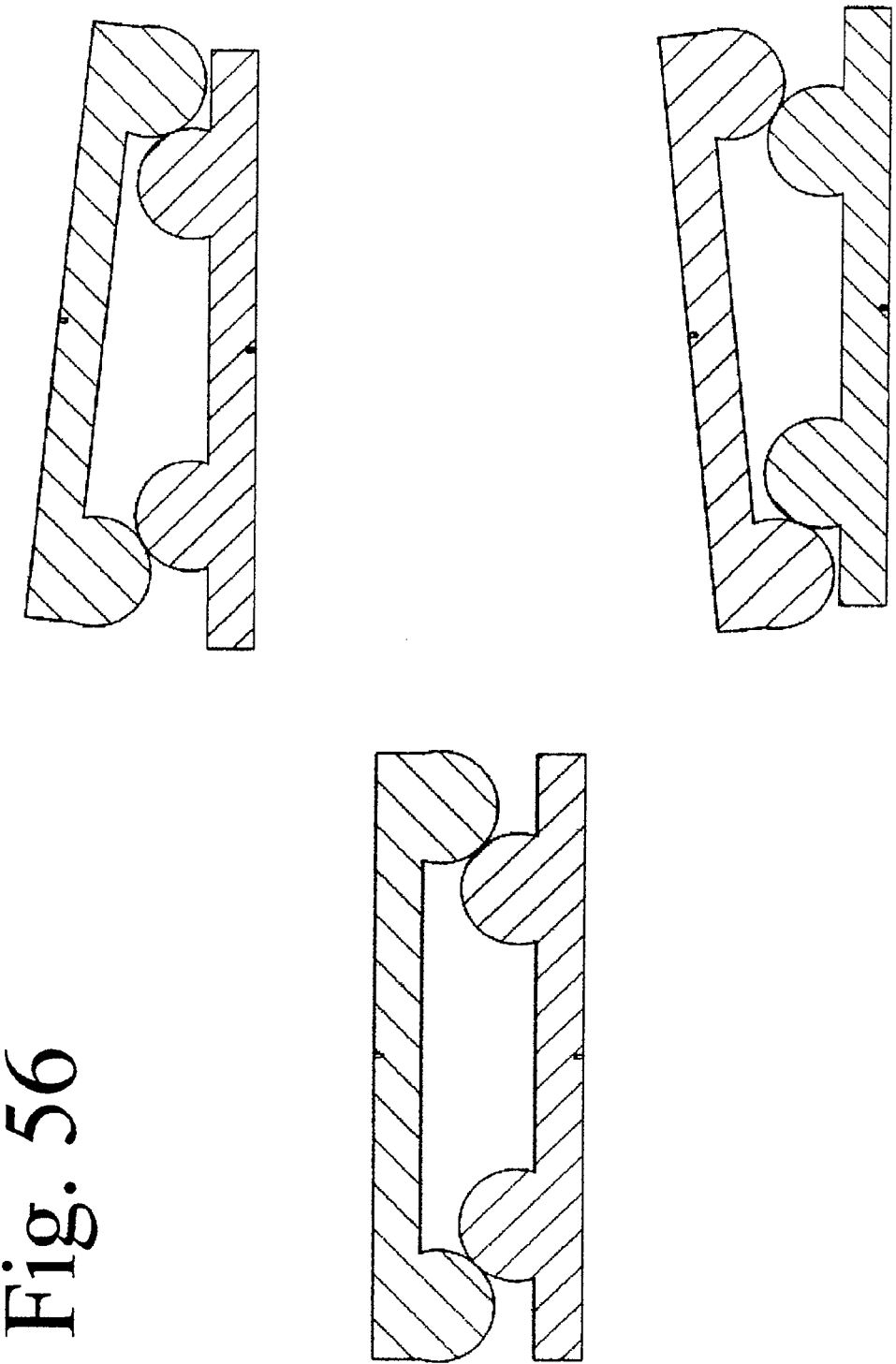
Figure 58:
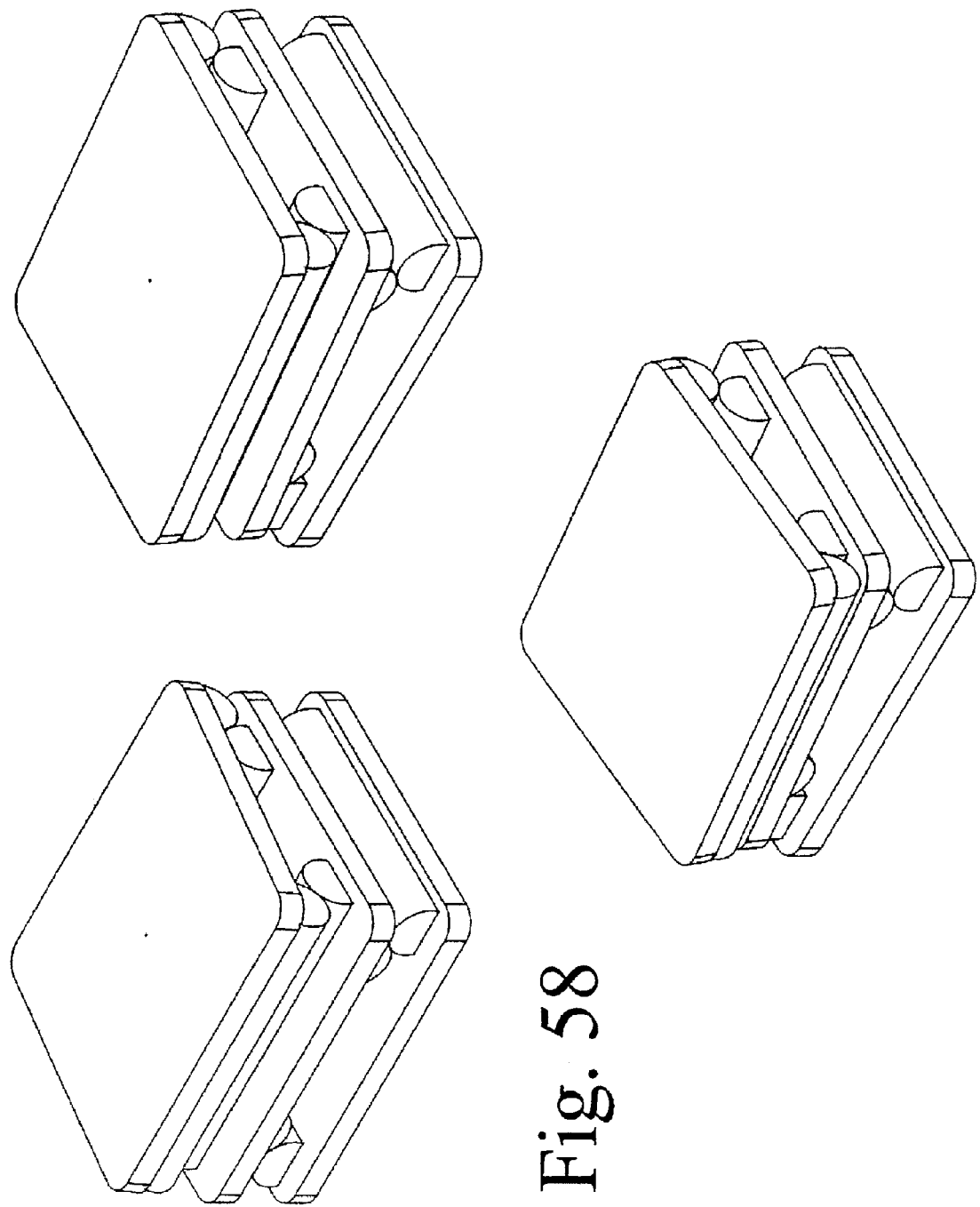
Figure 59:
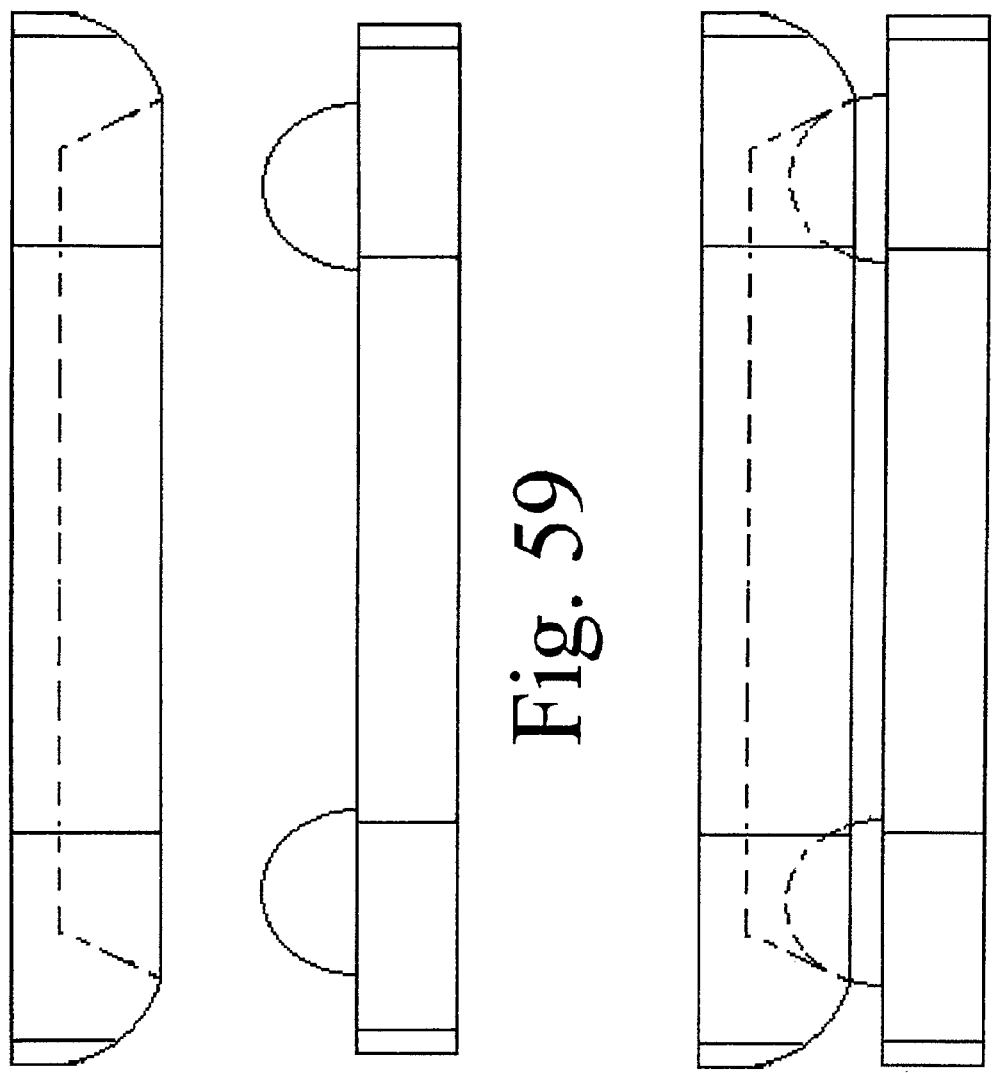
FIG. 59 shows an embodiment wherein one member has an articulation of two substantially cylindrical surfaces and the other member uses a segment of a cone as its articulation surface.

Additional embodiments are illustrated in FIGS. 55 to 58. On FIG. 55, two substantially cylindrical surfaces are placed onto each of the upper and lower device members. The curved movement generated by the articulation is limited to a single plane and is shown in FIG. 56. With the addition of a second, orthogonal articulation surface, the curvilinear movement can occur in two planes as shown in FIGS. 57 and 58. In FIG. 59, an embodiment is shown wherein one member has an articulation of two substantially cylindrical surfaces and the other member uses a segment of a cone as its articulation surface.

Figure 60A:
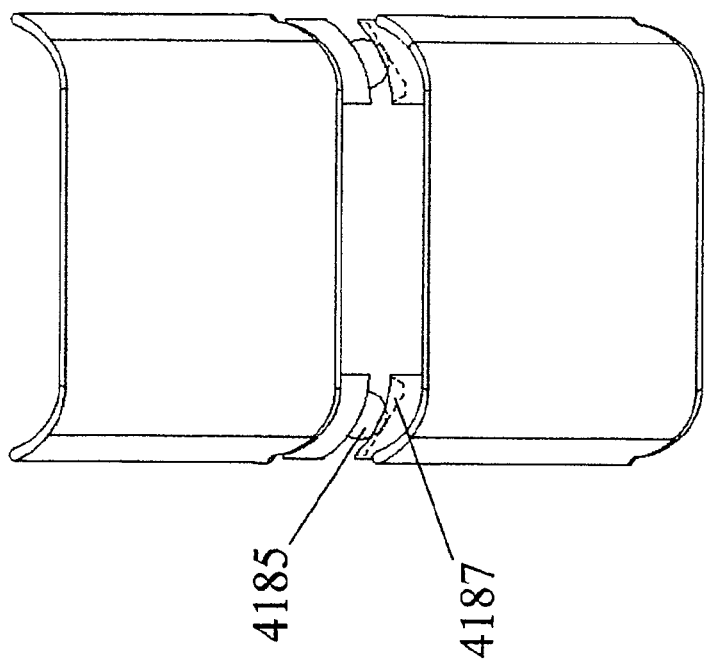
FIGS. 60A and 60B illustrate prosthetic replacement of the uncovertebral joint portion of a cervical disc.
Figure 60B:
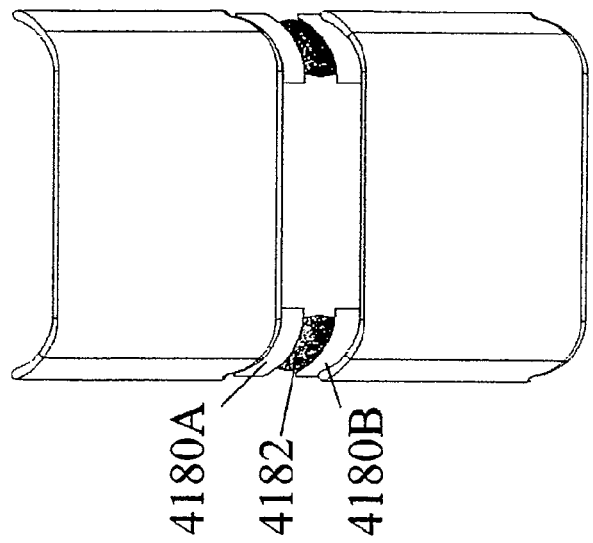

FIGS. 60A and 60B illustrate prosthetic replacement of the uncovertebral joint portion of a cervical disc. In FIG. 60A, each prosthesis has a superior member 4180A and inferior member 4180B. The surfaces of each member 4180 that contact bone are preferably contoured to fit the anatomical constraints of the unco-vertebral joint. A visco-elastic member 4182 is placed between the members 4180 and provides the articulation between the two members. In use, the disc material within the uncoverteral joint is removed. Additional bone resection also may be performed so that the unco-vertebral joint is partially or completely removed. Further, the procedure may be limited to removal of disc/joint material within one unco-vertebral joint or it may be extended to removal of at least a portion of the disc material within the more central regions of the disc space. Finally, the procedure can be performed at one or both unco-vertebral joints at a certain cervical level.

After evacuation of an unco-vertebral joint, removal of the bone spurs, and decompression of the underlying nerve root, the bony surfaces are gently decorticated and the implant is positioned. The procedure and implant permit removal of that portion of the disc space that compresses the exiting nerve root without removal or surgical reconstruction of the entire disc space. FIG. 60B illustrates another deice embodiment. The device has superior and inferior members 4180 but contains a different articulation. A spherical protrusion 4185 extends from the superior member and forms its articulation surface. A cut-out 4187 is formed within the inferior member and serves as its articulation surface. Additional bone fixation features (such as keels, bone screws, bone staples and the like) may be added to supplement device fixation.

FIG. 61 shows a multi-segmental mechanism that improves prosthesis fixation onto the adjacent bone. With rotation of threaded members 7055 (threads not shown), the mechanism drives spiked segment 7058 onto the vertebral body and anchors the prosthesis. Alternatively, the anchoring member can be made of a collapsible segment that buckles and folds at predetermined points with application of a compressive force. Actuating threaded or ratcheted member (similar to 7055) is attached to the collapsible member at a proximal and a distal point. With engagement of the actuating member, the collapsible member is folded and segment of the collapsible is driven into the adjacent bone.

Figure 62:
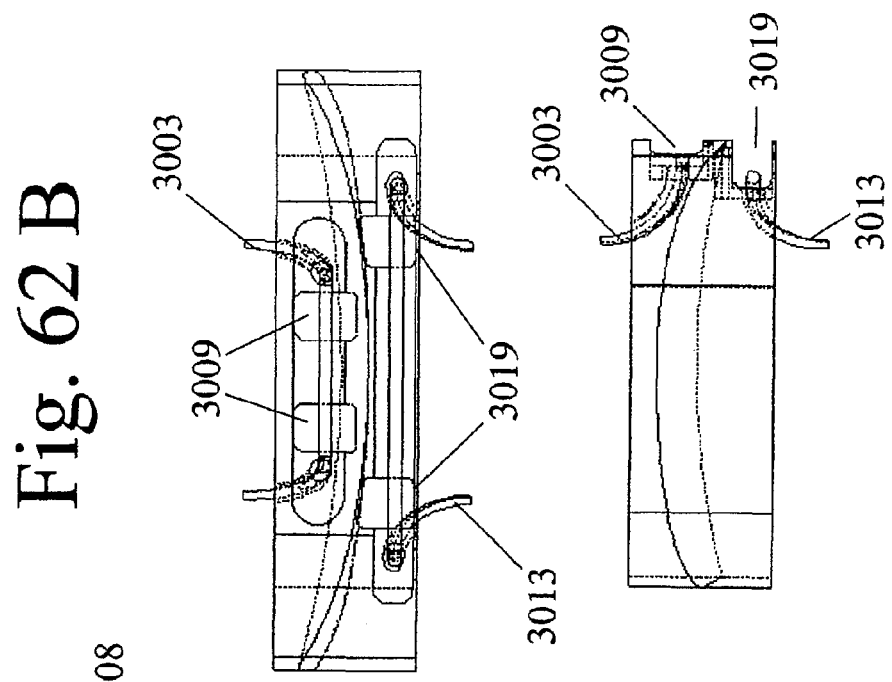
FIGS. 62A and 62B illustrate an additional embodiment of a mobile disc prosthesis.
Figure 62:
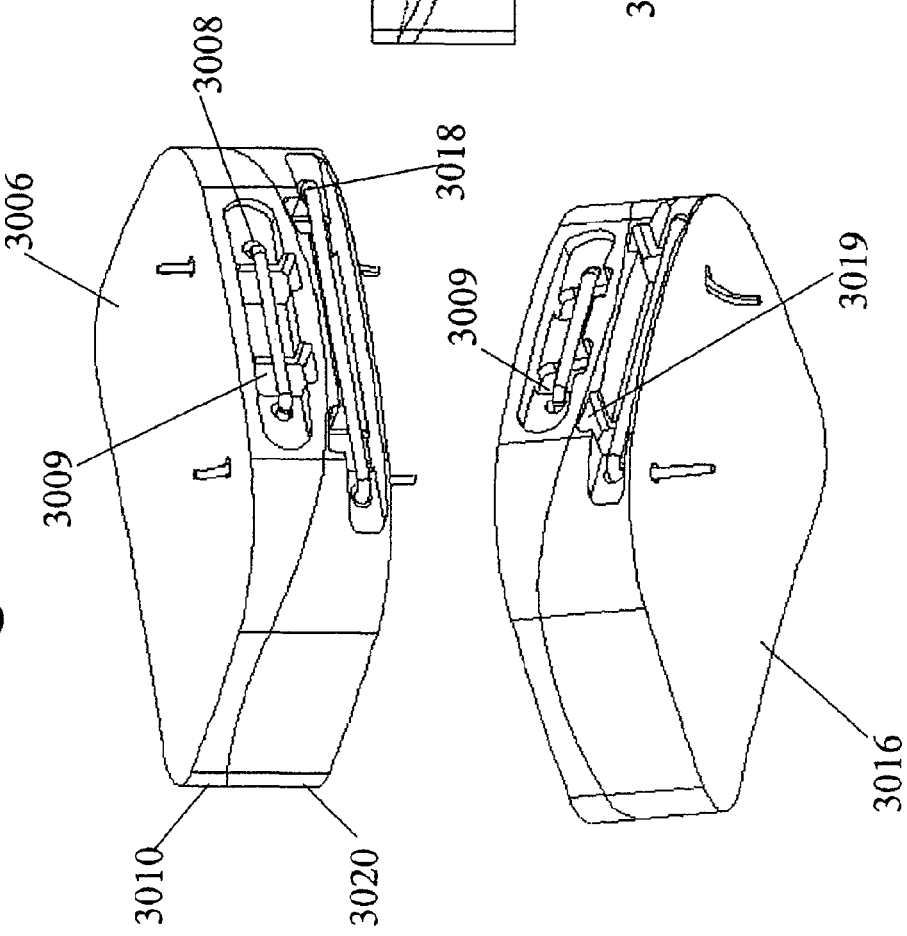

FIGS. 62A and 62B illustrate an additional embodiment of a mobile disc prosthesis. In application, the device is implanted within an evacuated intervertebral disc space. Segments 3010 and 3020 are each anchored to an adjacent vertebral body and an articulation mechanism permits movement between the two segments and the attached vertebral bodies. FIG. 62A shows oblique perspective views of the solid device while FIG. 62B illustrates transparent views. Surface 3006 of segment 3010 abuts the inferior surface of the upper vertebra while surface 3016 of segment 3020 abuts the upper surface of the lower vertebra. Bore holes 3008 and 3018 are located within segments 3010 and 3020, respectively. The bore holes are located on at least one surface of the implant and are preferably curved (but may be alternatively linear). In use, staple 3003 and 3013 are driven through bore holes 3008 and 3018 into the adjacent vertebral bone providing an additional implant anchor. While staples are illustrated, any alternative fastener, such as bone nail, may be employed. Each segment 3010 and 3020 preferably has additional indentations 3009 and 3019 that are adapted to allow a staple placement/removal device (not shown) to interact with the device and the staples.

Figure 63:
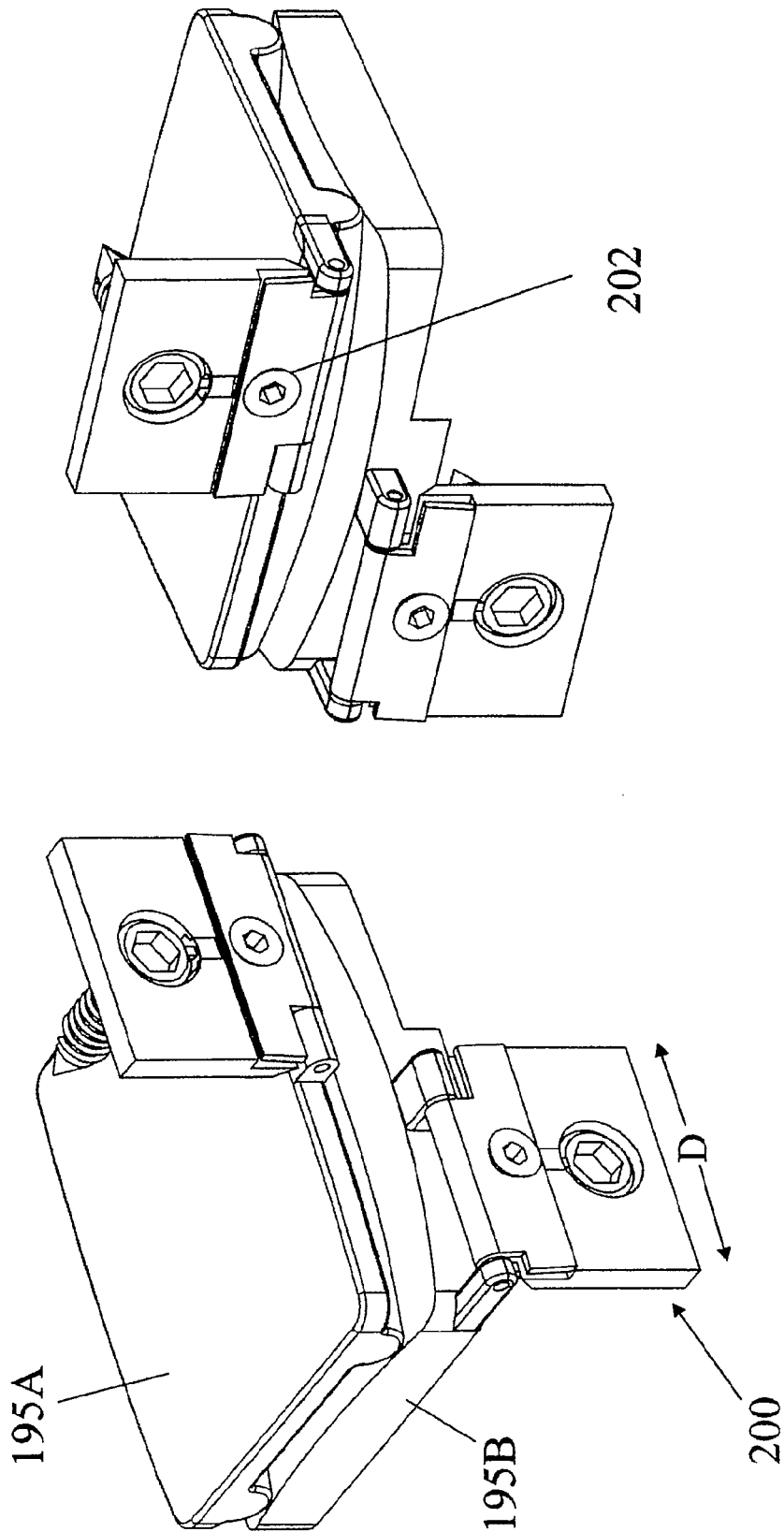
FIG. 63 illustrates an additional method of attachment of a disc prosthesis onto bone.

FIG. 63 illustrates an additional method of attachment of disc prosthesis onto bone. The prosthesis has at least two members 195A and 195B that movably articulate with one another. Each member 195 is attached to a separate vertebral body so that the articulation and motion between the two members provides motion between the vertebral bodies. As shown, an attachment member 200 is rotatably attached to at least one surface of at least one member 195. Member 200 has at least one full thickness bore hole 201 that is adapted to accept a bone fastener, such as a bone screw, and permit fixation of the member 200 onto a vertebral body. The width "D" (side-to side dimension) of member 200 may be greater than, equal to, or less than that of the total width of the surface of member 195 to which member 200 is attached. As depicted, the width of member 200 is preferably less than one half of the width of members 195. Attachment member 200 may rotate about rod member 192 allowing the angle between the each member 195 and an attachment member 200 to vary and to conform to the bone anatomy at the implanted level.

Figure 64:
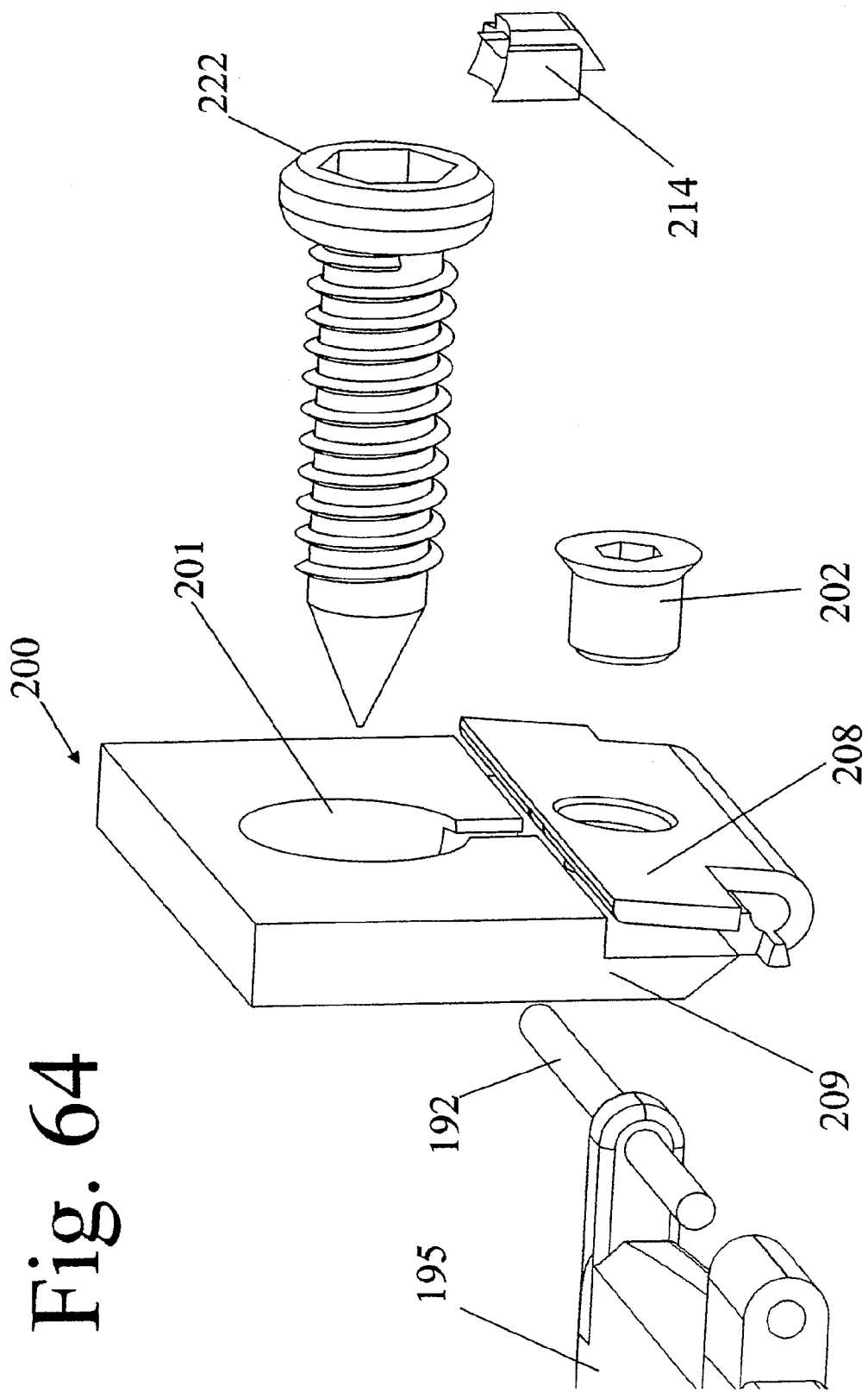
FIG. 64 illustrates an exploded view of an attachment.
Figure 65:
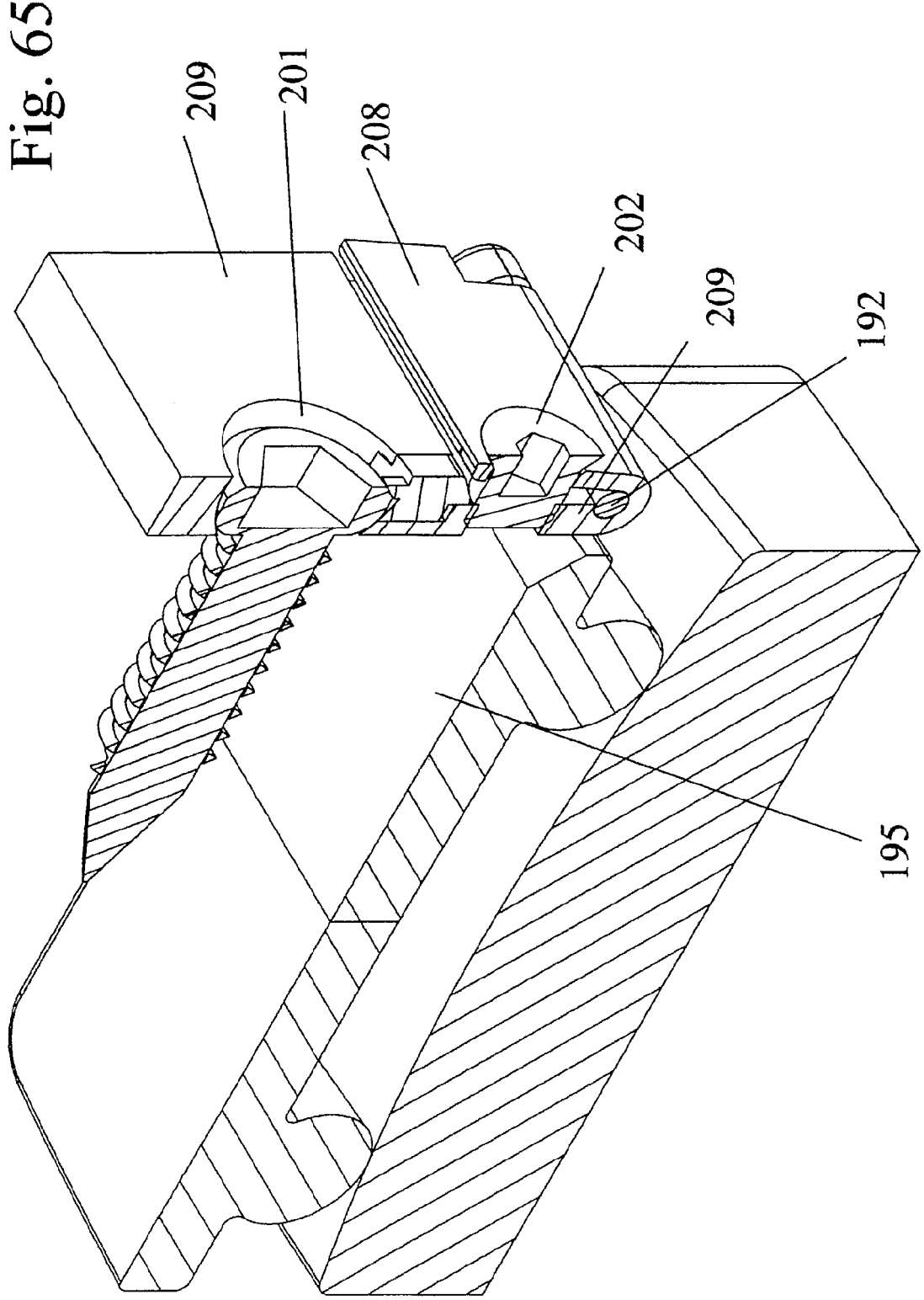
FIG. 65 shows a cross-sectional view of the assembled device of FIG. 63.

An exploded perspective view of the attachment is shown in FIG. 64. An additional threaded screw 202 (threads not shown for diagrammatic simplicity) is illustrated and, when locked, functions to immobilize member 200 relative to rod 192 and thereby lock the angle between members 200 and 195. It also locks the bone fastener and prevents its back-out from bone. FIG. 65 shows a cross-sectional view of the assembled device. With the advancement of threaded locking screw 202, flap 208 and body 209 of the attachment 200 are brought closed together so as to lock the attachment member 200 relative to rod member 192. Since rod 192 is immobilized relative to member 195 at the time of device manufacture, locking attachment 200 relative to rod 192 effectively locks the rotational movement between members 200 and 195. Further, as locking screw 202 advances, it also moves member 214 towards the bone screw 222. As member 214 is wedged against screw 222, the bone screw is locked relative to attachment 200.

Figure 66:
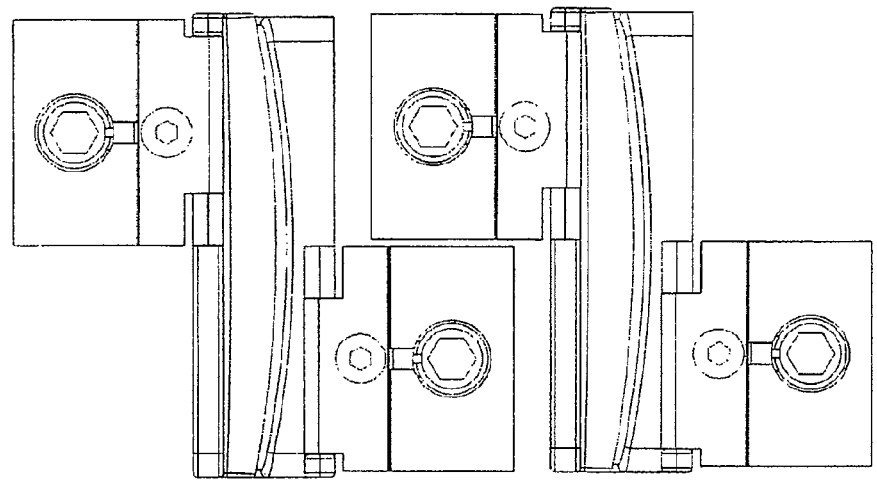
FIG. 66A shows an implanted prosthesis.
FIG. 66B shows an additional disc prosthesis placed at an adjacent segment.
Figure 66:
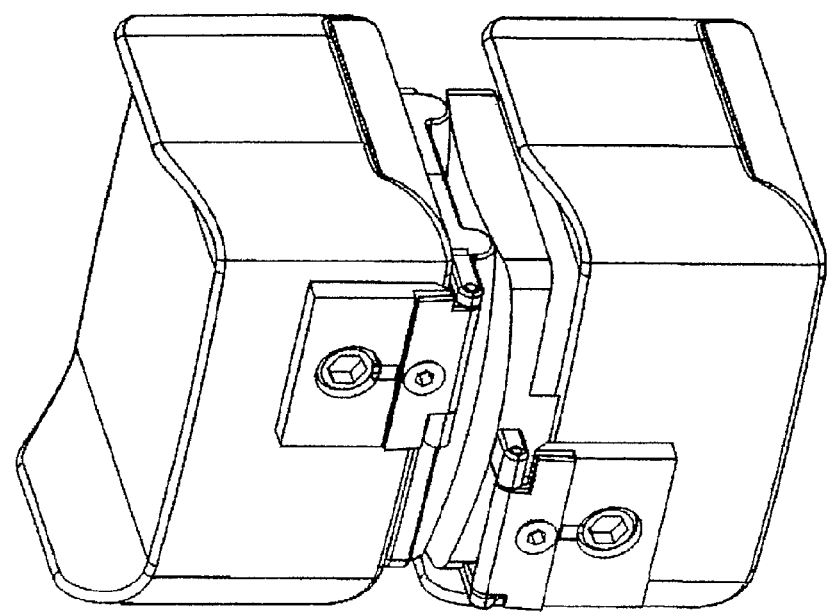

In use, a diseased disc is surgically removed and the prosthesis is placed into the evacuated disc space between two adjacent vertebral bodies. After the device is implanted, attachment member 200 is rotated relative to a member 195 until member 200 is well seated against a bony surface of the vertebral body. The bone fastener 222 is advanced through bore 201 into the underlying bone. Locking screw 202 is then advanced and locked effectively immobilizing member 200, member 295 and bone screw 222 relative to one another. FIG. 66A shows an implanted prosthesis. An additional disc prosthesis can be placed at the adjacent segment as shown in FIG. 66B (vertebral bone not shown).

Figure 67:
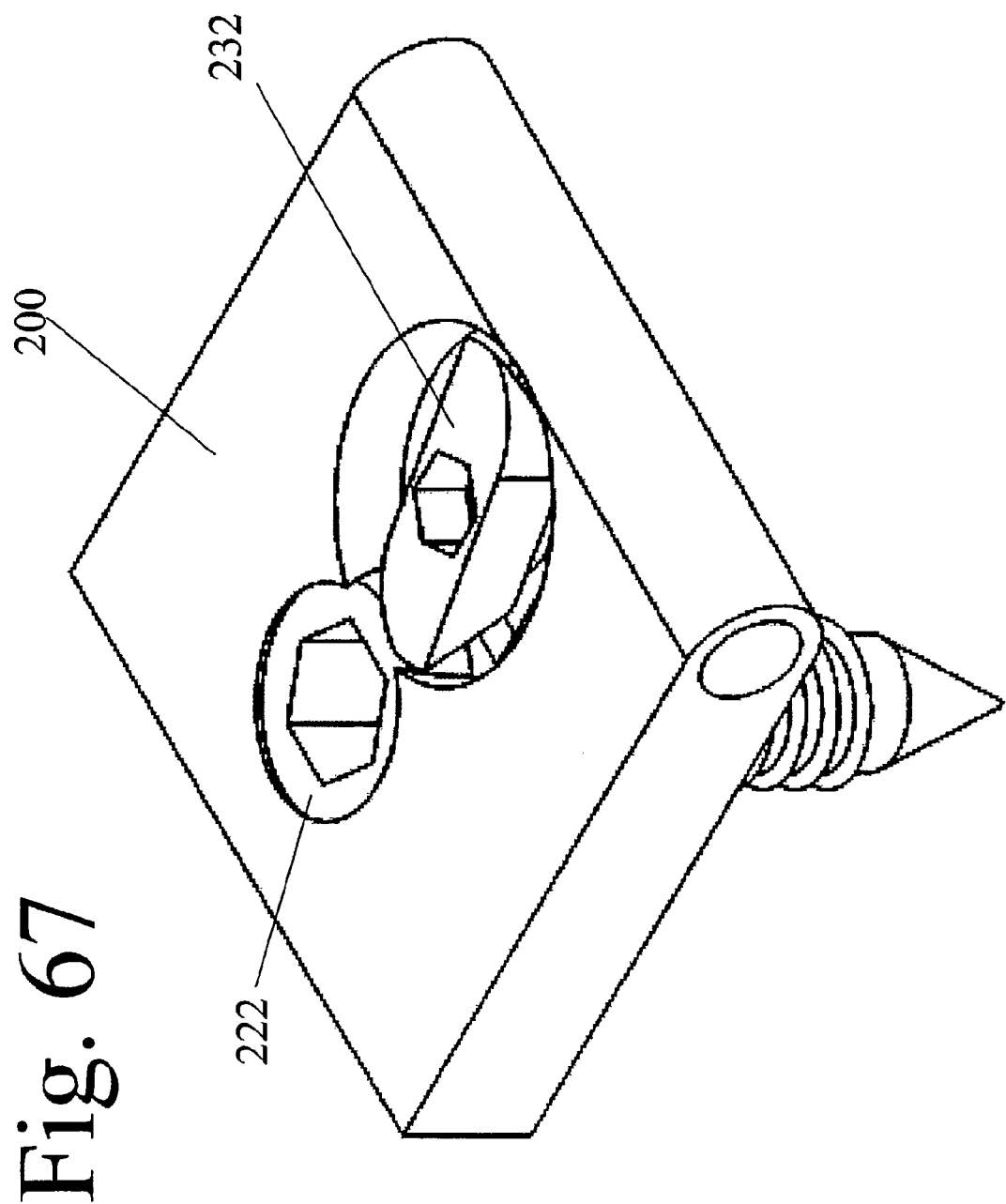
FIG. 67 illustrates an alternative embodiment of the locking screw shown in FIG. 64.
Figure 69:
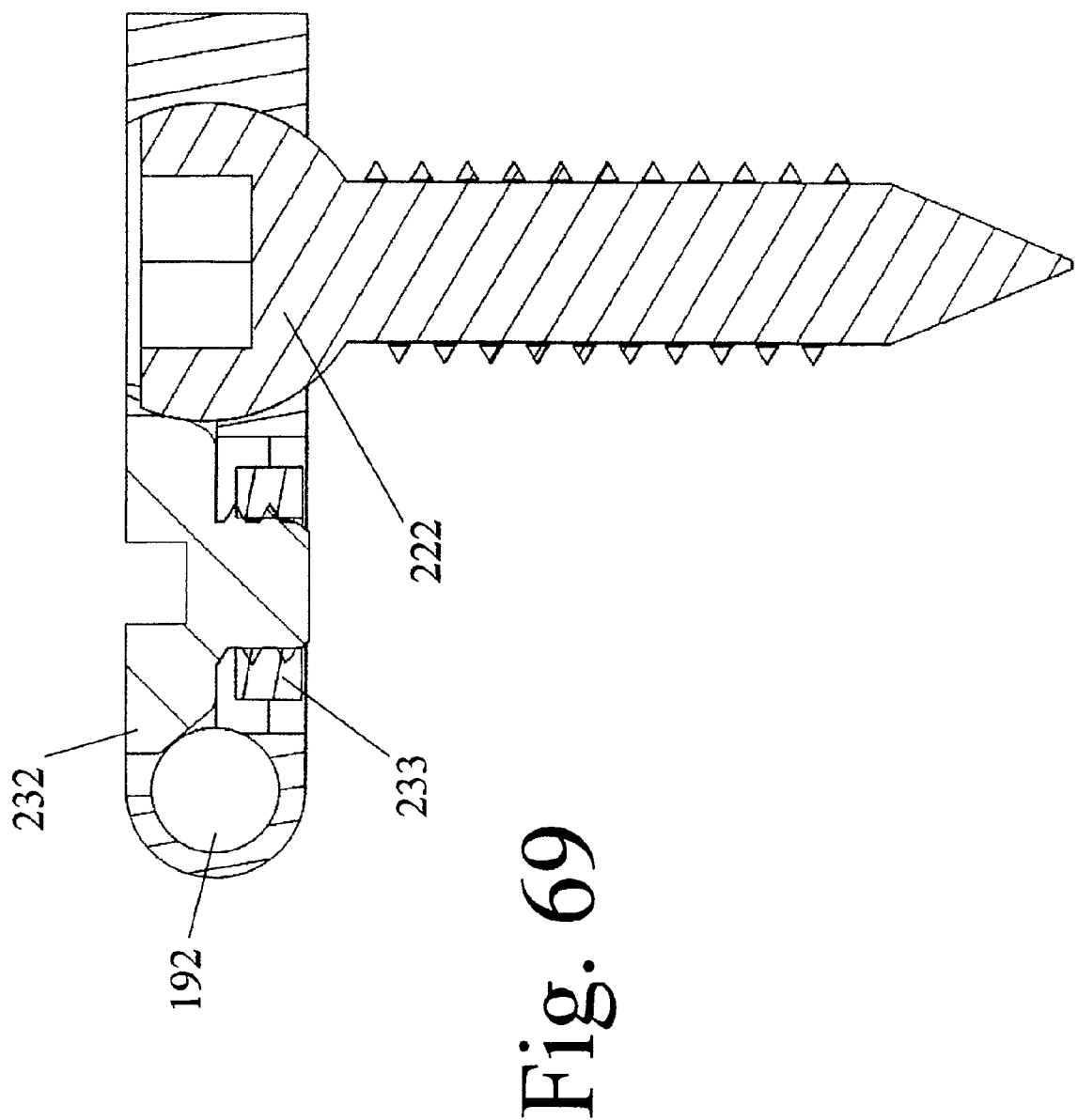
FIG. 69 shows a cross-sectional view of the device of FIG. 68A.
Figure 70B:
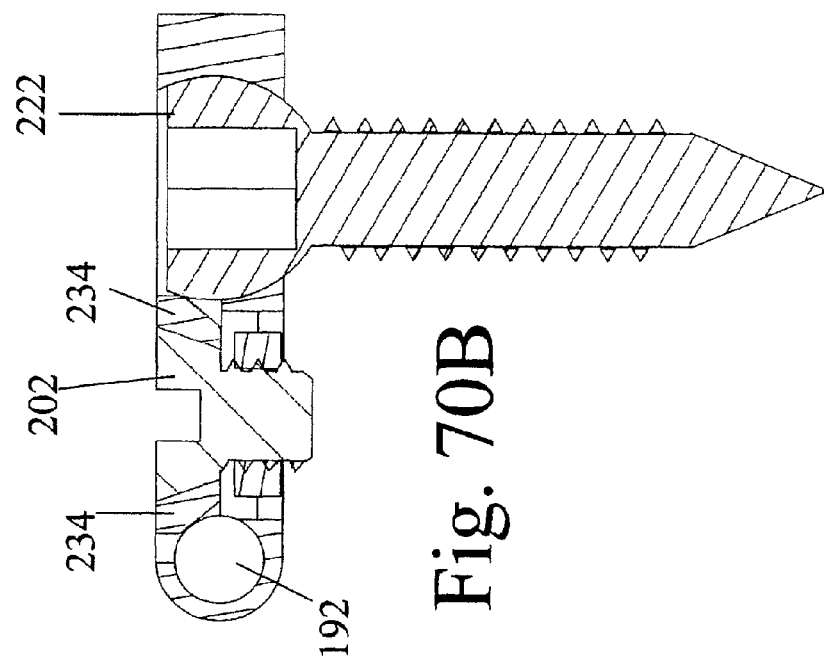
FIGS. 70A and 70B show an alternative locking mechanism.
Figure 70A:
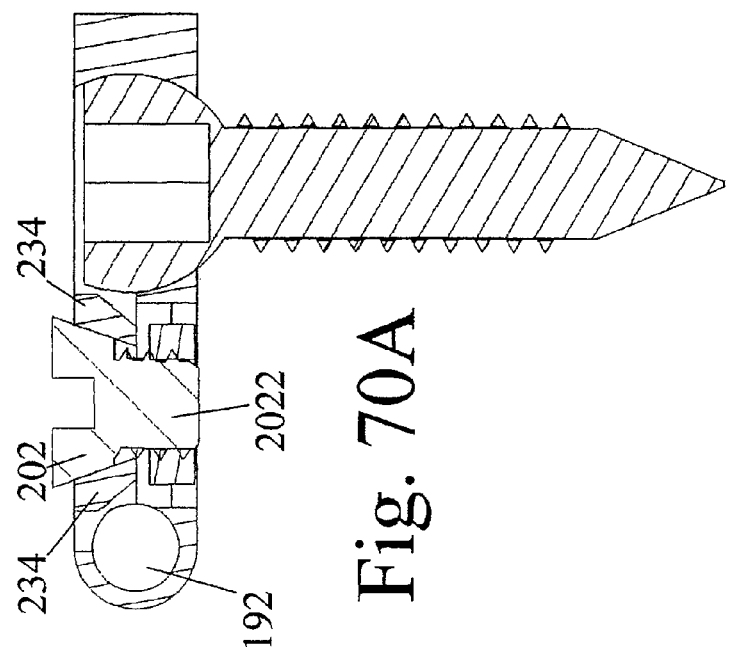

FIG. 67 illustrates an alternative embodiment of the locking screw 202 shown in FIG. 64. In this embodiment, a rotatable member 232 can be rotated form a first unlocked state to a second locked state. FIGS. 68A and 68B illustrate partially exploded views of member 200 with rotatable member 232 and its complimentary attachment member 233. In a first state (unlocked), member 232 does not make contact with rod 192 or bone screw 222. With rotation into a second state (locked), member 232 is wedged between screw 222 and rod 192 immobilizing screw 222 and members 200 and 195 relative to one another. The locked state is shown in a perspective view in FIG. 67 and in a cross-sectional view in FIG. 69. An additional embodiment of a locking mechanism is illustrated in FIGS. 70A and 70B. An expandable "C" ring 234 is situated around a threaded screw 202. FIG. 70A shows the mechanism in a first state (unlocked) in which ring member 234 is not in contact with rod 192 or bone screw 222. With advancement of threaded screw 202, the mechanism is shown in a second state (locked) in which ring member 234 is expanded and wedged between rod 192 and bone screw 222 thereby immobilizing screw 222 and members 200 and 195 relative to one another.

Figure 71:
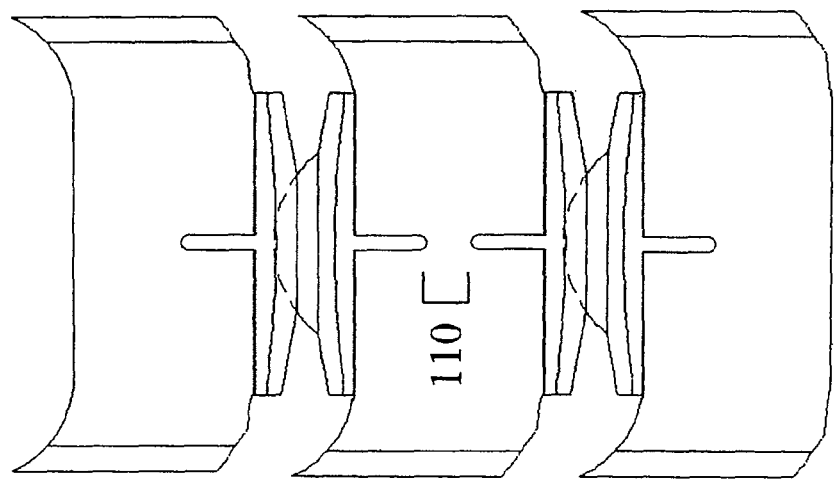
FIG. 71 illustrates an artificial disc prostheses implanted into each of two adjacent disc spaces.

FIG. 71 illustrates an artificial disc prostheses implanted into each of two adjacent disc spaces. Each disc prosthesis has two articulating members with a keel attached to each articulating member. As shown, a small island of bone 110 lies between the top of one keel and the bottom of the second keel.

Figure 72:
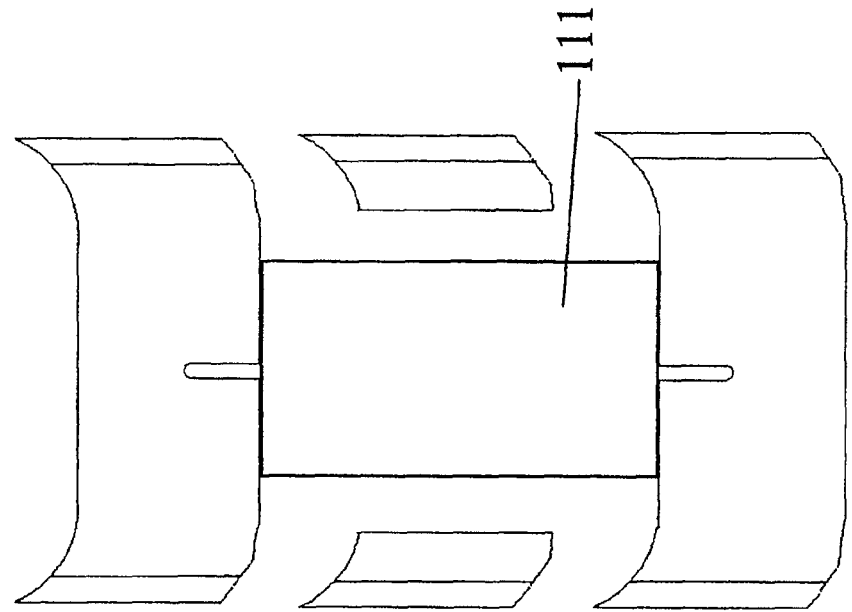
FIG. 72 shows the fractured vertebral fragments necessarily removed and motion segments fused using a bone graft.

Island 110 functions as a bone bridge between the two sides of the vertebral bone and this sliver of bone is subject to fracture. Once fractured, the vertebral fragments can not support the artificial discs and the implants must be removed. The fractured vertebral fragments are necessarily removed and the motion segments are fused using a bone graft 111—as shown in FIG. 72.

As an advantageous alternative to fusion, several embodiments of the present invention function to repair the fractured bone and retain the implanted disc prosthesis. FIG. 73A shows perspective views of one embodiment while FIG. 73B shows the device attached to the fractured vertebral body with the artificial disc prosthesis' in place. The device is made up of body 2000 with one or more bore holes 2010 that are adapted to accept bone screws or similar fasteners. A posterior protrusion 2020 emerges from body 2000 and has three sides with an open central cavity 2030. In application, protrusion 2020 is guided into the fractured vertebral body (preferably, but not necessarily, in the proximity of the fracture line) with body 2000 lying upon the anterior aspect of the fractured vertebral body. The bore holes 2010 are positioned onto each side of the fracture line. The sides of protrusion 2020 are preferably configured to compliment the keel edge of each artificial disc such that, in use, the keel on each disc rests upon an upper and a lower side of protrusion 2030. Bone screws or similar fasteners are used to attach the device to the bone on either side of the fracture. Alternatively, screws can be directed across the fracture line in order to further co-opt the bone fragments. Screws positioned across the fracture line may be placed through bore holes 2010 or they may be used independent of the device (i.e., by themselves).

Figure 74B:
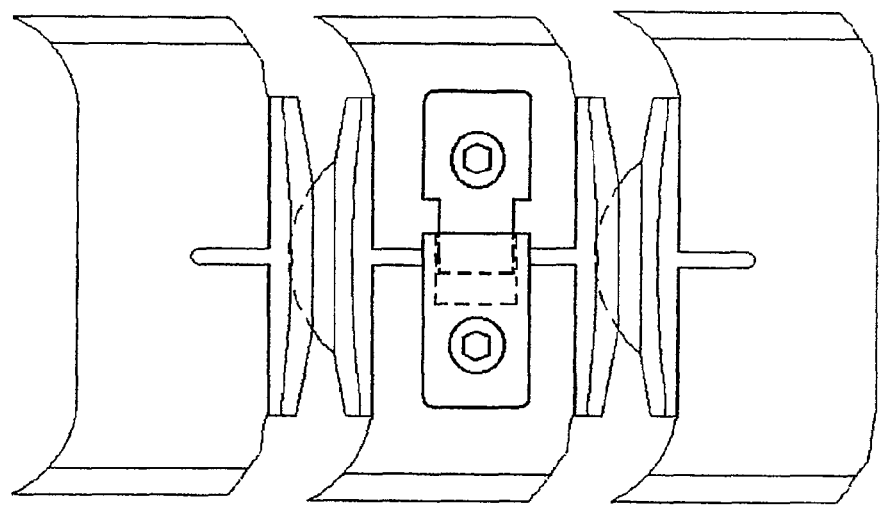
Figure 74A:
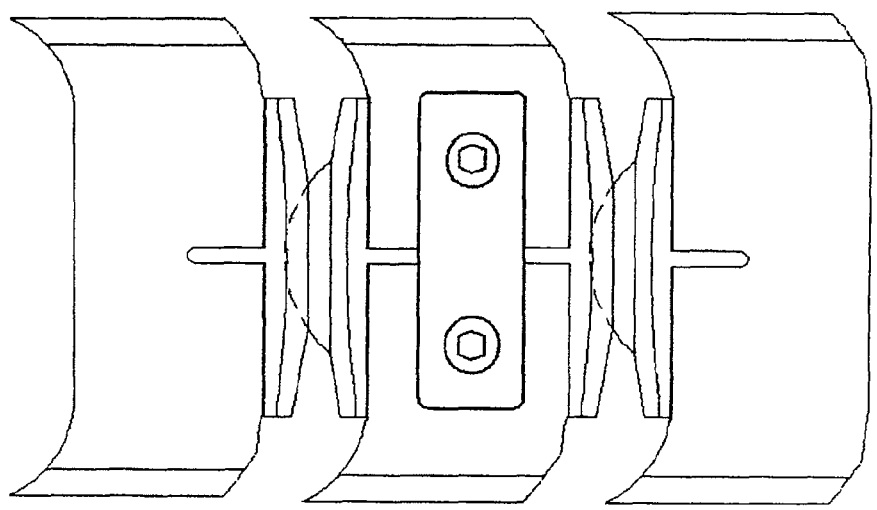

With the device in place, the vertebral bone fragments are held in position by body 2000 while the prosthetic disc devices are supported by protrusion 220 of the embodiment. While body 2000 prevents the anterior migration of the keel portions of the disc devices, cavity 230 provides an open conduit for fracture healing across the vertebral midline. FIGS. 74A and 74B illustrate alternative embodiments of a device used to repair the vertebral fracture(s) while retaining the prosthetic disc devices. In FIG. 74A, a bone plate without a posterior protrusion is placed across the surface of the fractured vertebra. By supporting the vertebral body and preventing migration of the fractured fragments, the plate stabilizes the segments and allows the vertebral end-plate to support the artificial disc implants. The plate also prevents the anterior migration of the keel portion of the prosthetic devices. In FIG. 74B, a sliding plate configuration is employed to produce a plate of variable length and add a compressive load onto the fractured bone fragments. Application of a compression force across a bony fracture is known to accelerate bone healing.

While not depicted, a laterally positioned bone attachment device, such as a plate or screw/rod construct, can be similarly placed onto the lateral aspect of the vertebral body to support the fractured vertebras. In that situation, the bone screw(s) may be advantageously placed across the fracture line and used to further co-opt the fractured fragments. Further, laterally placement bone screws, with or without a bone attachment device, can be used to capture and immobilize the fractured bone fragments on either side of a fracture line. Lastly, FIG. 74C illustrates a method to support and immobilize the fracture fragments from a posterior approach by inter-connecting bone screws placed across the vertebral midline at one or more levels.

Figure 75A:
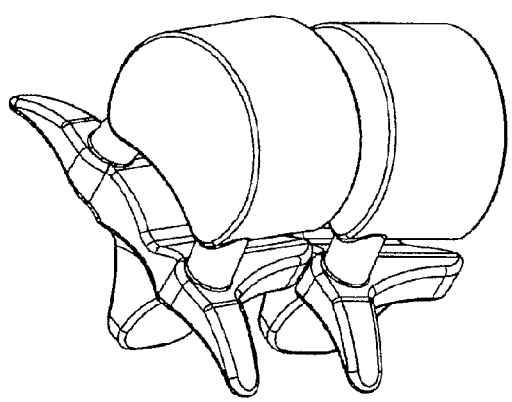
FIGS. 75A-75C show an abnormal alignment between the vertebral bodies.
Figure 75B:
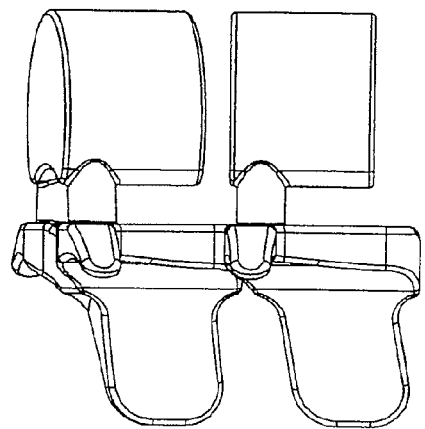
Figure 75C:
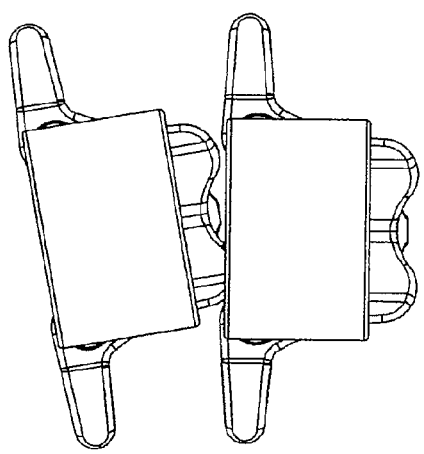

FIGS. 75A-75C show an abnormal alignment between the vertebral bodies. The illustrated vertebras are misaligned in the coronal (medial to lateral) plane so that the vertebral bodies are abnormally angled towards each other on one side and away from each other on the other side. The altered alignment is termed scoliosis and the nerve roots that exit at the level of the misaligned vertebral bodies can be trapped and compressed by the tilting bones. While the nerves on the side with the bones angled towards each other are commonly compressed, the nerve roots on either side may be affected.

Figure 76A:
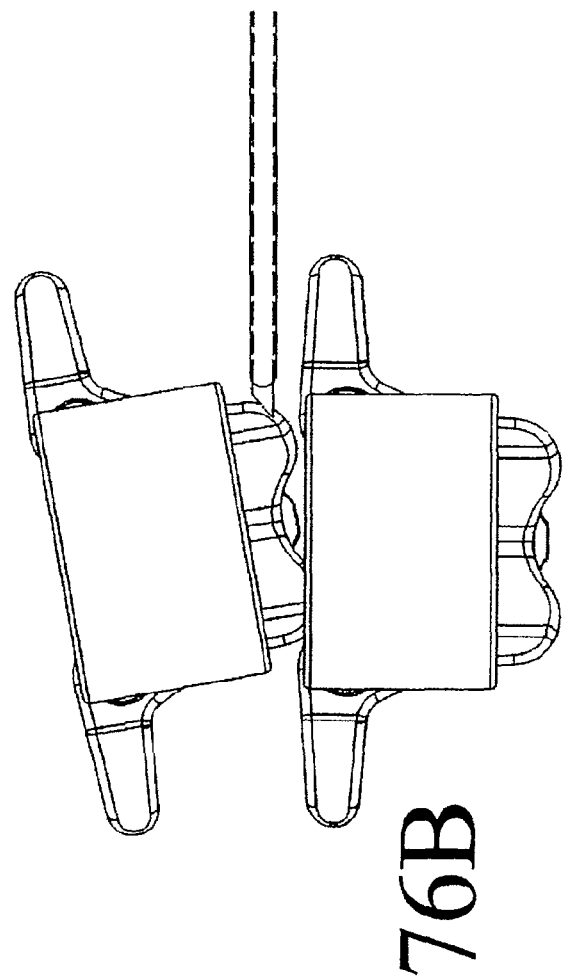
FIGS. 76A and 76B illustrate placement of an expandable spacer between the vertebral bodies on the side with the bones angled towards each other.
Figure 76B:
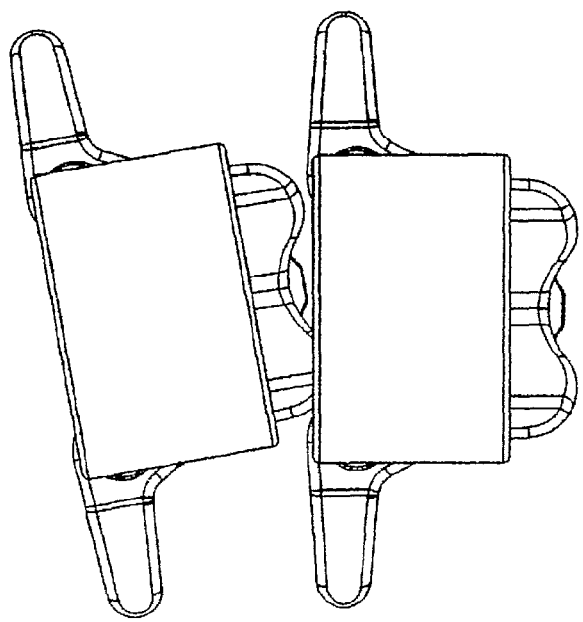

FIGS. 76A and 76B illustrate placement of an expandable spacer between the vertebral bodies on the side with the bones angled towards each other. The spacer distracts the vertebral bodies on the settling side so as to return the bones to a more anatomical spatial relationship. The device is advantageously placed through the side opposite to that of settling side (FIG. 76B) since this generally provides an open corridor for device placement across the vertebral midline and into the region of greatest vertebral proximity. However, the device may be alternatively placed using any appropriate surgical corridor—such as an anterior, lateral or posterior approach or combinations thereof. The device is not intended to lock or fuse the bones together. That is, the vertebral bodies are free to move relative to one another but can not return to the original position of abnormal alignment with the spacer in place.

The device is preferably delivered to the appropriate level via a conduit and using minimally invasive surgery. The device has an initial configuration and, after delivery to the desired position, the device is reconfigured into a secondary form. Preferably, the first form is of a reduced size and adapted to pass through the placement conduit while the second configuration is of a larger size. After delivery, the configuration change occurs after air, fluid or a bio-compatible material is insufflated into the device. Alternatively, the device can be made of an expandable material that enlarges with implantation. Lastly, the device may be made with deformable or movable sub-components that can be actuated after delivery so as to realize the second configuration.

Figure 77A:
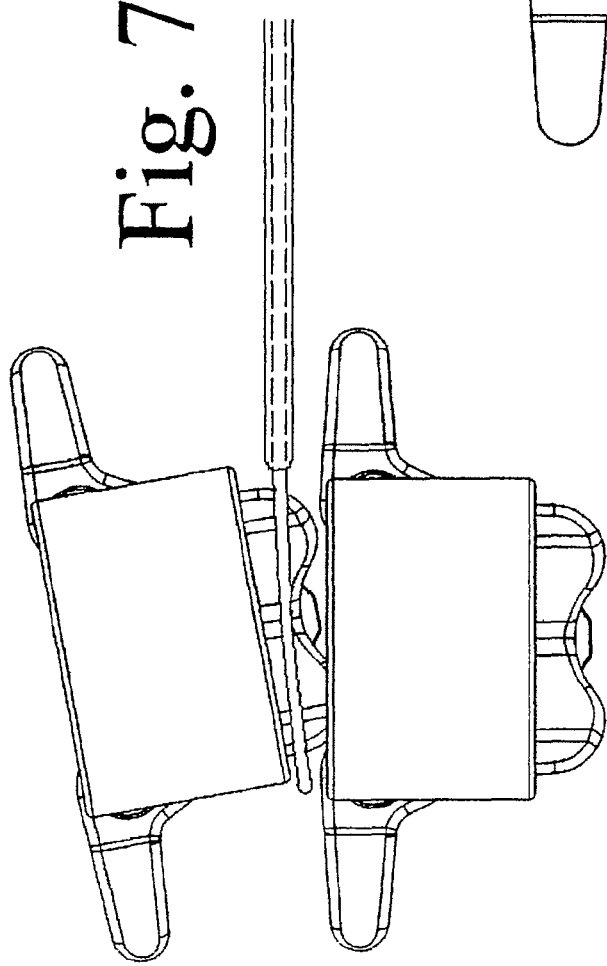
FIG. 77A shows a needle removed and a catheter with a balloon attached to the tip and advance across the disc space and onto the proximity of the device implantation position.
Figure 77B:
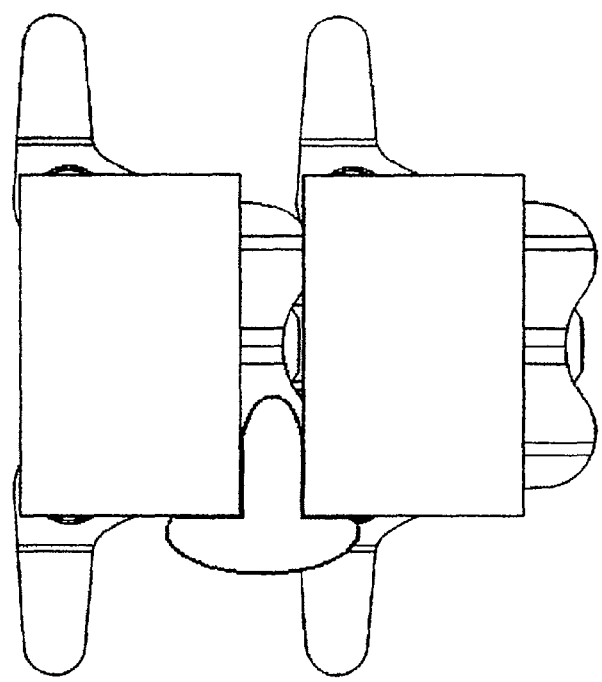
FIG. 77B shows the prosthesis in an implanted state.

FIG. 76B shows an outer conduit with an internal needle or similar sharp component adapted to separate tissue. The device is preferably percutaneously placed at the lateral aspect of the vertebral disc between two misaligned vertebral bodies. The needle is removed and a catheter with a balloon attached to the tip is advance across the disc space and onto the proximity of the device implantation position (FIG. 77A). After appropriate positioning, the balloon is insufflated with air, fluid or a bio-compatible material causing the balloon to conform to the local anatomy and forcefully re-align the two vertebral bodies. The implanted device is shown in FIG. 77B.

FIGS. 78A and 78B illustrate an additional embodiment. Device 2700 has a tough but malleable bag-like outer member 2702 and is partially filled with solid bead-like members 2704. At least one port 2706 resides on the surface of member 2702 and contains a valve 2708 within it. The device 2700 exits in a first state (FIG. 78A) in which the outer member 2702 contains members 2704 as well as ambient room air. Alternatively, member 2702 may contain members 2704 interspersed within a gas or a liquid environment. In this state, the device is malleable and can be molded into any desired configuration. It may be also delivered through a small tube to the site of desired implantation. After the device is molded into the desired configuration, the surrounding air/gas/liquid is removed by the application of suction through port 2706 and the device exists in a second, non-malleable state (FIG. 78B). Valve 2708 maintains the vacuum even after removal of the vacuum source. With evacuation of the gas/liquid, the rigid bead members 2704 coalesce together to form a rigid device. The beads 2704 may be simply and reversibly held in proximity by the application of suction or they may be fused together by chemical, electrical or magnetic forces. That is, beads 2704 may be manufactured with electrical charge and/ or magnetic or chemical properties that increase their attraction to one another. In addition, the beads may be alternatively designed to break on application of suction and release a liquid substrate that mixes with substances released by other breaking beads and transform into a solid state. Many substances, such as resins and the like, may be used to accomplish the liquid to solid state transformation.

In use, device 2700 is delivered to the area of implantation through a surgical cannula. The vertebral mal-alignment is preferably transiently corrected using a second surgical instrument and device 2700 is then placed into the implantation site in a first state (malleable state). Suction is applied through port 2706 and the device is transformed into a second state (non-malleable, rigid state). The surgical instruments are withdrawn leaving the rigid device 2700 to maintain the correction. While this embodiment is illustrated in use as a spacer within the vertebral disc space, it may be alternatively used as a spacer in any other biological application. These applications include but are not limited to inter-spinous process distractors. The device may be also used as a surgical retractor in which the malleable bag is delivered to the site rolled into a cylinder with a balloon catheter (or an expandable cannula) in the center. The balloon is inflated to form the central working cavity within the retractor and the suction is applied to convert the device into the second, rigid state. The balloon catheter is removed leaving a central corridor that can be used to perform the surgical procedure (FIG. 78C). The rigid device retains the soft tissue and keeps the central corridor open.

Figure 79A:
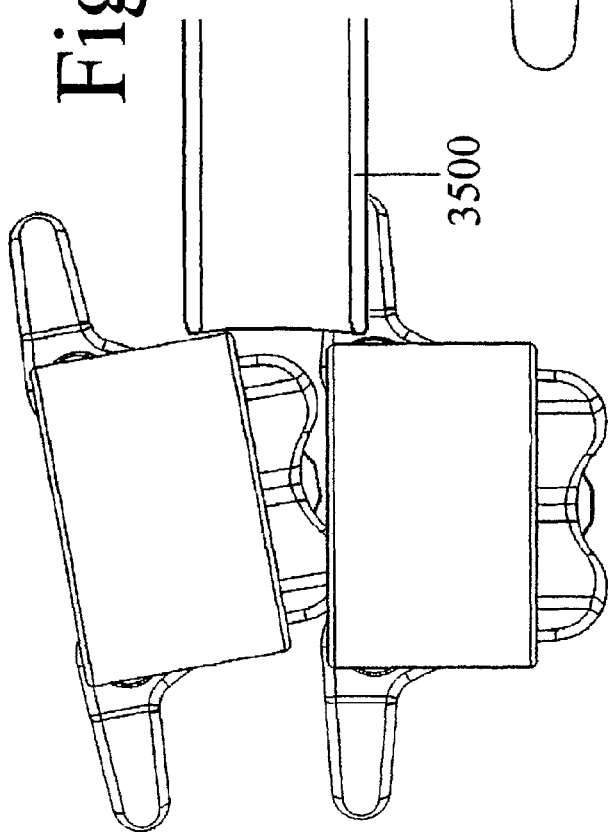
FIGS. 79A and 79B illustrate an additional embodiment of a prosthesis.
Figure 79B:
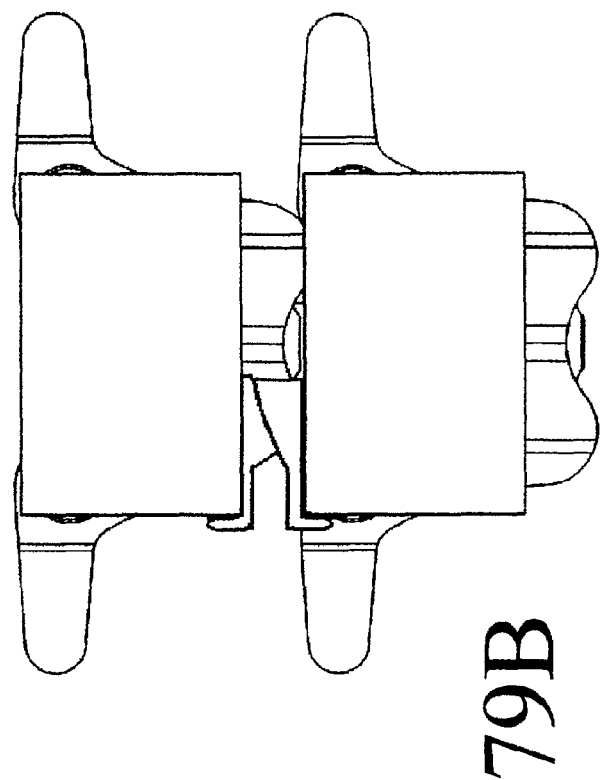

In an alternative embodiment shown in FIGS. 79A and 79B, a surgical retractor 3500 is placed adjacent to the disc space (preferably, but not necessarily, adjacent to the side opposite to that of greatest vertebral proximity) and a disc prosthesis is placed across the vertebral midline into the region of vertebral proximity. The prosthesis may be made of any appropriate design adapted to function as an artificial disc prosthesis. The prosthesis only partially occupies the disc space and is preferably smaller than seventy-five percent (75%) of the total disc space width (dimension form one lateral side of the disc space to the opposite lateral side of the disc space).

Over time, a patient implanted with an artificial disc prosthesis may develop significant pain and neurologic dysfunction, whether from implant malfunction or for other reasons, and require that the two vertebral bodies be immobilized and fused together. Multiple embodiments are disclosed that allow the disc prosthesis to serve as a platform for the fusion of the two vertebral bodies.

Figure 80:
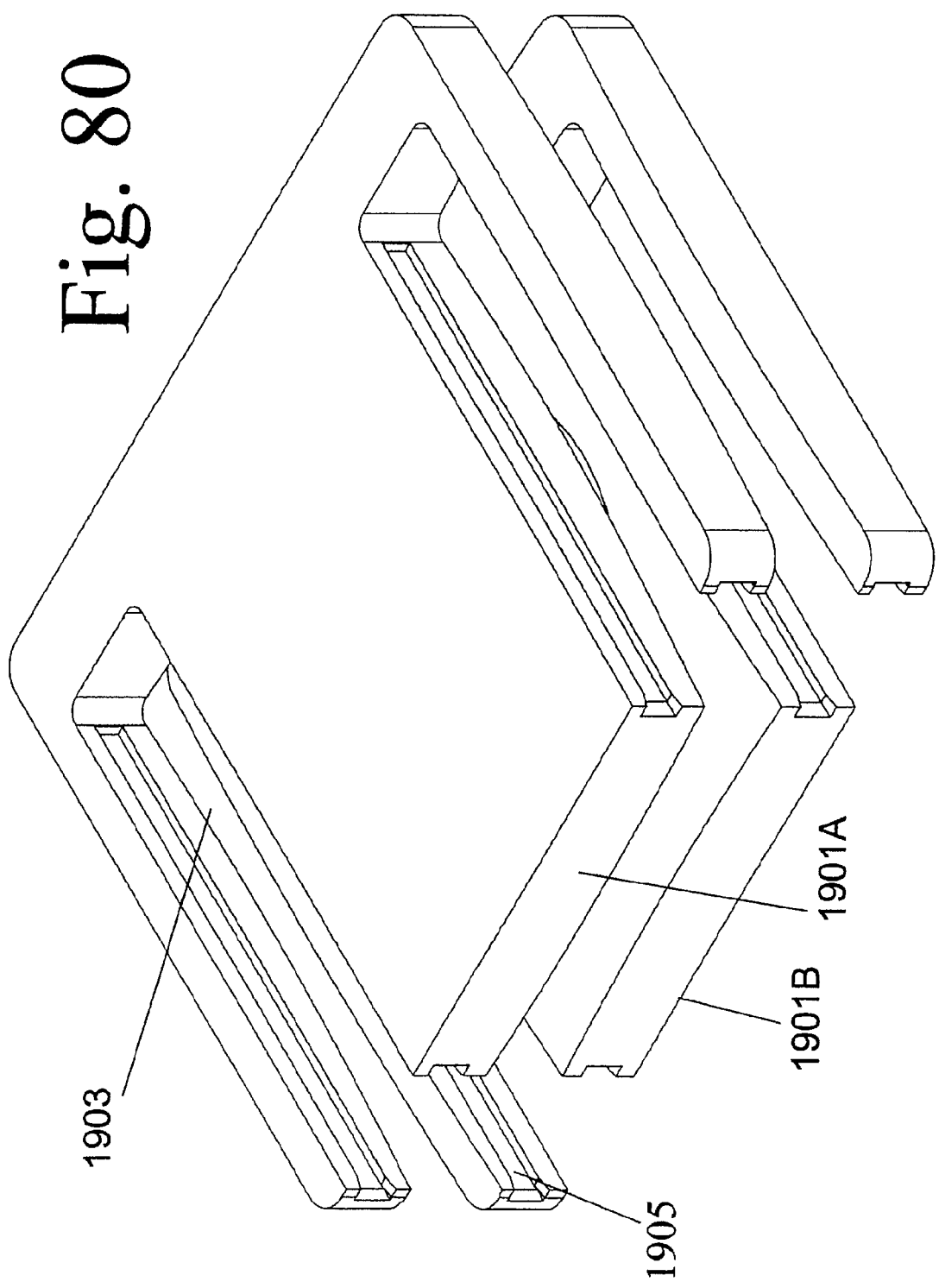
FIGS. 80 and 81 show an embodiment in which an upper segment and/or a lower segment contain an opening.
Figure 81:
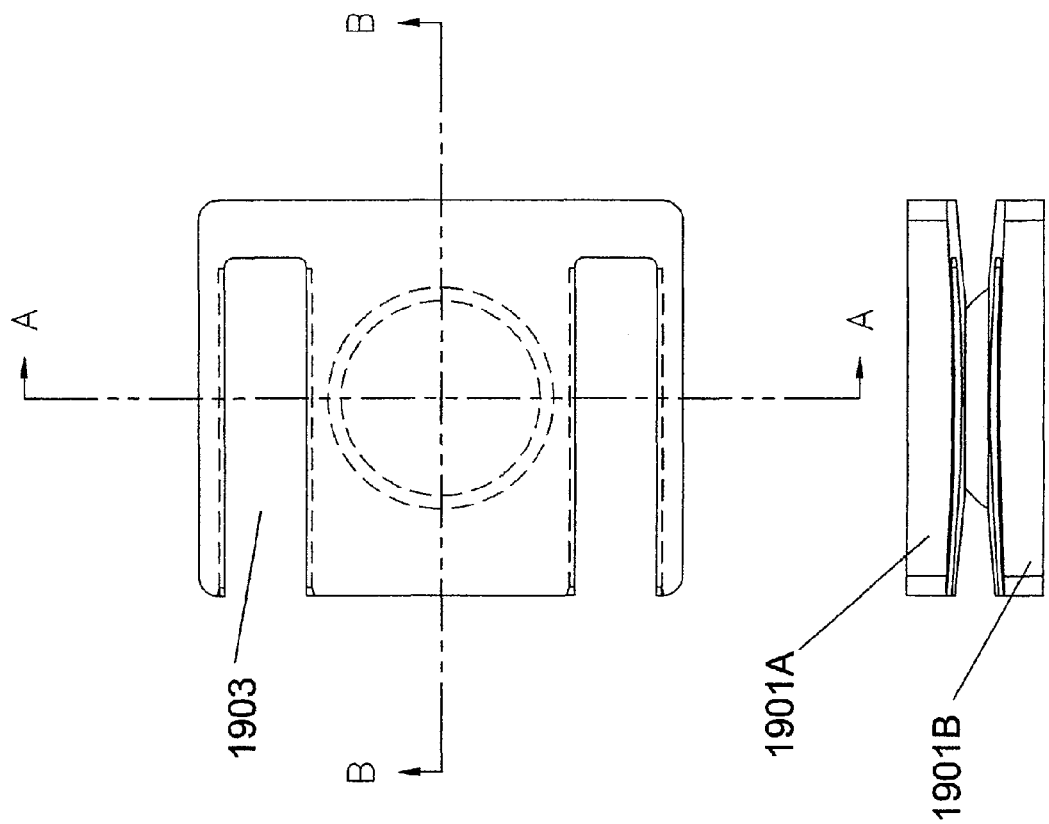

FIGS. 80 and 81 show an embodiment in which an upper segment 1901A and/or a lower segment 1901B contain an opening 1903. While the two segments 1901 are depicted as having a ball-in-socket articulation, it should be appreciated that any applicable articulation may be alternatively used between them. Alternatively, the bearing surfaces may be at lease partially replaced by a malleable member (such as an elastomer, springs, and the like) that permits relative movement between the upper and lower segments 1901. Further, openings 1903 in FIG. 80 are depicted as rectangular in shape but may be comprised of any adaptable shape. Preferably, but not necessarily, openings 1903 comprise of a side wall with indentations 1905 that is adapted to accept a complimentary protrusion from a second device. FIG. 81 shows perspective views of an embodiment of the present invention.

Figure 82A:
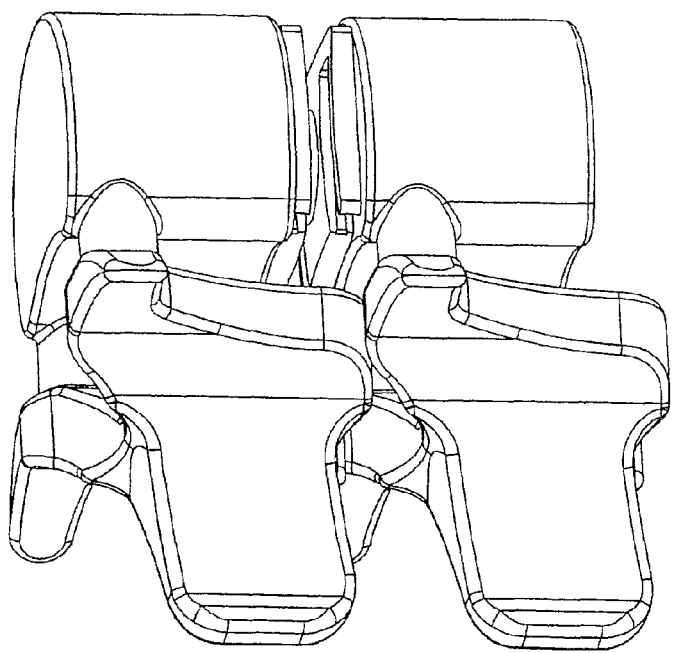
FIGS. 82A and 82B illustrate an exemplary method of use of a prosthesis.
Figure 82B:
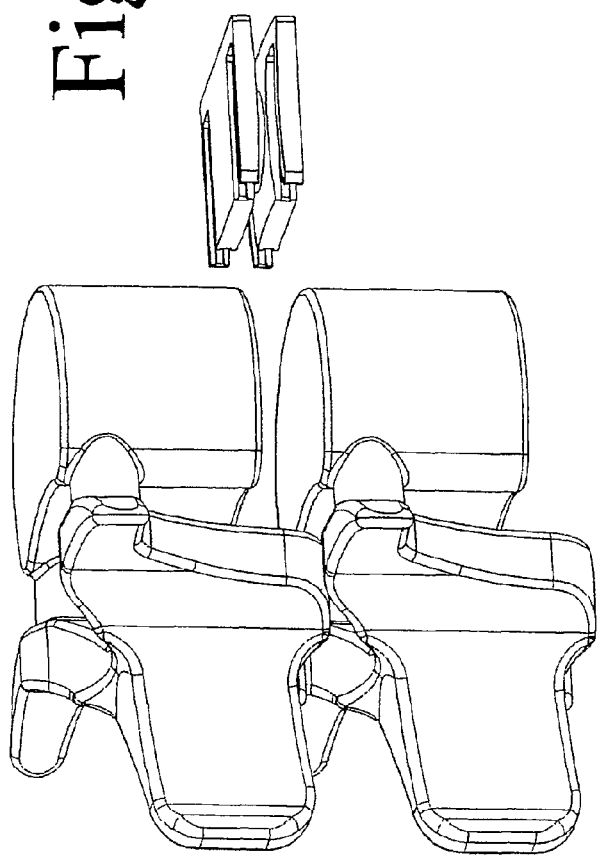
Figure 83A:
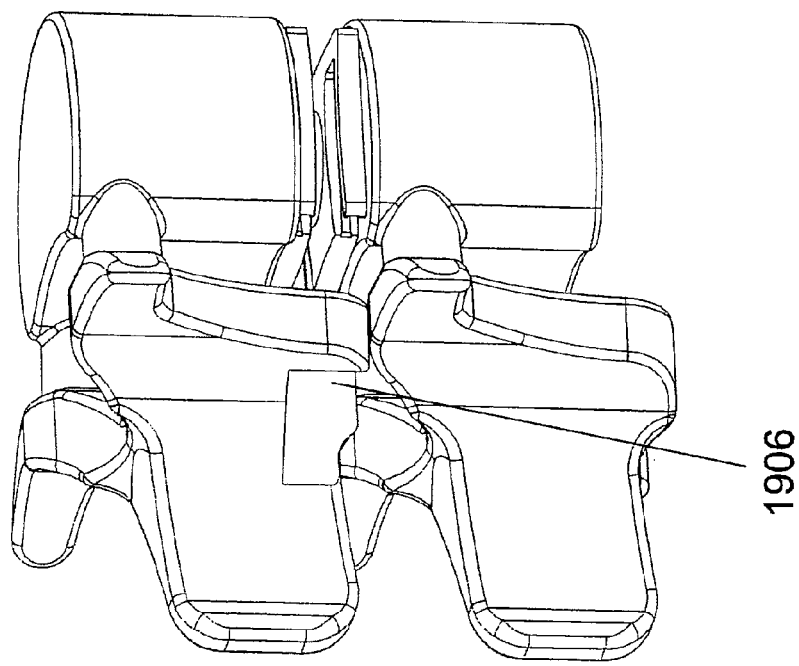
FIGS. 83A and 83B illustrate the surgical formation of holes within the posterior elements of the vertebrae.
Figure 83B:
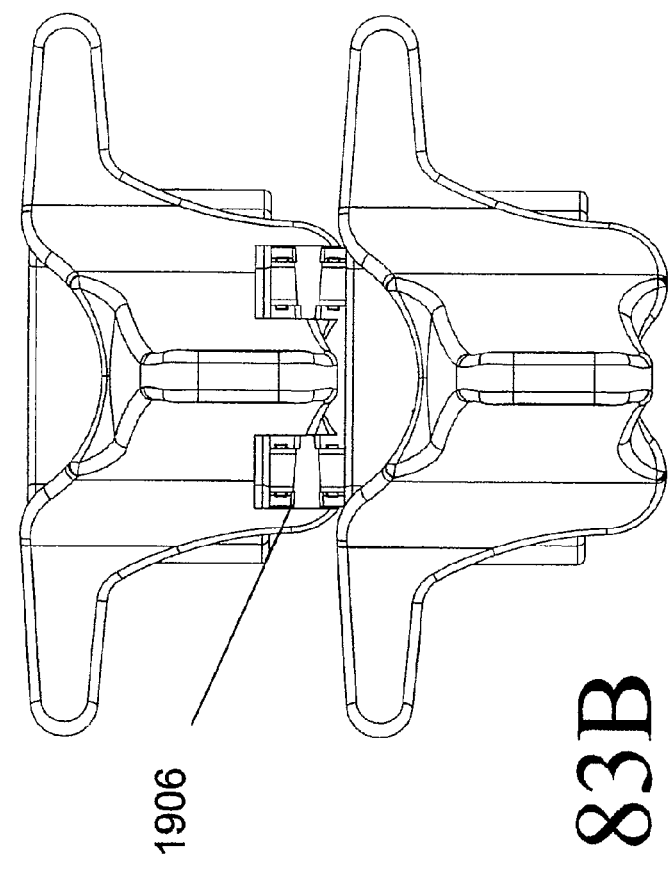
Figure 84:
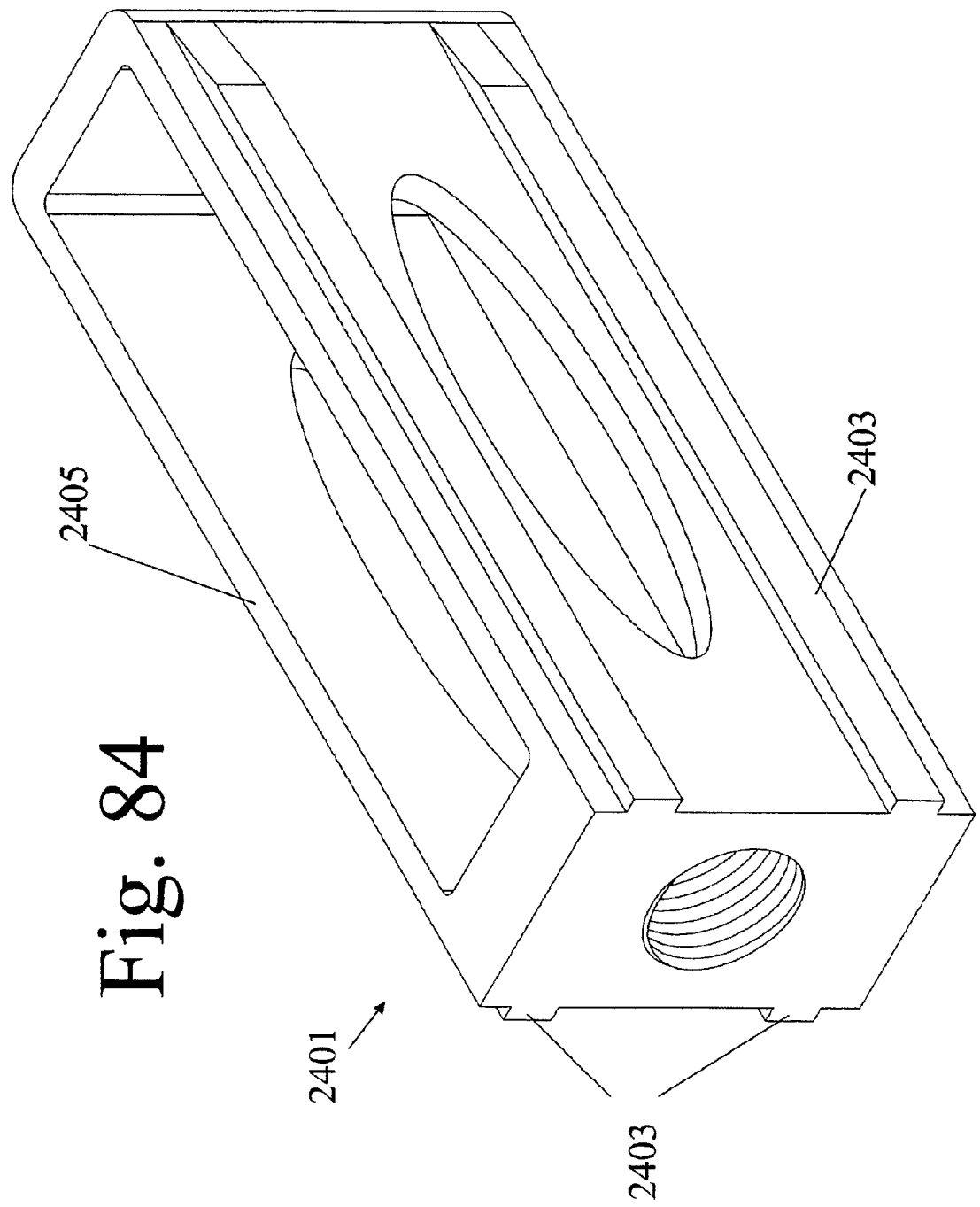
FIG. 84 shows an embodiment of a bone fusion device that is configured to reside within an opening of the disc prosthesis.

FIGS. 82A and 82B illustrate the preferred method of use. In FIG. 82A, the disc between the two vertebral bodies has been at least partially removed. The prosthesis is implanted between the two vertebral and functions to replace the mobile properties of the natural disc—as shown in FIG. 82B. Should the vertebral bodies require immobilization and fusion at a subsequent operation, the device provides a platform for fusion cage and/or bone graft placement. FIGS. 83A and 83B illustrate the surgical formation of holes 1906 within the posterior elements of the vertebrae. These holes provide a corridor that can be used to access the posterior aspect of the disc prostheses. FIG. 84 shows an embodiment of a bone fusion device 2401 that is configured to reside within opening 1903 of the disc prosthesis. In one embodiment, the bone cage 2401 is shaped to fit within the openings 1903 of an upper segment 1901A and a lower segment 1901B. Preferably, the bone cage has an elongated rectangular configuration with a central cavity that is adapted to retain a bone graft and at least one opening that permits communication between the central cavity and the environment outside the cage. Alternatively, any applicable fusion device that is adapted to contain a bone graft/bone graft substitute may be used to within openings 1903 and/or around the outside of the disc prosthesis.

The bone cage 2401 preferably has extensions 2403 that interact and fit within the side wall indentations 1905. The top and/or bottom of the cage 2401 may be further textured to increase bone contact and/or coated with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone in-growth, bone formation, or establish a mineralized connection between the bone and the implant.

The bone cage 2401 is placed within the openings 1903 of an artificial disc prosthesis. FIG. 85A illustrates an embodiment of a disc prosthesis device prior to insertion of the bone cage 2401. FIG. 85B shows the prosthesis after a single bone cage 2401 has been placed within the openings 1903 on each side of the midline.

Figures 86A, 86B, 86C:
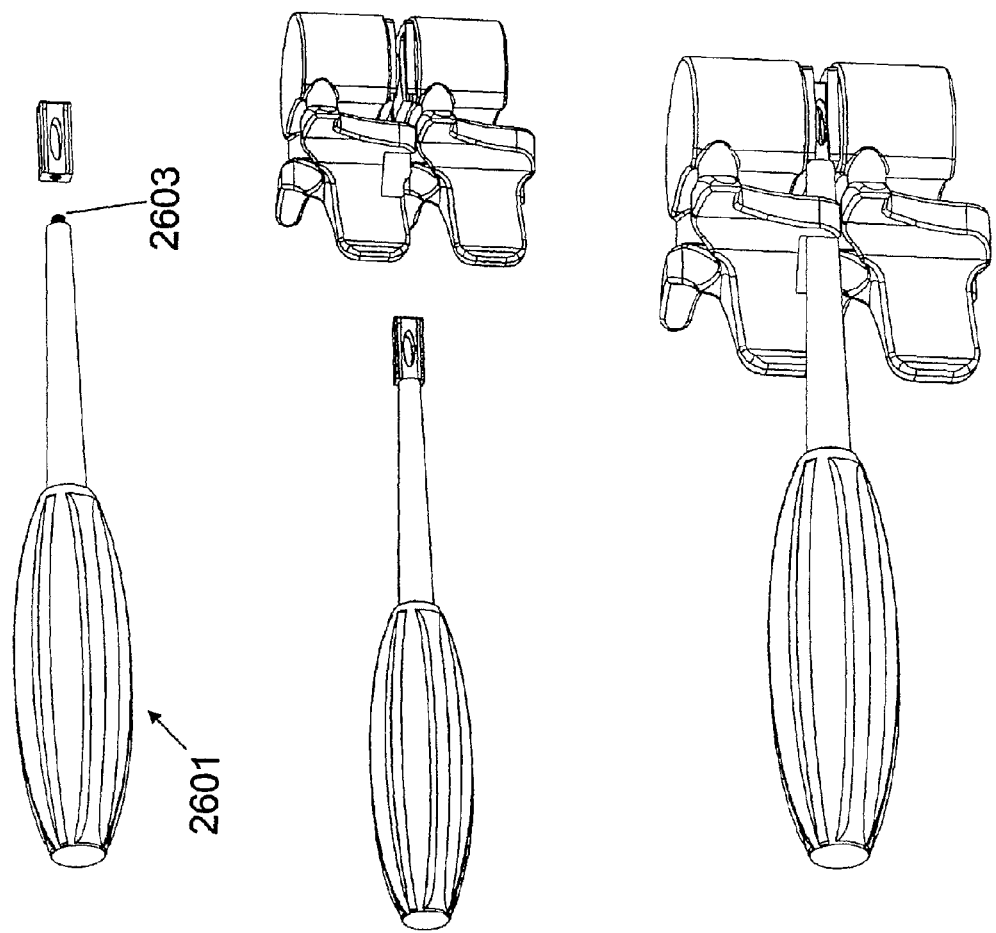
FIG. 86A shows a placement instrument.
FIG. 86B shows a threaded end of the placement instrument attached to a bone cage.
FIG. 86C shows the bone cage placed into an opening.
Figure 87B:
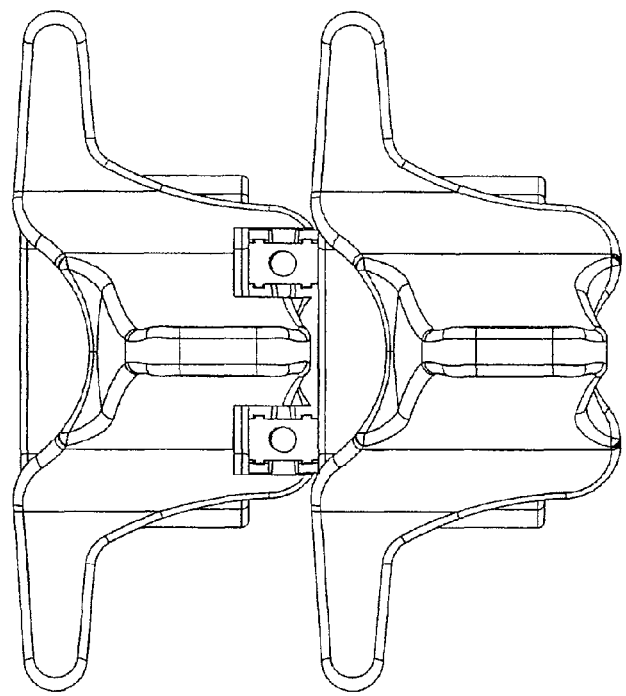
FIGS. 87A and 87B show various views of the artificial disc prosthesis after a bone cage has been inserted into the openings on each side of the vertebral midline.
Figure 87A:
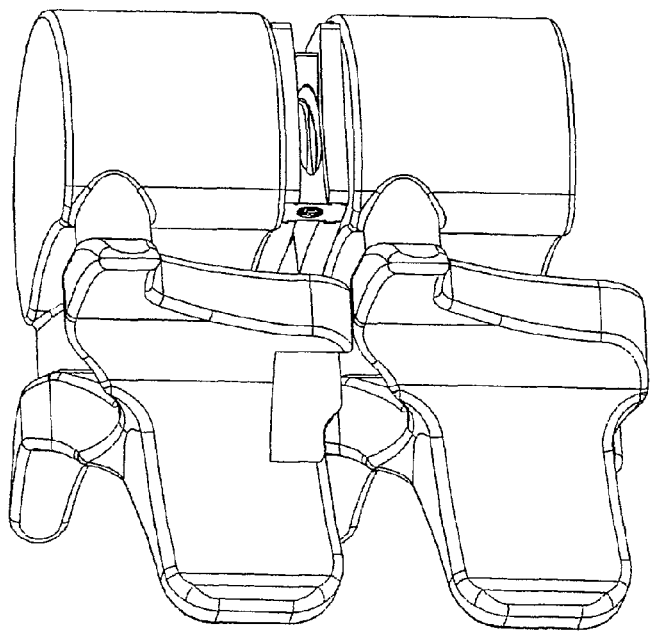
Figure 88:
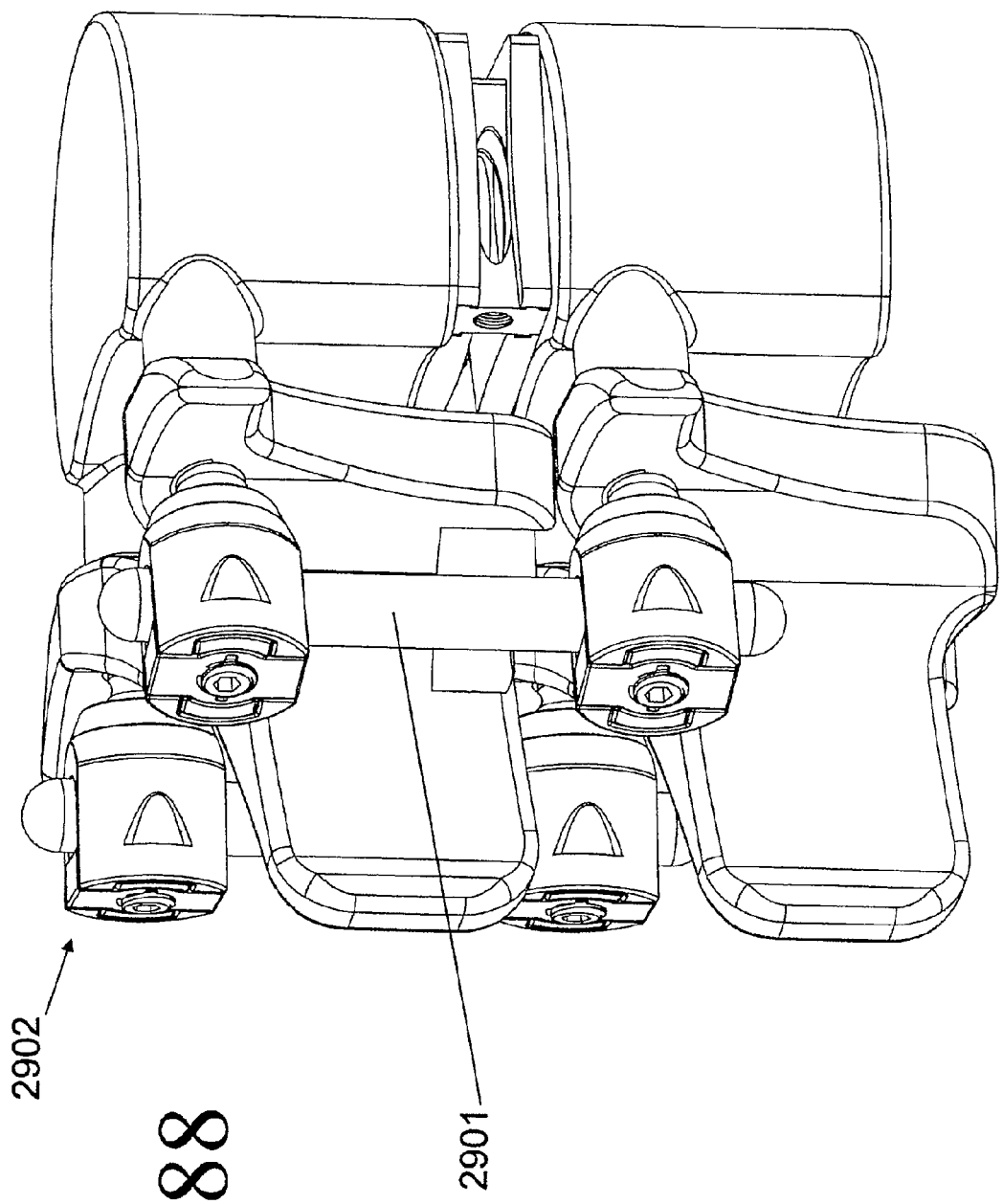
FIG. 88 shows the vertebral bodies fixed together with bone fastener assemblies and an interconnection rod.

FIG. 86A shows a placement instrument 2601. It contains threaded end 2603 that is adapted to interact with a complimentary threaded hole on an end of bone cage 2401. The threaded end 2603 is attached to the bone cage as shown in FIG. 86B. Prior to placement of the fusion cage, the vertebral end plates that underlie openings 1903 of segments 1901 are denuded of soft tissue. The underlying bone is also decorticated in preparation for fusion. The cage 2401 is filled with bone or an appropriate bone graft substitute. With the holding instrument 2601 attached to the cage, the bone cage is placed into opening 1903—as shown in FIG. 86C. FIGS. 87A and 87B show various views of the artificial disc prosthesis after a bone cage 2401 has been inserted into the openings 1903 on each side of the vertebral midline. The vertebral bodies may be also fixed together with bone fastener assemblies and an interconnection rod 2901 as shown in FIG. 88. As illustrated, four screw assemblies 2902 have been inserted into the vertebral bodies. Each screw assembly 2902 provides a means of attaching an interconnecting rod 2901 to the vertebral bodies.

Figure 89:
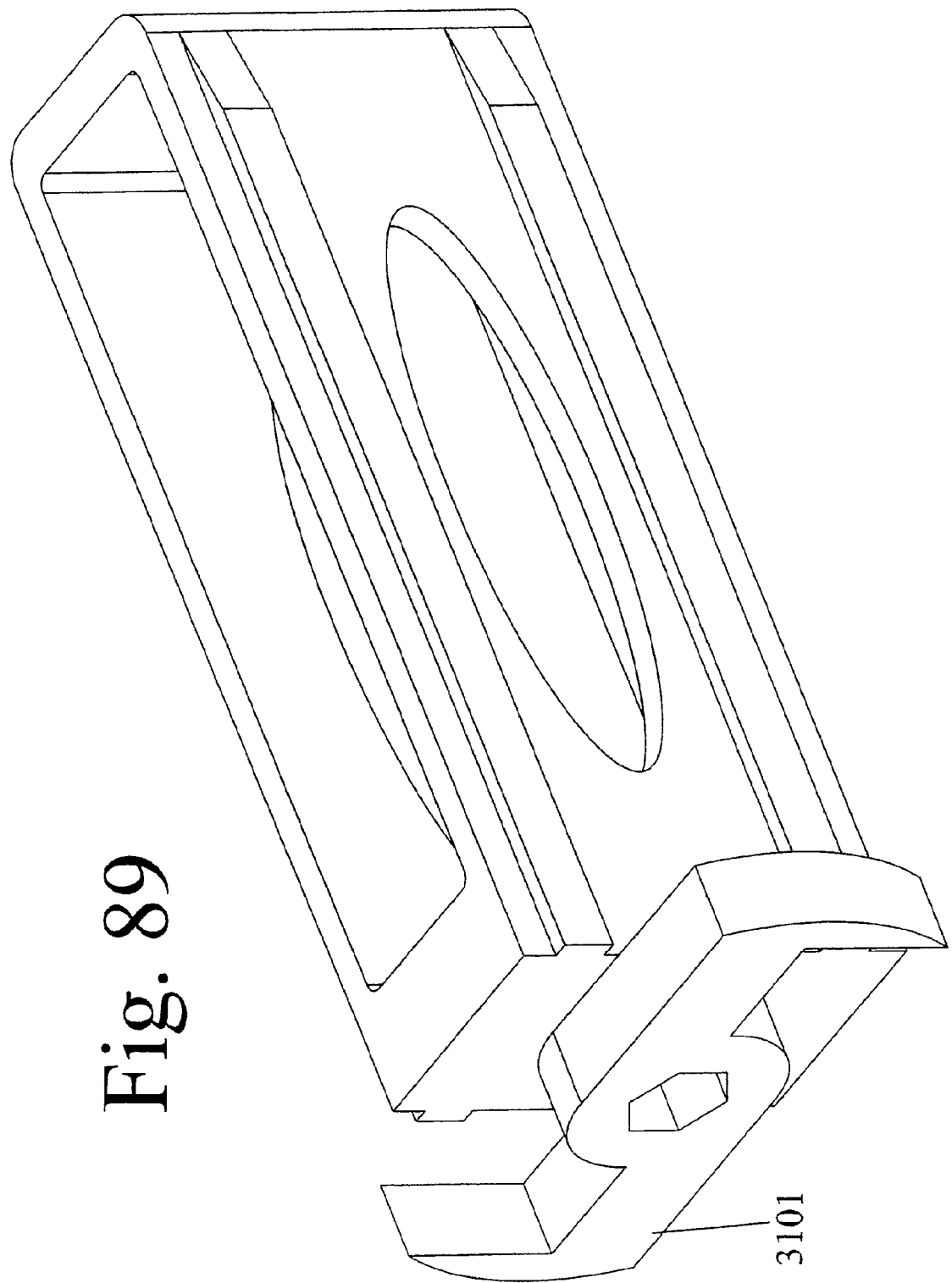
FIG. 89 shows an alternate embodiment of a bone cage.

An alternate embodiment of the bone cage is shown in FIG. 89. The device is comprised of a bone anchor 3101 used to provide additional fixation to the adjacent vertebral bodies. In one embodiment the bone anchor is shaped in the form of the letter "S" as shown in FIG. 89. The bone anchor 3101 comprises of a mechanism to attach the bone anchor 3101 to the bone cage so that rotation of the bone anchor 3101 is achievable. One embodiment of the mechanism is shown in FIG. 90B as element 3203. In FIG. 90A, bone anchor 3101 is shown connected to the bone cage.

Figure 91B:
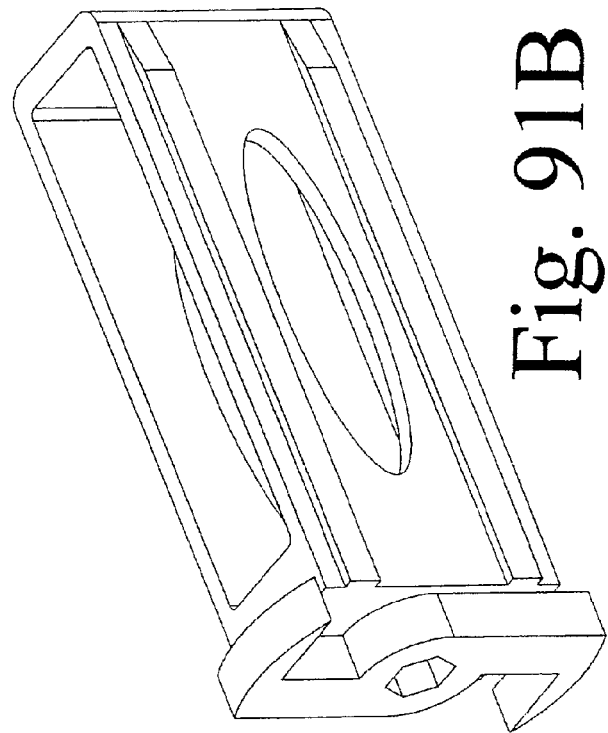
FIG. 91B shows the bone cage and bone anchor placed into an opening within an artificial disc prosthesis with the anchor in the engaged position.
Figure 91A:
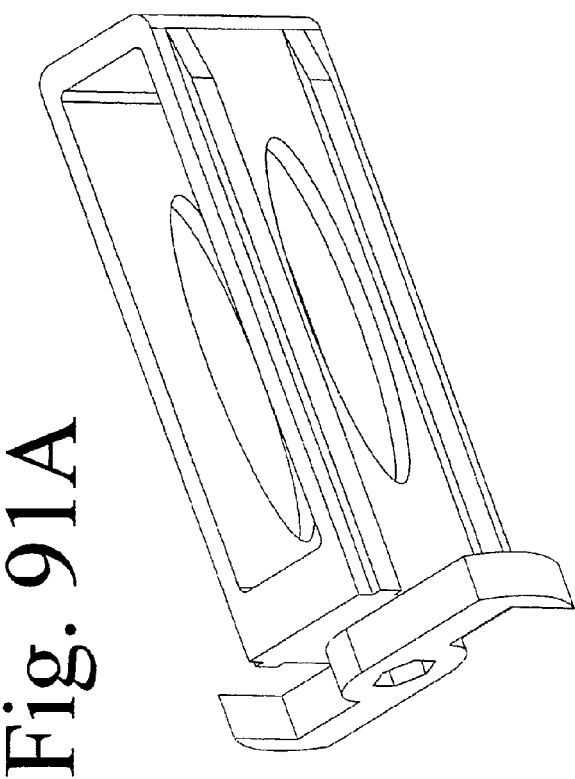
FIG. 91A shows the bone cage and bone anchor placed into an opening within an artificial disc prosthesis with the anchor in the un-engaged position.

The bone cage and bone anchor 3101 are placed into an opening 1903 within an artificial disc prosthesis with the anchor in the un-engaged (horizontal) position—as illustrated in FIG. 91A. After the cage is positioned, bone anchor 3101 is rotated into the engaged (vertical) position as shown in FIG. 91B. In this way, bone anchor 3101 provides additional fixation onto the adjacent vertebral bones.

Figure 92:
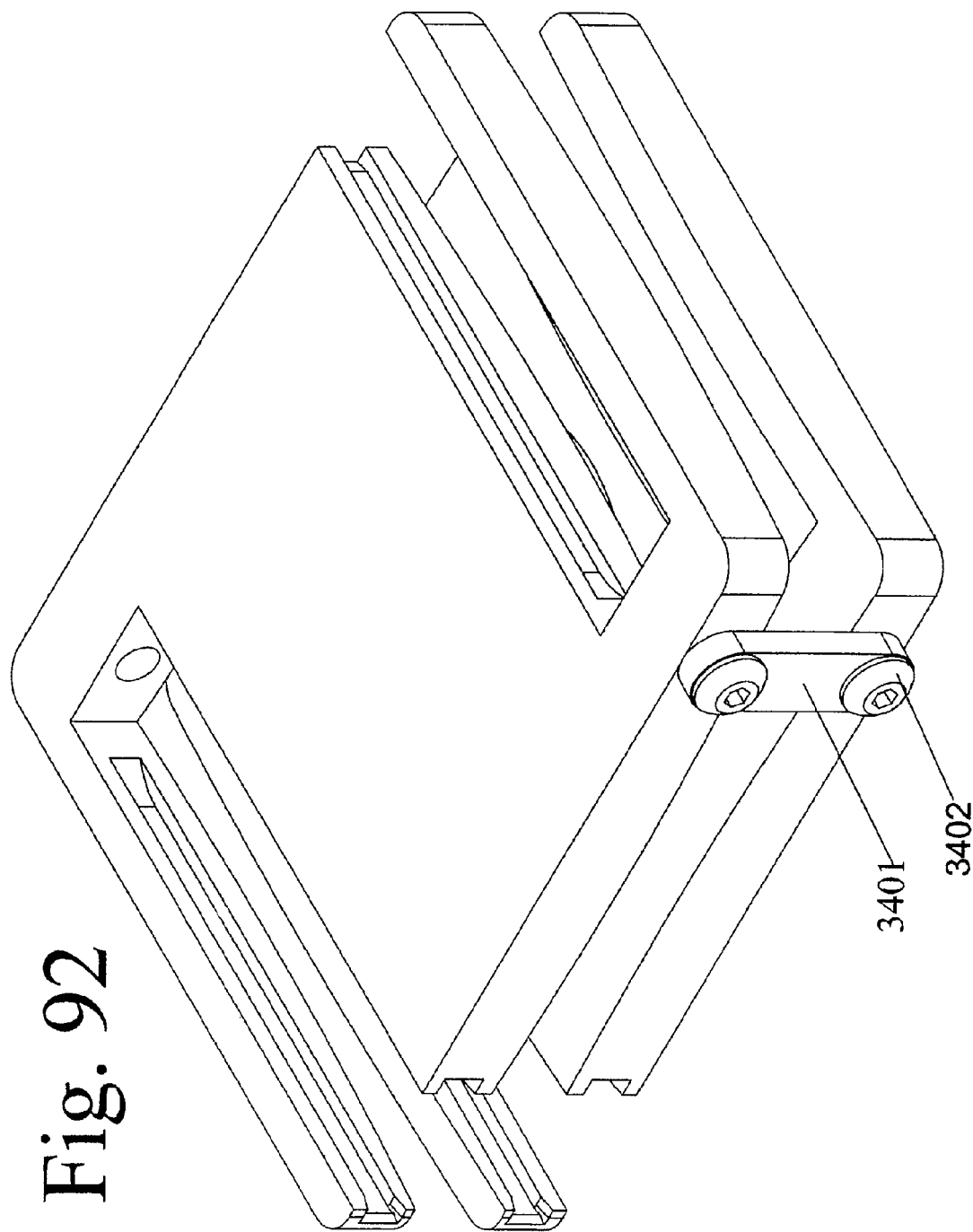
FIG. 92 shows another embodiment in which the openings are adapted to open in different directions.
Figure 93:
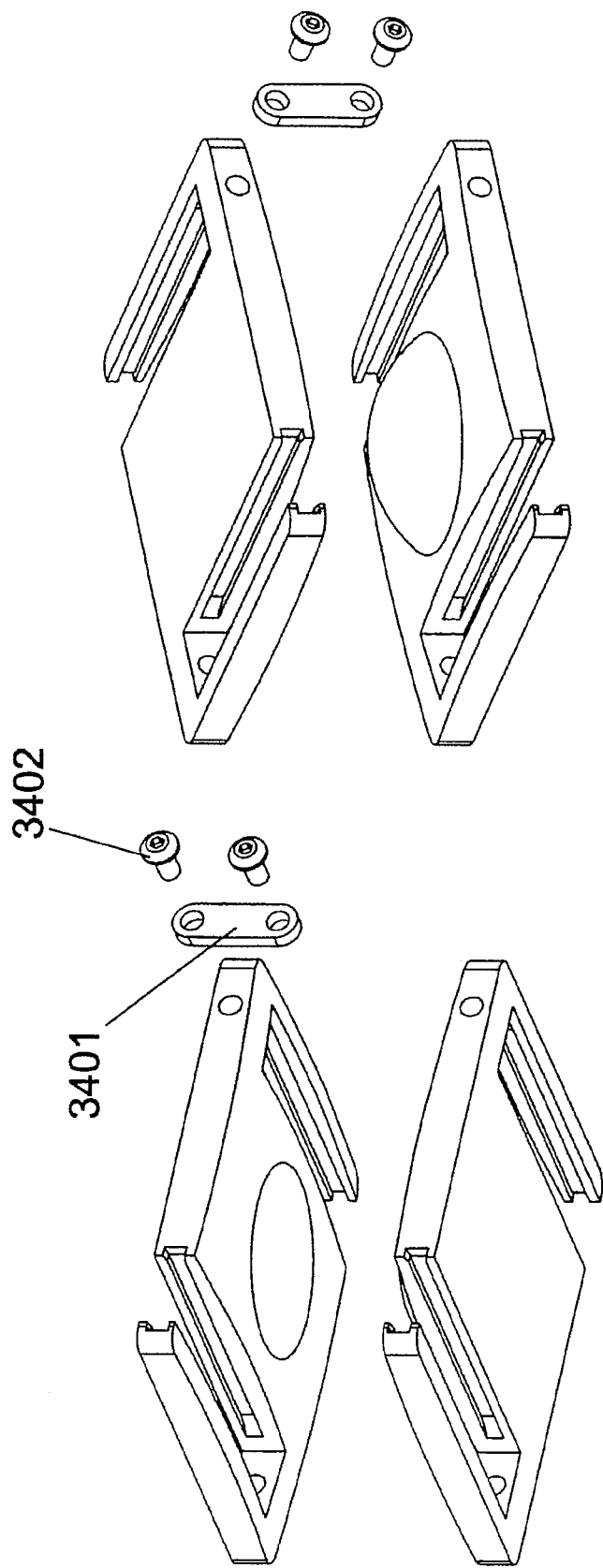
FIG. 93 shows an exploded view of the upper and lower segments of an artificial prosthesis device and an attachment bar.

FIG. 92 shows another embodiment in which the openings 1903 are adapted to open in different directions. An attachment bar 3401 and threaded screws 3402 (threads not shown) may be used to fixate the upper segment 1901A and lower segment 1901B. FIG. 93 shows an exploded view of the upper and lower segments of an artificial prosthesis device and the attachment bar 3401. As shown in FIG. 92, screws may used to attach bar 3401 onto both the upper and lower segments of the artificial disc prosthesis. Alternatively, a staple may be used to connect the segments.

Figures 94A, 94B:
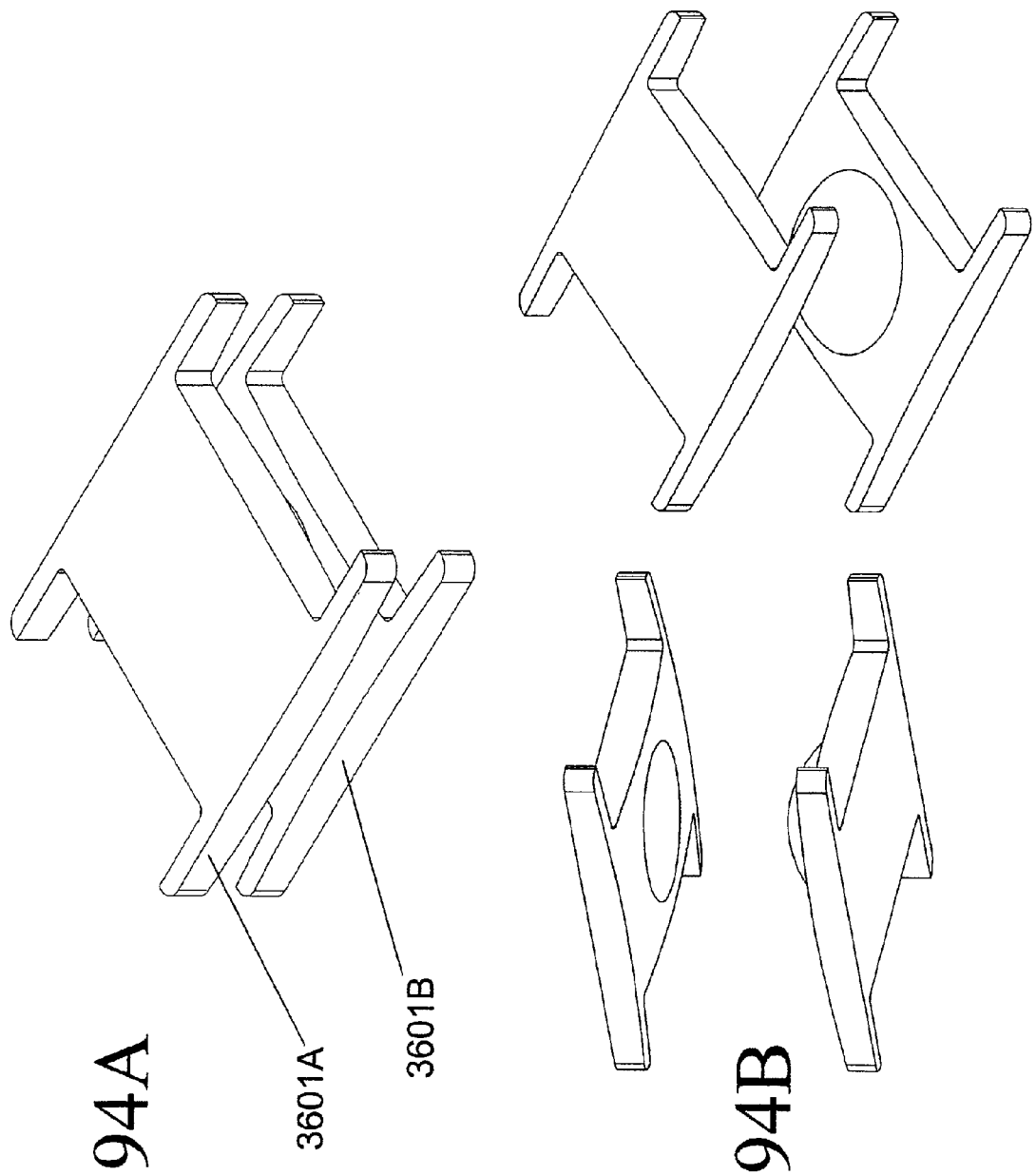
FIG. 94A shows another embodiment of the upper and lower segments for an artificial disc prosthesis.
FIG. 94B shows perspective views of the disassembled device of FIG. 94A.
Figure 95A:
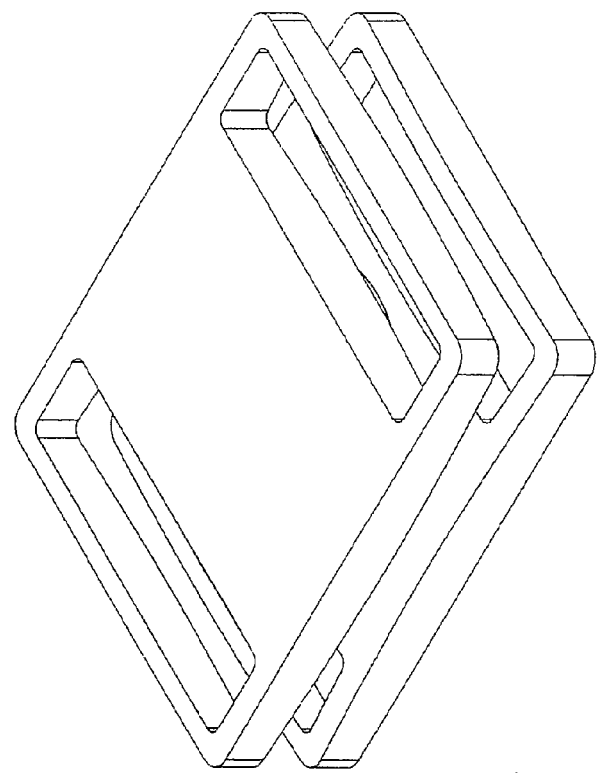
FIG. 95A shows an alternative embodiment of a prosthesis.

FIG. 94A shows another embodiment of the upper and lower segments for an artificial disc prosthesis. FIG. 94B shows perspective views of the disassembled device. In this embodiment, the upper segment 3601A and corresponding lower segment 3601B contain fusion bone (and/or cage) accommodating cavities that open onto the lateral surface of the prosthesis. In this embodiment, the bone and/or bone cage may be preferably, but not necessarily, placed from a lateral approach. An alternative embodiment is shown in FIG. 95A.

Figure 95B:
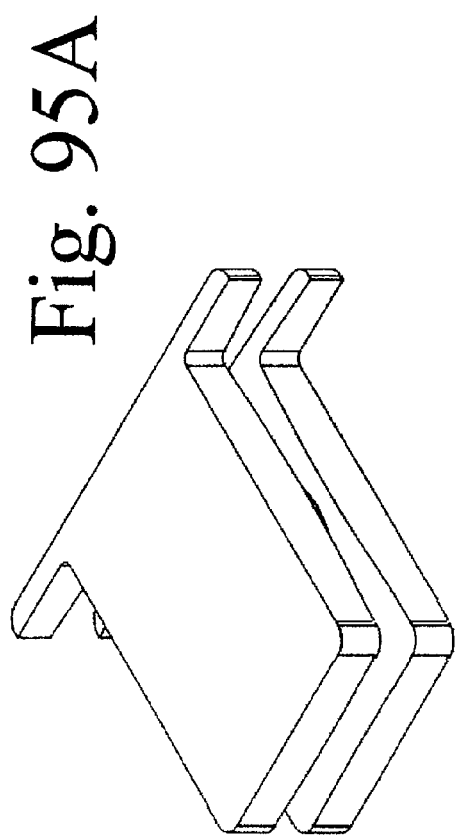
FIG. 95B shows another embodiment of the upper and lower segments for an artificial disc prosthesis.

FIG. 95B shows another embodiment of the upper and lower segments for an artificial disc prosthesis. In this embodiment, there are one or more cavities that are adapted to contain a bone graft and/or bone cage. The cavities do not contain an open side.

Any of the embodiments disclosed in this application and/or their components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, the prosthesis surface(s) that are adjacent to bone may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the illustrated embodiments and/or any component can also be entirely or partially made of a shape memory material or other deformable material.

The shown embodiments are illustrative and do not limit the scope of the invention. At a minimum, additional embodiments of the present invention can be created by one of ordinary skill using various combinations of the embodiments illustrated herein. It is understood that various modifications may be made without departing from the spirit and scope of the claims. Accordingly, other embodiments are within the scope of the following claims.

What is claimed is:

1. A method for the correction of vertebral scoliosis without bone fusion using a minimally invasive surgical technique, comprising:

laterally approaching a side of a convexity of a deformity in the spine, wherein the side of the convexity is a side of the vertebral midline in which the vertical distance between the pedicle portion of each vertebral body of the spine is greatest; and placing a mobile orthopedic prosthesis into a disc space via the lateral approach, wherein the orthopedic prosthesis contains at least one bearing surface that is adapted to at least partially replace a natural inter-vertebral disc, wherein the length of the prosthesis in the coronal plane is less than that of the inter-vertebral disc.

2. A method of repairing and augmenting a fractured vertebral body that abuts an implanted mobile disc prosthesis without fusion to another vertebral body, comprising:

placing a rigid orthopedic brace across a fracture site via a convex side of a spine deformity and anchoring the brace to bone using bone fasteners on either side of the fracture site, wherein the brace contains at least one rigid member wherein the brace is positioned in the disc space so as to resist aberrant settlement of an upper vertebral bone relative to a lower vertebral bone and re-formation of the abnormal alignment in the coronal plane; and preserving the mobility of a natural disc or mobile disc prosthesis that abuts the fractured vertebra.

3. An orthopedic implant that is adapted to be positioned within a space between a first bone and an adjacent second bone, comprising:

a first member having a first abutment surface that is adapted to abut a first surface of the first bone, wherein the first member further contains a second abutment surface that is adapted to form a first articulation with a second member;

the second member having a first abutment surface that is adapted to abut a first surface of the second bone, wherein the second member further contains a second abutment surface that is adapted to form the first articulation with the second abutment surface of the first member, and wherein the second member is movable relative to the first member across the first articulation;

a cavity that is at least partially contained within the implant and adapted to accept a bone forming material, wherein the cavity contains a first aperture that opens onto a surface of the first bone and at least a second aperture that opens onto a surface of the second bone, wherein bone forming material, when implanted into the cavity, directly contacts a surface of each of said first and the second bones and produces a bony fusion that abolishes movement between them.

4. An orthopedic implant as in claim 3, having a third member, wherein the third member is adapted to be at least partially positioned within the cavity of the implant, and wherein the third member contains a first abutment surface that is adapted to abut a bone surface of the first bone, a second abutment surface that is adapted to abut a bony surface of the second bone and at least one connecting member between the first and second abutment surfaces of the third member.

5. An orthopedic implant as in claim 4, wherein the third member forms a receptacle that is adapted to at least partially contain a bone graft material.

6. An orthopedic implant as in claim 4, wherein the third member is adapted to support at least a portion of a load transmitted between the first and the second bone.

7. An orthopedic implant as in claim 4, wherein the third member is adapted to limit motion between the first and the second bones.

8. An orthopedic implant as in claim 4, wherein the third member is adapted to return the position of the first bone to a predetermined relationship relative to the second bone.

9. An orthopedic implant as in claim 4, wherein the third member is adapted to rigidly affix onto the first bone.

10. An orthopedic implant as in claim 4, wherein the third member is adapted to rigidly affix onto the second bone.

11. An orthopedic implant as in claim 4, wherein the third member is adapted to rigidly affix the first bone onto the second bone.

12. An orthopedic implant as in claim 4, wherein the third member is adapted to limit motion between the first member and the second member of the prosthesis.

13. An orthopedic implant as in claim 3, wherein a fixation member is adapted to rigidly immobilize the first member relative to the second member.

14. A method for the treatment of cervical spine disease, comprising:
positioning a first orthopedic implant into at least one unco-vertebral joint at the level of a diseased cervical intervertebral disc, wherein the joint is located between an unicate process of a superior surface of an inferior cervical vertebral bone and an inferior surface of an adjacent superior cervical bone;
orienting the implant so that an inferior abutment surface of the implant rests atop the uncite process of the superior surface of the interior vertebral bone;
leaving at least a segment of the diseased cervical intervertebral disc undisturbed.

15. A method as in claim 14, wherein the inferior abutment surface of the first implant forms an oblique angle with the body of the diseased cervical intervertebral disc.

16. A method as in claim 14, wherein a second orthopedic implant is positioned into the contra-lateral unco-vertebral joints at the level of a diseased cervical intervertebral disc.

17. A method as in claim 16, wherein an inferior abutment surface of the second implant forms an oblique angle with the body of the diseased cervical intervertebral disc.

18. A method as in claim 16, wherein the second implant maintains movement between the superior and inferior cervical vertebral bones that border the diseased cervical intervertebral disc.

19. A method as in claim 18, wherein the second implant contains a visco-elastic member.

20. A method as in claim 14, wherein the first implant maintains movement between the superior and inferior cervical vertebral bones that border the diseased cervical intervertebral disc.

21. A method as in claim 20, wherein the first implant contains a visco-elastic member.

22. An orthopedic implant that is adapted to be positioned within an intervertebral disc space that is between a first vertebral bone and an adjacent second vertebral bone, comprising:
a first implant member having a bone abutment surface that is adapted to abut a first surface of the first vertebral bone, wherein the first member contains a first bearing surface and a second bearing surface that are rigidly connected to one another by a first interposed segment;
a second implant member having a bone abutment surface that is adapted to abut a first surface of the second vertebral bone, wherein the second member contains a first bearing surface that is adapted to articulate with the first bearing surface of the first member, wherein the second member contains a second bearing surface that is adapted to articulate with the second bearing surface of the first member;
wherein motion between the first and the second vertebral bones is maintained by the implant, and wherein the first member articulates with the second member at the first and second bearing surfaces alone.

23. An orthopedic implant as in claim 22, wherein the first and second bearing surfaces of the second implant member are separated by a first distance.

24. An orthopedic implant as in claim 23, wherein the first distance is variable.

25. An orthopedic implant as in claim 23, wherein the distance between the bone abutment surface of the first implant member and the bone abutment surface of the second implant member is determined by the first distance of the second implant member.

26. An orthopedic implant as in claim 22, wherein the first bearing surface of the second implant member is coupled to a first malleable member.

27. An orthopedic implant as in claim 26, wherein the first malleable member is adapted to resist movement of the first bearing surface towards the second bearing surface.

28. An orthopedic implant as in claim 26, wherein the first malleable member opposes a compressive force that urges the first vertebral bone towards the second vertebral bone.

29. An orthopedic implant as in claim 22, wherein the second bearing surface of the second implant member is coupled to a second malleable member.

30. An orthopedic implant as in claim 29, wherein the second malleable member is adapted to resist movement of the second bearing surface towards the first bearing surface.

31. An orthopedic implant as in claim 29, wherein the second malleable member opposes a compressive force that urges the first vertebral bone towards the second vertebral bone.

32. An orthopedic implant as in claim 22, wherein at least one of said implant members contains a projection that extends outward from a bone abutment surface and away for the bearing surfaces.

33. An orthopedic implant as in claim 32, wherein the projection forms a ridge extending along a longitudinal axis and having a total width, wherein the ridge contains at least one movable segment that is adapted to rotate from a first to a second configuration relative to a second ridge segment, and wherein the total width of the ridge is greater when the movable segment is in the second configuration.

34. An orthopedic implant as in claim 33, wherein the movable segment is in the first configuration prior to positioning the implant within the intervertebral disc space, and wherein the movable member is transitioned to the second configuration after positioning the implant.

35. An orthopedic implant as in claim 22, wherein the first implant members contains an anterior surface and an elongated member that extends posteriorly along a first longitudinal axis form a aperture of said anterior surface, the elongated member being attached to a proximal aspect of a bone fixation member, wherein the fixation member is adapted to rotate in a circular trajectory about the first longitudinal axis;
wherein the bone fixation member contains a curved distal tip that is tapered along the direction of rotation of the first circular trajectory, wherein the tapered tip is adapted to forcibly advance and fixate into the adjacent first vertebral bone when the fixation member is rotated in the direction of the taper, and wherein the fixation member is separated from simultaneous anchor into each of the first and the second vertebral bones.

36. A mobile orthopedic implant that is adapted to be positioned within an intervertebral disc space between a first vertebral bone and an adjacent second vertebral bone, comprising:
  a first implant member having a bone abutment surface that is adapted to abut a surface of the first vertebral bone and having a first bearing that is adapted to articulate with a bearing surface of a second implant member;
  an elongated member that extends posteriorly along a first longitudinal axis form a aperture of an anterior surface of the first implant member, the elongated member being attached to a proximal aspect of at least one bone fixation member, wherein the fixation member is adapted to rotate in a circular trajectory about the first longitudinal axis, wherein the bone fixation member contains a curved distal tip that is tapered along the direction of rotation of the first circular trajectory, wherein the tapered tip is adapted to forcibly advance and fixate into the adjacent first vertebral bone when the fixation member is rotated in the direction of the taper, and wherein the fixation member is separated from simultaneous anchor into each of the first and the second vertebral bones;
  a second implant member having a bone abutment surface that is adapted to abut a surface of the second vertebral bone and having a first bearing that is adapted to articulate with the first bearing surface of the first implant member, wherein the articulation maintains motion between said first and second vertebral bones.

37. An orthopedic implant as in claim 36, wherein at least a segment of the implant is manufactured from a metallic alloy.

38. An orthopedic implant as in claim 37, wherein the metallic alloy is at least partially comprised of Titanium.

39. An orthopedic implant as in claim 36, wherein at least a segment of the implant is manufactured from a plastic material.

40. An orthopedic implant as in claim 36, wherein the bone fixation member is in a first rotational position before the device is implanted into the inter-vertebral space, and wherein the bone fixation member is transitioned into a second rotational position after device implantation wherein the implant is positioned into the inter-vertebral space while the bone fixation member is in a first rotational position, and wherein the fixation member is subsequently rotated into a second rotational position.

41. An orthopedic implant as in claim 40, wherein the fixation member provides greater implant fixation to bone when in the second rotational position.

42. A orthopedic implant adapted to be positioned within an intervertebral disc space that is between a first vertebral bone and an adjacent second vertebral bone, comprising:
  a first bone abutment surface that is adapted to abut a surface of the first vertebral bone and a second bone abutment surface that is adapted to abut a surface of the second vertebral bone;
  a projection that extends outward along a longitudinal axis from the first bone abutment surface, wherein the projection forms a ridge having a total width, wherein the ridge contains at least one movable segment that is adapted to rotate from a first to a second position relative to a second ridge segment, and wherein the total width of the ridge is greater when the movable segment is in the second position.

43. An orthopedic implant as in claim 42, wherein at least a segment of the implant is manufactured from a metallic alloy.

44. An orthopedic implant as in claim 42, wherein at least a segment of the implant is manufactured from a plastic material.

45. An orthopedic implant as in claim 42, wherein the movable segment is in the first position before the device is implanted into the inter-vertebral space, and wherein the movable segment is transitioned into the second position after device implantation.

46. An orthopedic implant for placement within an intervertebral disc space that is positioned between a first and a second immediately-adjacent vertebral bones, comprising:
  a body having a first bone abutment surface that can abut the first vertebral bone, a second bone abutment surface that can abut the second vertebral bone and a connecting segment that joins the said abutment surfaces, wherein the body extends from an anterior surface to a posterior end, wherein the anterior surface contains at least one aperture that extends along a first trajectory and onto at least one of said abutment surfaces;
  an anchor that is adapted to be positioned within the aperture of the anterior surface and to extend from a proximal segment to a distal end along a trajectory that is at least partially curvilinear, wherein the anchor has a total length greater than that of the aperture, wherein, when seated in the aperture, at least the distal end of the anchor is positioned within one of the said vertebral bones and separated from threaded engagement with it.

47. An orthopedic prosthesis as in claim 46, wherein the anchor is separated from simultaneous engagement of each of the first and the second vertebral bones when it is seated in the aperture.

48. An orthopedic prosthesis as in claim 46, wherein at least a segment of the first trajectory is curvilinear.

49. An orthopedic prosthesis as in claim 46, wherein a proximal end of the anchor is larger than the internal dimensions of aperture.

50. An orthopedic prosthesis as in claim 46, wherein the distal end of the anchor is formed of a tapered tip.

51. An orthopedic prosthesis as in claim 50, wherein the tapered tip is sufficiently stiff to be advanced into the vertebral bone.

* * * * *